US008835162B2

(12) United States Patent
Kwon et al.

(10) Patent No.: US 8,835,162 B2
(45) Date of Patent: *Sep. 16, 2014

(54) METHODS OF INCORPORATING AMINO ACID ANALOGS INTO PROTEINS

(71) Applicant: California Institute of Technology, Pasadena, CA (US)

(72) Inventors: Inchan Kwon, Pasadena, CA (US); David Tirrell, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/730,116

(22) Filed: Dec. 28, 2012

(65) Prior Publication Data

US 2013/0210073 A1 Aug. 15, 2013

Related U.S. Application Data

(63) Continuation of application No. 12/698,837, filed on Feb. 2, 2010, now abandoned, which is a continuation of application No. 11/130,583, filed on May 17, 2005, now abandoned.

(60) Provisional application No. 60/571,810, filed on May 17, 2004.

(51) Int. Cl.
C12N 15/70 (2006.01)

(52) U.S. Cl.
USPC .............. 435/320.1; 435/252.2; 435/69.1; 435/68.1; 435/41; 435/252.8; 506/18; 506/26; 506/1; 506/16; 506/11; 424/94.5; 424/93.2

(58) Field of Classification Search
CPC combination set(s) only.
See application file for complete search history.

(56) References Cited

U.S. PATENT DOCUMENTS

| | | | |
|---|---|---|---|
| 6,269,312 B1 | 7/2001 | Mayo et al. |
| 6,331,418 B1 | 12/2001 | Roth |
| 6,927,042 B2 | 8/2005 | Schultz et al. |
| 7,045,337 B2 | 5/2006 | Schultz et al. |
| 7,083,970 B2 | 8/2006 | Schultz et al. |
| 7,139,665 B2 | 11/2006 | Datta et al. |
| 7,449,443 B2 | 11/2008 | Tirrell et al. |
| 2004/0053390 A1 | 3/2004 | Datta et al. |
| 2005/0260711 A1 | 11/2005 | Datta et al. |
| 2005/0287639 A1 | 12/2005 | Kwon et al. |
| 2008/0044854 A1 | 2/2008 | Wang et al. |

FOREIGN PATENT DOCUMENTS

| | | |
|---|---|---|
| EP | 0 318 948 A2 | 6/1989 |
| EP | 0 328 147 A2 | 8/1989 |
| WO | WO 92/16640 A1 | 10/1992 |
| WO | WO 02/085923 A2 | 10/2002 |
| WO | WO 03/031464 A2 | 4/2003 |
| WO | WO 2007/103307 A2 | 9/2007 |

OTHER PUBLICATIONS

Genbank Database Accession No. AAD26531, Apr. 21, 1999.
Genbank Database Accession No. AAF10907, Dec. 28, 2005.
Anderson et al., "Fluorescence Resonance Energy Transfer Between Unnatural Amino Acids in a Structurally Modified Dihydrofolate Reductase," *J. Am. Chem. Soc.*, 124(33): 9674-9675, Aug. 21, 2002.
Azoulay et al., "Glutamine analogues as potential antimalarials," *Eur. J. Med. Chem.* 26: 201-205, 1991.
Bain et al., "Biosynthetic Site-Specified Incorporation of a Non-Natural Amino Acid into a Polypeptide," *J. Am. Chem. Soc.*, 111: 8013-8014, 1989.
Bain et al., "Ribosome-mediated Incorporation of a Non-standard Amino Acid into a Peptide Through Expansion of the Genetic Code," *Nature* 356(6369): 537-9, Apr. 9, 1992.
Bernstein et al., "The Protein Data Bank: A Computer-based Archival File for Macromolecular Structures," *J. Mol. Biol.* 112(3): 535-42, May 25, 1977.
Borén et al., "Undiscriminating Codon Reading with Adenosine in the Wobble Position," *J. Mol. Biol.* 230: 739-749, 1993.
Bowen et al., "Relationship Between Molecular Mass and Duration of Activity of Polyethylene Glycol Conjugated Granulocyte Colony-stimulating Factor Mutein," *Exp. Hematol.* 27(3): 425-32, Mar. 1999.
Budisa et al., "High-level Biosynthetic Substitution of Methionine in Proteins by its Analogs 2-aminohexanoic Acid, Selenomethionine, Telluromethionine and Ethionine in *Escherichia coli*," *Eur. J. Biochem.* 230(2): 788-96, Jun. 1, 1995.
Chen et al., "A Cytosolic tRNA with an Unmodified Adenosine in the Wobble Position Reads a Codon Ending with the Non-complementary Nucleoside Cytidine," *J. Mol. Biol.* 317: 481-492, 2002.
Clark et al., "Long-acting Growth Hormones Produced by Conjugation with Polyethylene Glycol," *J. Biol. Chem.* 271(36):21969-21977, Sep. 6, 1996.
Craig et al., "Absolute Configuration of the Enantiomers of 7-Chloro-4-[[4-(diethylamino)-1-methylbutyl]amino]quinolone (Chloroquine)," *J. Org. Chem.* 53: 1167-1170, 1988.
Crick, "Codon—Anticodon Pairing: The Wobble Hypothesis," *J. Mol. Biol.* 19: 548-555, 1966.
Christie et al., "Synthesis of Optically Pure Pipecolates from L-Asparagine. Application to the Total Synthesis of (+)-Apovincamine through Amino Acid Decarbonylation and Iminium Ion Cyclization," *J. Org. Chem.* 50: 1239-1246, 1985.
Datta et al., "A Designed Phenylalanyl-tRNA Synthetase Variant Allows Efficient in Vivo Incorporation of Aryl Ketone Functionality into Proteins," *J. Am. Chem. Soc.* 124(20): 5652-5653, May 22, 2002.
Davis et al., "A Novel Method for the Specific Glycosylation of Proteins," *Tetrahedron Lett.* 32: 6793-6796, 1991.
Dayie et al., "Theory and Practice of Nuclear Spin Relaxation in Proteins," *Annu. Rev. Phys. Chem.* 47: 243-82, 1996.
Deiters et al., "Site-specific PEGylation of Proteins Containing Unnatural Amino Acids," *Bioorg. Med. Chem. Lett.* 14(23): 5743-5, Dec. 6, 2004.
Deming et al., "Biosynthetic Incorporation and chemical Modification of Alkene Functionality in Genetically Engineered Polymers," *J. Macromol. Sci. Pure Appl. Chem.* A34(10):2143-2150, 1997.
Desmet et al., "The Dead-end Elimination Theorem and its Use in Protein Side-chain Positioning," *Nature* 356: 539-542, Apr. 9, 1992.
Doctor et al., "Species Specificity of Amino Acid Acceptor Ribonucleic Acid and Aminoacyl Soluble Ribonucleic Acid Synthetases," *J. Bio.l Chem.* 238(11):3677-81, Nov. 1963.

(Continued)

*Primary Examiner* — Kagnew H Gebreyesus
(74) *Attorney, Agent, or Firm* — Seed IP Law Group PLLC

(57) ABSTRACT

The invention provides a method of incorporating nonstandard amino acids into a protein by utilizing a modified aminoacyl-tRNA synthetase to charge the nonstandard amino acid to a modified tRNA, which forms strict Watson-Crick base-pairing with a codon that normally forms wobble base-pairing with natural tRNAs.

15 Claims, 8 Drawing Sheets

(56) References Cited

OTHER PUBLICATIONS

Döring et al., "Enlarging the Amino Acid set of *Escherichia coli* by Infiltration of the Valine Coding Pathway," *Science* 292(5516):501-504, Apr. 20, 2001.

Dougherty, "Unnatural Amino Acids as Probes of Protein Structure and Function," *Curr. Opin. Chem. Biol.* 4(6): 645-652, Dec. 2000.

Duewel et al., "Incorporation of Trifluoromethionine into a Phage Lysozyme: Implications and a New Marker for Use in Protein $^{19}$F NMR," *Biochemistry* 36(11): 3404-3416, Mar. 18, 1997.

Dunbrack et al., "Conformational Analysis of the Backbone-dependent Rotamer Preferences of Protein Sidechains," *Nat Struct Biol.* 1(5): 334-340, May 1994.

Fourme et al., "Better Structures from Better Data Through Better Methods: A Review of Developments in *de novo* Macromolecular Phasing Techniques and Associated Instrumentation at LURE," *J. Synchrotron Radiat.* 6: 834-844, 1999.

Friedman et al., "Synthesis of Derivatives of Glutamine as Model Substrates for Anti-tumor Agents," *J. Am. Chem. Soc.* 81: 3750-3572, 1959.

Furter, "Expansion of the Genetic Code: Site-directed p-fluorophenylalanine Incorporation in *Escherichia coli*," *Protein Sci.* 7(2): 419-426, Feb. 1998.

Gardner et al., "The Use of 2H, 13C, 15N Multidimensional NMR to Study the Structure and Dynamics of Proteins," *Annu. Rev. Biophys. Biomol. Struct.* 27: 357-406, 1998.

Giege et al., "Aspartate Identity of Transfer RNAs," *Biochimie.* 78(7): 605-623, 1996.

Hinsberg, "Direct Studies of 1,1-Diazenes. Syntheses, Infrared and Electronic Spectra, and Kinetics of the Thermal Decomposition of N-(2,2,6,6-Tetramethylpiperidyl)Nitrene and N-(2,2,5,5-Tetramethylpyrrolidyl)Nitrene and N-(2,2,5,5-Tetramethylpyrrolidyl)Nitrene," *J. Am. Chem. Soc.*104: 766-773, 1982.

Hohsaka et al., "Site-specific Incorporation of Photofunctional Nonnatural Amino Acids into a Polypeptide Through in Vitro Protein Biosynthesis," *FEBS Lett.* 344(2-3): 171-274, May 16, 1994.

Hohsaka et al., "Five-base Codons for Incorporation of Nonnatural Amino Acids Into Proteins," *Nucleic Acids Res.* 29(17): 3646-3651, Sep. 1, 2001.

Holmes et al., "Differential utilization of leucyl-tRNAs by *Escherichia coli*," *Proc. Natl. Acad. Sci. USA* 74(4): 1393-1397, Apr. 1977.

Ibba et al., "Substrate Specificity is Determined by Amino Acid Binding Pocket size in *Escherichia coli* Phenylalanyl-tRNA Synthetase," *Biochemistry* 33(23): 7107-7112, Jun. 14, 1994.

Inagaki et al., "Translation of Synonymous Codons in Family Boxes by *Mycoplasma capricolum* tRNAs with Unmodified Uridine or Adenosine at the First Anticodon Position," *J. Mol. Biol.* 251: 486-492, 1995.

Ishima et al., "Protein Dynamics from NMR," *Nat. Struct. Biol.* 7(9): 740-743, Sep. 2000.

Kahn et al., "Feasibility and Review of Anomalous X-ray Diffraction at Long Wavelengths in Materials Research and Protein Crystallography," *J. Synchrotron Radiat.* 7: 131-138, 2000.

Kanamori et al., "Deaminated neuraminic Acid-rich Glycoprotein of Rainbow Trout Egg Vitelline Envelope. Occurrence of a novel alpha-2,8-linked oligo(deaminated neuraminic acid) structure in O-linked glycan chains," *J. Biol. Chem.* 265(35): 21811-21819, Dec. 15, 1990.

Kast et al., "Amino Acid Substrate Specificity of *Escherichia coli* Phenylalanyl-tRNA Synthetase Altered by Distinct Mutations," *J. Mol. Biol.* 222(1): 99-124, Nov. 5, 1991.

Kay, "NMR Methods for the Study of Protein Structure and Dynamics," *Biochem. Cell Biol.* 75(1): 1-15, 1997.

King et al., "A New Synthesis of Glutamine and of γ-Dipeptides of Glutamic Acid from Phthalylated Intermediates," *J. Chem. Soc.* 3315-3319, 1949.

Kowal et al., "Exploiting Unassigned Codons in *Micrococcus luteus* for tRNA-based Amino Acid Mutagenesis," *Nucleic Acids Res.* 25(22): 4685-4689, Nov. 15, 1997.

Kowal et al., "Twenty-first Aminoacyl-tRNA Synthetase-suppressor tRNA Pairs for Possible Use in Site-specific Incorporation of Amino Acid Analogues into Proteins in Eukaryotes and in Eubacteria," *Proc. Natl. Acad. Sci. USA.* 98(5): 2268-2273, Feb. 27, 2001.

Kwok et al., "Evolutionary Relationship Between *Halobacterium cutirubrum* and Eukaryotes Determined by Use of Aminoacyl-tRNA Synthetases as Phylogenetic Probes," *Can. J. Biochem.* 58(3): 213-218, Mar. 1980.

Kwon et al., "Breaking the Degeneracy of the Genetic Code," *J. Am. Chem. Soc.* 125(25): 7512-7513, Jun. 25, 2003.

Liu et al., "Progress Toward the Evolution of an Organism with an Expanded Genetic code," *Proc. Natl. Acad. Sci. USA.* 96(9): 4780-4785, Apr. 27, 1999.

Macmillan et al., "Solid-phase Synthesis of Thioether-linked Glycopeptide Mimics for Application to Glycopeptide Mimics for Application to Glycoprotein Semisynthesis," *Org. Lett.* (9): 1467-1470, May 2, 2002.

Marchler-Bauer et al., "MMDB: Entrez's 3D Structure Database," *Nucleic Acids Res.* 27(1): 240-243, Jan. 1, 1999.

Matsoukas et al., "Differences in Backbone Structure between Angiotensin II Agonists and Type I Antagonists," *J. Med. Chem.* 38: 4660-4669, 1995.

Nadano et al., "A Naturally Occurring Deaminated Neuraminic Acid, 3-deoxy-D-glycero-D-galacto-nonulosonic Acid (KDN). Its Unique Occurrence at the Nonreducing Ends of Oligosialyl Chains in Polysialoglycoprotein of Rainbow Trout Eggs," *J. Biol. Chem.* 261(25): 11550-11557, Sep. 5, 1986.

Noren et al., "A General Method for Site-specific Incorporation of Unnatural Amino Acids into Proteins," *Science* 244(4901): 182-188, Apr. 14, 1989.

Nowak et al., "Nicotinic Receptor Binding Site Probed with Unnatural Amino Acid Incorporation in Intact Cells," *Science* 268(5209): 439-442, Apr. 21, 1995.

Oakley et al., "Macromolecular Crystallography as a Tool for Investigating Drug, Enzyme and Receptor Interactions," *Clin. Exp. Pharmacol. Physiol.* 27(3): 145-251, Mar. 2000.

Ohno et al., "Changing the Amino Acid Specificity of Yeast Tyrosyl-tRNA Synthetase by Genetic Engineering," *J. Biochem.* (Tokyo) 130(3): 417-423, Sep. 2001.

Pastrnak et al., "A New Orthogonal Suppressor tRNA/Aminoacyl-tRNA Synthetase Pair for Evolving an Organism with an Expanded Genetic Code," *Helv. Chim. Acta* 83: 2277-3386, 2000.

Paulson et al., "Sialyl- and Fucosyltransferases in the Biosynthesis of Asparaginyl-linked Oligosaccharides in Glycoproteins. Mutually Exclusive Glycosylation by β-galactoside α2 goes to 6 Sialyltransferase and N-acetylglucosaminide α1 goes to 3 fucosyltransferase," *J. Biol. Chem.* 253(16): 5617-5624, Aug. 25, 1978.

Peterson, "Determination of Recognition Nucleotides for *Escherichia coli* PhenylalanyltRNA Synthetase," *Biochemistry* 31(42): 10380-10389, Oct. 27, 1992.

Pollack et al., "Introduction of Nucleophiles and Spectroscopic Probes into Antibody Combining Sites," *Science* 242(4881): 1038-1040, Nov. 18, 1998.

Ponder et al., "Tertiary Templates for Proteins Use of Packing Criteria in the Enumeration of Allowed Sequences for Different Structural Classes," *J. Mol. Biol.* 193: 775-791, 1987.

Rostovtsev et al., "A Stepwise Huisgen Cycloaddition Process: Copper(I)-Catalyzed Regioselective 'Ligation' of Azides and Terminal Alkynes," *Angew. Chem. Int. Ed.* 41(14): 2596-2599, 2002.

Sarkar et al., "Rational Cytokine Design for Increased Lifetime and Enhanced Potency Using pH-activated 'Histidine Switching'," *Nat. Biotechnol.* 20(9): 908-913, Sep. 2002.

Schultz et al., "Photochemistry of a 1,1-Diazene, N-(2,2,5,5-Tetramethylpyrrolidinyl)Nitrene," *J. Am. Chem. Soc.* 103: 1563-1564, 1981.

Sharma et al., "Efficient Introduction of Aryl Bromide Functionality into Proteins in Vivo," *FEBS Lett.* 467(1): 37-40, Feb. 4, 2000.

Shin et al., "Fmoc-Based Synthesis of Peptide-$^{α}$Thioesters: Application to the Total Chemical Synthesis of a Glycoprotein by Native Chemical Ligation," *J. Am. Chem. Soc.* 121: 11684-11689, 1999.

Snoek et al., "The Sequence and Organization of the Mouse Valyl-tRNA Synthetase Gene G7a/Bat6 Located in the MHC class III Region," *Immunogenetics* 49(5): 468-740, May 1999.

(56) References Cited

OTHER PUBLICATIONS

Söll et al., "Studies on Polynucleotides: LXXVI. Specificity of Transfer RNA for Codon Recognition as Studied by Amino Acid Incorporation," *J. Mol. Biol.* 29: 113-124, 1967.

Szymanski et al., "Aminoacyl-tRNA Synthetases Database," *Nucleic Acids Res.* 29: 288-290, 2001.

Tang et al., "Attenuation of the Editing Activity of the *Escherichia coli* Leucyl-tRNA Synthetase Allows Incorporation of Novel Amino Acids into Proteins in Vivo," *Biochemistry* 41(34): 10635-10645, Aug. 27, 2002.

Tolbert et al., "Intein-Mediated Synthesis of Proteins Containing Carbohydrates and Other Molecular Probes," *J. Am. Chem. Soc.* 122: 5421-5428, 2000.

Tornøe et al., "Peptidotriazoles on Solid Phase: [1,2,3]-triazoles by Regiospecific Copper(I)-catalyzed 1,3-dipolar Cycloadditions of Terminal Alkynes to Azides," *J. Org. Chem.* 67(9): 3057-3064, May 3, 2002.

van Hest et al., "Efficient Introduction of Alkene Functionality into Proteins in Vivo," *FEBS Lett.* 428(1-2): 68-70, May 22, 1998.

Varki, "Diversity in the Sialic Acids," *Glycobiology* 2(1): 25-40, Feb. 1992.

Varki, "Biological Roles of Oligosaccharides: All of the Theories are Correct," *Glycobiology* 3(2): 97-130, Apr. 1993.

Wang et al., "Bioconjugation by Copper(I)-catalyzed Azide-alkyne [3+2] Cycloaddition," *J. Am. Chem. Soc.* 125(11): 3192-3193, Mar. 19, 2003.

Wang et al., "MMDB: 3D structure data in Entrez," *Nucleic Acids Res.* 28(1): 243-245, Jan. 1, 2000.

Wang et al., "Addition of the Keto Functional Group to the Genetic Code of *Escherichia coli*," *Proc. Natl. Acad. Sci. USA.* 100(1): 56-61, Jan. 7, 2003.

Wang et al., "Expanding the Genetic Code of *Escherichia coli*," *Science* 292(5516): 498-500, Apr. 20, 2001.

Whelihan et al., "Rescuing an Essential Enzyme-RNA Complex with a Non-essential Appended Domain," *EMBO J.* 16(10): 2968-2974, May 15, 1997.

White et al., "Genome Sequence of the Radioresistant Bacterium *Deinococcus radiodurans* R1," *Science* 286(5444): 1571-1577, Nov. 19, 1999.

Wilson et al., "Incorporation of Modified Amino Acids into Proteins in Vivo," *Biochim. Biophys. Acta* 781(3): 205-215, Apr. 5, 1984.

Witte et al., "Enzymatic Glycoprotein Synthesis: Preparation of Ribonuclease Glycoforms via Enzymatic Glycopeptide Condensation and Glycosylation," *J. Am. Chem. Soc.* 119: 2114-2118, 1997.

Witte et al., "Solution- and Solid-Phase Synthesis of N-Protected Glycopeptide Esters of the Benzyl Type as Substrates for Subtilisin-Catalyzed Glycopeptide Couplings," *J. Am. Chem. Soc.* 120: 1979-1989, 1998.

Wuthrich, "NMR—This Other Method for Protein and Nucleic Acid Structure Determination," *Acta Crystallogr. D. Biol. Crystallogr.* D51(Pt 3): 249-370, May 1, 1995.

Kwon and Tirrell, "Multiple-site-specific incorporation of an unnatural amino acid into protein in vivo," *Presentation at the 227th ACS National Meeting*, Mar. 27-Apr. 1, 2004.

Liu et al., "Engineering a tRNA and aminoacyl-tRNA synthetase for the site-specific incorporation of unnatural amino acids into proteins in vivo," *Proc. Natl. Acad. Sci USA* 94: 10092-10097, 1997.

Liu, "Expanding the Scope of Protein Mutagenesis," Ph.D. Thesis, University of California, Berkeley, Spring 1999.

Percudani et al., "Transfer RNA Gene Redundancy and Translational Selection in *Saccharomyces cerevisiae*," *J. Mol. Biol.* 268: 322-330, 1997.

Rodnina and Wintermeyer, "Ribosome fidelity: tRNA discrimination, proofreading and induced fit," *Trends in Biochemical Sciences* 26(2): 124-130, 2001.

Rodin et al., "The presence of codon-anticodon pairs in the acceptor stem of tRNAs," *Proc. Natl. Acad. Sci. USA* 93: 4537-4542, 1996.

Schulman and Pelka, "An anticodon change switches the identity of *E.coli* tRNA$^{Met}$ from methionine to threonine," *Nucleic Acids Research* 18(2): 285-289, 1990.

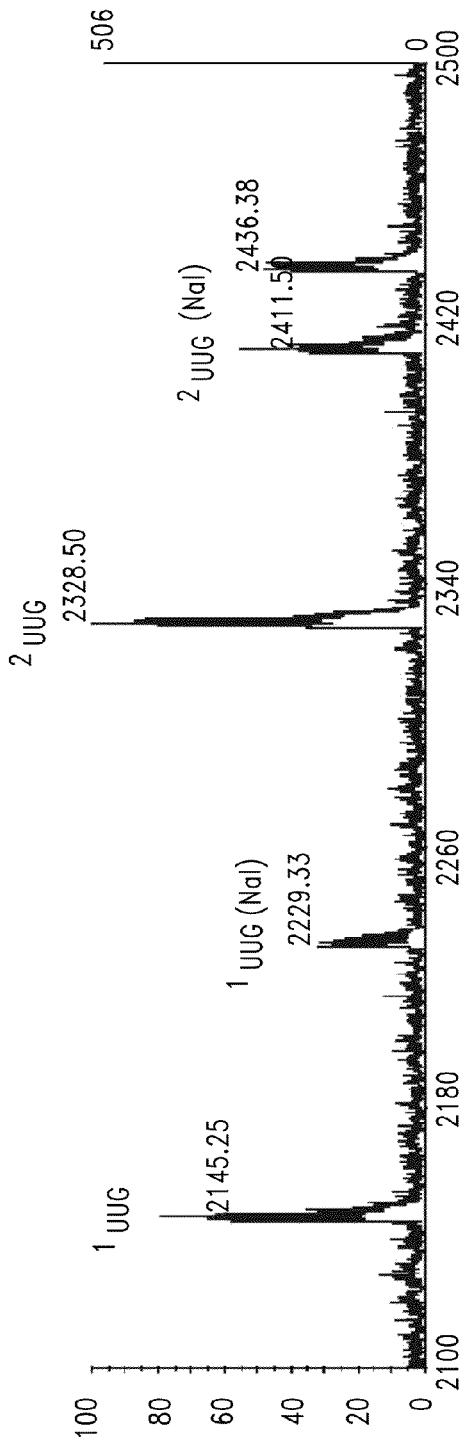
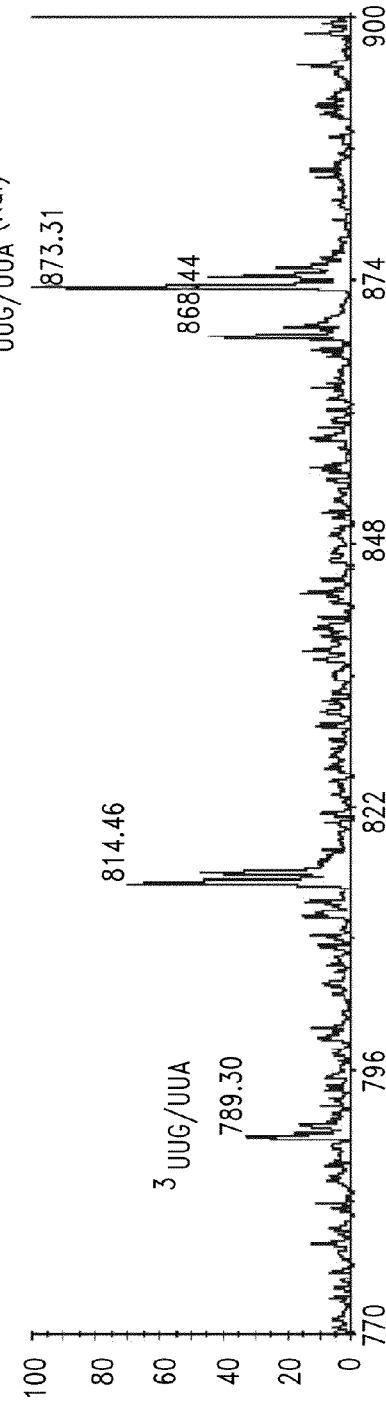
FIG. 4A
FIG. 4B

METHODS OF INCORPORATING AMINO ACID ANALOGS INTO PROTEINS

STATEMENT OF GOVERNMENT SUPPORT

This invention was made with federal government support under grant number GM62523 awarded by the NIH, and under NSF DMR-0080065 awarded by the NSF. The United States government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 110197_406C2_SEQUENCE_LISTING.txt. The text file is 2 KB, was created on Dec. 28, 2012, and is being submitted electronically via EFS-Web.

BACKGROUND OF THE INVENTION

Protein engineering is a powerful tool for modification of the structural catalytic and binding properties of natural proteins and for the de novo design of artificial proteins. Protein engineering relies on an efficient recognition mechanism for incorporating mutant amino acids in the desired protein sequences. Though this process has been very useful for designing new macromolecules with precise control of composition and architecture, a major limitation is that the mutagenesis is restricted to the 20 naturally occurring amino acids. However, it is becoming increasingly clear that incorporation of unnatural amino acids can extend the scope and impact of protein engineering methods. Thus, for many applications of designed macromolecules, it would be desirable to develop methods for incorporating amino acids that have novel chemical functionality not possessed by the 20 amino acids commonly found in naturally occurring proteins. That is, ideally, one would like to tailor changes in a protein (the size, acidity, nucleophilicity, hydrogen-bonding or hydrophobic properties, etc. of amino acids) to fulfill a specific structural or functional property of interest. The ability to incorporate such amino acid analogs into proteins would greatly expand our ability to rationally and systematically manipulate the structures of proteins, both to probe protein function and create proteins with new properties. For example, the ability to synthesize large quantities of proteins containing heavy atoms would facilitate protein structure determination, and the ability to site specifically substitute fluorophores or photo-cleavable groups into proteins in living cells would provide powerful tools for studying protein functions in vivo. One might also be able to enhance the properties of proteins by providing building blocks with new functional groups, such as an amino acid containing a keto-group.

Incorporation of novel amino acids in macromolecules has been successful to an extent. Biosynthetic assimilation of non-canonical amino acids into proteins has been achieved largely by exploiting the capacity of the wild type synthesis apparatus to utilize analogs of naturally occurring amino acids (Budisa 1995, *Eur. J. Biochem* 230: 788-796; Deming 1997, *J. Macromol. Sci. Pure Appl. Chem. A*34; 2143-2150; Duewel 1997, *Biochemistry* 36: 3404-3416; van Hest and Tirrell 1998, *FEBS Lett* 428(1-2): 68-70; Sharma et al., 2000, *FEBS Lett* 467(1): 37-40). Nevertheless, the number of amino acids shown conclusively to exhibit translational activity in vivo is small, and the chemical functionality that has been accessed by this method remains modest. In designing macromolecules with desired properties, this poses a limitation since such designs may require incorporation of complex analogs that differ significantly from the natural substrates in terms of both size and chemical properties and hence, are unable to circumvent the specificity of the synthetases. Thus, there is a need to develop a method to further expand the range of unnatural amino acids that can be incorporated.

In recent years, several laboratories have pursued an expansion in the number of genetically encoded amino acids, by using either a nonsense suppressor or a frame-shift suppressor tRNA to incorporate non-canonical amino acids into proteins in response to amber or four-base codons, respectively (Bain et al., *J. Am. Chem. Soc.* 111: 8013, 1989; Noren et al., *Science* 244: 182, 1989; Furter, *Protein Sci.* 7: 419, 1998; Wang et al., *Proc. Natl. Acad. Sci. U.S.A.,* 100: 56, 2003; Hohsaka et al., *FEBS Lett.* 344:171:1994; Kowal and Oliver, *Nucleic Acids Res.* 25: 4685, 1997). Such methods insert non-canonical amino acids at codon positions that will normally terminate wild-type peptide synthesis (e.g. a stop codon or a frame-shift mutation). These methods have worked well for single-site insertion of novel amino acids. However, their utility in multisite incorporation is limited by modest (20-60%) suppression efficiencies (Anderson et al., *J. Am. Chem. Soc.* 124: 9674, 2002; Bain et al., *Nature* 356: 537, 1992; Hohsaka et al., *Nucleic Acids Res.* 29: 3646, 2001). This is so partially because too high a stop codon suppression efficiency will interfere with the normal translation termination of some non-targeted proteins in the organism. On the other hand, a low suppression efficiency will likely be insufficient to suppress more than one nonsense or frame-shift mutation sites in the target protein, such that it becomes more and more difficult or impractical to synthesize a full-length target protein incorporating more and more non-canonical amino acids.

Efficient multisite incorporation has been accomplished by replacement of natural amino acids in auxotrophic *Escherichia coli* strains, and by using aminoacyl-tRNA synthetases with relaxed substrate specificity or attenuated editing activity (Wilson and Hatfield, *Biochim. Biophys. Acta* 781: 205, 1984; Kast and Hennecke, *J. Mol. Biol.* 222: 99, 1991; Ibba et al., *Biochemistry* 33: 7107, 1994; Sharma et al., *FEBS Lett.* 467: 37, 2000; Tang and Tirrell, *Biochemistry* 41: 10635, 2002; Datta et al., *J. Am. Chem. Soc.* 124: 5652, 2002; Doring et al., *Science* 292: 501, 2001). Although this method provides efficient incorporation of analogues at multiple sites, it suffers from the limitation that the novel amino acid must "share" codons with one of the natural amino acids. Thus for any given codon position where both natural and novel amino acids can be inserted, other than a probability of incorporation, there is relatively little control over which amino acid will end up being inserted. This may be undesirable, since for an engineered enzyme or protein, non-canonical amino acid incorporation at an unintended site may unexpectedly compromise the function of the protein, while missing incorporating the non-canonical amino acid at the designed site will fail to achieve the design goal.

The invention provides a new technique for the incorporation of non-standard/non-canonical amino acids into proteins that is based on breaking the degeneracy of the genetic code.

SUMMARY OF THE INVENTION

The present invention provides compositions of components used in protein biosynthetic machinery, which include orthogonal tRNA/aminoacyl-tRNA synthetase (AARS) pairs and the individual components of the pairs. Methods for generating and selecting orthogonal tRNAs, orthogonal aminoacyl-tRNA synthetases, and pairs thereof that can use an unnatural amino acid are also provided. Compositions of the invention include novel orthogonal tRNA/aminoacyl-tRNA synthetase pairs. The novel orthogonal pairs can be use to incorporate an unnatural amino acid in a polypeptide in vitro and in vivo. Other embodiments of the invention include selecting orthogonal pairs.

Compositions of the present invention include an orthogonal aminoacyl-tRNA synthetase (O-RS), where the O-RS preferentially aminoacylates an orthogonal tRNA (O-tRNA) with an unnatural amino acid, optionally, in vivo. In one embodiment, the invention provides a nucleic acid encoding an O-RS, or a complementary nucleic acid sequence thereof. In another embodiment, the O-RS has improved or enhanced enzymatic properties, e.g., the $K_m$ is higher or lower, the $k_{cat}$ is higher or lower, the value of $k_{cat}/K_m$ is higher or lower or the like, for the unnatural amino acid compared to a naturally occurring amino acid, e.g., one of the 20 known amino acids.

Thus one aspect of the invention relates to a polynucleotide encoding a modified tRNA of a tRNA for a natural amino acid, wherein the natural amino acid is encoded by one or more wobble degenerate codon(s), the modified tRNA comprises a modified anticodon sequence that forms Watson-Crick base-pairing with one of the wobble degenerate codon(s). Preferably, the modified tRNA is not or only inefficiently charged by an endogenous aminoacyl-tRNA synthetase (AARS) for the natural amino acid.

In certain embodiments, the modified tRNA interacts with the wobble degenerate codon with an affinity at 37° C. of at least about 1.0 kcal/mole, or 1.5 kcal/mole, or even 2.0 kcal/mole more favorably than the interaction between its unmodified version and the wobble degenerate codon.

In certain embodiments, the modified tRNA can be efficiently charged to carry an analog of the natural amino acid (e.g. the unnatural amino acid).

In certain embodiments, the unnatural amino acid is a derivative of at least one of the 20 natural amino acids, with one or more functional groups not present in natural amino acids.

In certain embodiments, the functional group is selected from the group consisting of: bromo-, iodo-, ethynyl-, cyano-, azido-, acetyl, aryl ketone, a photolabile group, a fluorescent group, and a heavy metal.

In certain embodiments, the unnatural amino acid is any one of those described herein or known in the art, such as any one in FIGS. 29, 30, and 31 of US 2003/0108885 A1 (entire content incorporated herein by reference).

In certain embodiments, the amino acid analog is a derivative of Phe, such as Nal.

In certain embodiments, the amino acid analog is a derivative of Trp, such as 6-bromo-L-tryptophan, 6-chloro-L-tryptophan, or Benzothienyl-L-alanine (Sulfur instead of Nitrogen in tryptophan).

In certain embodiments, the modified tRNA, when charged with the unnatural amino acid, can be incorporated by a translation system into a polypeptide comprising the wobble degenerate codon.

In certain embodiments, the modified AARS with relaxed substrate specificity charges the modified tRNA with the unnatural amino acid.

In certain embodiments, the specificity constant ($k_{cat}/K_M$) for activation of the unnatural amino acid by the modified AARS is at least 5-fold larger than that for the natural amino acid.

In certain embodiments, the tRNA is $tRNA^{Phe}$, the degenerate codon is UUU, and the analog is L-3-(2-naphthyl)alanine (Nal).

In certain embodiments, the modified tRNA further comprises a mutation at the fourth, extended anticodon site for increase translational efficiency.

In certain embodiments, the modified tRNA is charged by the endogenous AARS at a rate no more than 1% of that of the tRNA.

Another aspect of the invention relates to a modified tRNA encoded by any one of the subject polynucleotides, such as those described above.

Another aspect of the invention relates to a method for incorporating an unnatural amino acid into a target protein at one or more specified positions, the method comprising: (1) providing to a translation system a first polynucleotide of the subject invention or a subject modified tRNA; (2) providing to the translation system a second polynucleotide encoding a modified AARS with relaxed substrate specificity, or the modified AARS, wherein the modified AARS is capable of charging the modified tRNA with the unnatural amino acid; (3) providing to the translation system the unnatural amino acid; (4) providing a template polynucleotide encoding the target protein, wherein the codon on the template polynucleotide for the specified position(s) only forms Watson-Crick base-pairing with the modified tRNA; and, (5) allowing translation of the template polynucleotide to proceed, thereby incorporating the unnatural amino acid into the target protein at the specified position(s), wherein steps (1)-(4) are effectuated in any order.

In certain embodiments, the translation system is an in vitro translation system, such as Wheat Germ Lysate-based IVT system, an E. coli system for coupled in vitro transcription/translation; or a rabbit reticulocyte lysate-based IVT system.

In certain embodiments, the translation system is a cell.

In certain embodiments, step (3) is effectuated by contacting the cell with a solution containing the unnatural amino acid.

In certain embodiments, the unnatural amino acid is an analog of the natural amino acid.

In certain embodiments, the unnatural amino acid is an analog of at least one amino acid different from the natural amino acid.

In certain embodiments, the unnatural amino acid is not an analog of any natural amino acids.

In certain embodiments, the unnatural amino acid comprises a side-chain R group selected from: alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof.

In certain embodiments, the unnatural amino acid comprises a photoactivatable cross-linker, or is a spin-labeled amino acid, fluorescent amino acid, a metal-binding amino acid, a metal-containing amino acid, a radioactive amino acid, an amino acid with novel functional group(s), an amino acid that covalently or noncovalently interacts with other molecules, a photocaged and/or photoisomerizable amino acid, an amino acids comprising biotin or a biotin analog, a glycosylated amino acid comprising a sugar-substituted serine, a carbohydrate-modified amino acid, a keto-containing amino acid, an amino acid comprising polyethylene glycol or polyether, heavy atom-substituted amino acid, a chemically cleavable and/or photocleavable amino acid, an amino acids with an elongated side-chain as compared to natural amino acids (e.g., polyethers or long chain hydrocarbons, e.g., greater than about 5 or greater than about 10 carbons), a carbon-linked sugar-containing amino acid, a redox-active amino acid, an amino thioacid-containing amino acid, or an amino acid comprising one or more toxic moiety.

In certain embodiments, the unnatural amino acid is represented by Formula II or III:

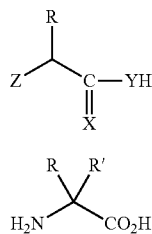

Formula II

Formula III wherein

Z comprises —OH, —NH$_2$, —SH, —NH—R', or S—R';

X and Y, which may be the same or different, comprise S or O, and

R and R', which may be the same or different, are selected from: alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydrogen, hydroxylamine, amino group, or the like or any combination thereof;

or is selected from: α-hydroxy acids, α-thioacids α-aminothiocarboxylates (e.g., with side chains corresponding to the 20 natural amino acids or unnatural side chains).

In certain embodiments, the unnatural amino acid is L, D, or α-α-disubstituted amino acid selected from D-glutamate, D-alanine, D-methyl-O-tyrosine, or aminobutyric acid.

In certain embodiments, the unnatural amino acid comprises a functional group selected from: bromo-, iodo-, ethynyl-, cyano-, azido-, acetyl, aryl ketone, photolabile, fluorescent, or heavy metal group.

In certain embodiments, the unnatural amino acid is a cyclic amino acid selected from: a 3-, 4-, 6-, 7-, 8-, and 9-membered ring proline analog; a β or γ amino acid selected from substituted β-alanine or γ-amino butyric acid.

In certain embodiments, the unnatural amino acid is a Tyrosine analog selected from: a para-substituted tyrosine, an ortho-substituted tyrosine, a meta-substituted tyrosine, wherein the substituted tyrosine comprises an acetyl group, a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, or multiply substituted aryl rings; a Glutamine analog selected from: α-hydroxy derivatives, β-substituted derivatives, cyclic derivatives, or amide-substituted glutamine derivatives; a Phenylalanine analog selected from: meta-substituted phenylalanines, wherein the substituent comprises a hydroxy group, a methoxy group, a methyl group, an allyl group, an acetyl group, or the like.

In certain embodiments, the unnatural amino acid is an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, or an isopropyl-L-phenylalanine.

In certain embodiments, the unnatural amino acid modifies one or more biological properties of a protein into which it is incorporated, the biological properties comprising: toxicity, biodistribution, solubility, thermal stability, hydrolytic stability, oxidative stability, resistance to enzymatic degradation, facility of purification and processing, structural properties, spectroscopic properties, chemical and/or photochemical properties, catalytic activity, redox potential, half-life, ability to react with other molecules either covalently or noncovalently.

In certain embodiments, the modified tRNA can be charged to carry the unnatural amino acid by the modified AARS with relaxed substrate specificity.

In certain embodiments, the specificity constant ($k_{cat}/K_M$) for activation of the unnatural amino acid by the modified AARS is at least 5-fold larger than that for the natural amino acid.

In certain embodiments, the modified tRNA is charged by an endogenous AARS at a rate no more than 1% of that of its cognate tRNA.

In certain embodiments, the unnatural amino acid is provided by introducing additional nucleic acid construct(s) into the translation system, wherein the additional nucleic acid construct(s) encode one or more proteins required for biosynthesis of the unnatural amino acid.

In certain embodiments, at least one of the additional nucleic acid construct(s) is operably linked to and subject to the control of an inducible promoter.

In certain embodiments, the first and the second polynucleotides are present on the same molecule.

In certain embodiments, the first and second polynucleotides are encoded by a plasmid or plasmids.

In certain embodiments, the plasmid or plasmids have a selectable marker.

In certain embodiments, the selectable marker is an antibiotic resistance gene.

In certain embodiments, the first polynucleotide further comprises a first promoter sequence controlling the expression of the modified tRNA.

In certain embodiments, the first promoter is an inducible promoter.

In certain embodiments, the second polynucleotide further comprises a second promoter sequence controlling the expression of the modified AARS.

In certain embodiments, the cell is auxotrophic for the natural amino acid encoded at the specified position.

In certain embodiments, the translation system lacks endogenous tRNA that forms Watson-Crick base-pairing with the codon at the specified position.

In certain embodiments, the translation system is a cell, and the method further comprises disabling one or more genes encoding any endogenous tRNA that forms Watson-Crick base-pairing with the codon at the specified position(s).

In certain embodiments, the translation system is a cell, and the method further comprises inhibiting one or more endogenous AARS that charges tRNAs that form Watson-Crick base-pairing with the codon.

In certain embodiments, the cell is a bacterial cell, such as an E. coli cell.

In certain embodiments, the cell is an insect cell.

In certain embodiments, the cell is a mammalian cell.

In certain embodiments, the cell is a fungal cell, such as a yeast cell.

In certain embodiments, the modified tRNA and/or the modified AARS are derived from a organism different from that of the cell.

In certain embodiments, the method further comprises verifying the incorporation of the analog. For example, the incorporation of the analog can be verified by mass spectrometry.

In certain embodiments, the analog is incorporated into the position at an efficiency of at least about 50%.

Another aspect of the invention provides a translation system comprising the polynucleotide of the subject invention.

In certain embodiments, the translation system further comprises a second polynucleotide encoding a modified AARS with relaxed substrate specificity, or the modified AARS, wherein the modified AARS is capable of charging the modified tRNA with an unnatural amino acid.

In certain embodiments, the translation system comprises more than two different subject polynucleotides, each of the polynucleotides capable of carrying a different unnatural amino acid.

In certain embodiments, the translation system is a cell.

In certain embodiments, the modified tRNA is from an organism different from that of the cell.

In certain embodiments, the modified tRNA is from a yeast, and the cell is an *E. coli* bacterium.

In certain embodiments, the modified AARS and the tRNA are from the same organism, and the organism is different from that of the cell.

In certain embodiments, the modified AARS and the tRNA are from a yeast, and the cell is an *E. coli* bacterium.

In certain embodiments, the expression and/or function of an endogenous tRNA homologous to the tRNA is impaired or abolished.

In certain embodiments, the expression of the endogenous tRNA is impaired/abolished by inhibiting the function of the endogenous tRNA's cognate AARS, thereby impairing/abolishing the charging of the endogenous tRNA.

In certain embodiments, the expression of the endogenous tRNA is abolished by deleting the gene encoding the endogenous tRNA.

Another aspect of the invention provides a vector comprising the subject polynucleotides.

In certain embodiments, the polynucleotide is operably linked to, and under the transcription control of a promoter.

In certain embodiments, the promoter is an inducible promoter.

In certain embodiments, the vector is an expression vector suitable for expressing the polynucleotide in a eukaryotic and/or a prokaryotic cell.

Another aspect of the invention provides a method for PEGylating a polypeptide, comprising: (1) incorporating one or more unnatural amino acid(s) at specified position(s) of the polypeptide using any of the suitable subject methods, wherein the unnatural amino acid(s) serves as site-specific PEGylations sites; (2) PEGylating the polypeptide.

In certain embodiments, the unnatural amino acid does not contain primary amine or thiol side-chain group.

In certain embodiments, the unnatural amino acid is linked to PEG moieties through a triazole linkage.

In certain embodiments, the triazole linkage is formed by copper-mediated Huisgen [3+2] cycloaddition of an azide and an alkyne.

In certain embodiments, the azide group is provided by para-azidophenylalanine, and the alkyne group is provided by an alkyne derivatized PEG reagent.

In certain embodiments, the polypeptide, when PEGylated, has one or more of: longer half life, sustained or enhanced biological activity, is homogeneously modified, increased potency and stability and/or decreased immunogenicity, consistency in biological activities from lot to lot.

Another aspect of the invention provides a PEGylated polypeptide produced by any of the subject methods.

Another aspect of the invention provides a method for enhancing half-life of a cytokine or a growth factor, comprising incorporating one or more unnatural amino acid(s) at specified position(s) of the polypeptide using any of the suitable subject methods, wherein the unnatural amino acid(s) reduces binding affinity of the cytokine or growth factor to its receptor in endosomes, thereby increasing the half-life of the cytokine or growth factor.

In certain embodiments, the unnatural amino acid changes protonation states between cell-surface and endosomal pH.

Another aspect of the invention provides a cytokine or a growth factor produced by the suitable subject methods.

Another aspect of the invention provides a method for glycosylating a polypeptide, comprising: (1) incorporating one or more unnatural amino acid(s) at specified position(s) of the polypeptide using any of the suitable subject methods, wherein the unnatural amino acid(s) serves as site-specific glycosylation site; (2) contacting the polypeptide with a saccharide moiety to form a covalent bond that attaches the saccharide moiety to the unnatural amino acid of the protein.

In certain embodiments, the unnatural amino acid comprises a first reactive group; and the saccharide moiety comprises a second reactive group, wherein the first reactive group reacts with the second reactive group in (2).

In certain embodiments, the first reactive group is an electrophilic or nucleophilic moiety, and the second reactive group is a nucleophilic or electrophilic moiety, respectively.

In certain embodiments, the electrophilic moiety is a carbonyl group, a sulfonyl group, an aldehyde group, a ketone group, a hindered ester group, a thioester group, a stable imine group, an epoxide group, or an aziridine group.

In certain embodiments, the nucleophilc moiety includes: an aliphatic or aromatic amine, ethylenediamine, —NR1-NH2 (hydrazide), —NR1(C=O)NR2NH2 (semicarbazide), —NR1(C=S)NR2NH2 (thiosemicarbazide), —(C=O)NR1NH2 (carbonylhydrazide), —(C=S)NR1NH2 (thiocarbonylhydrazide), —(SO2)NR1NH2 (sulfonylhydrazide), —NR1NR2(C=O)NR3NH2 (carbazide), NR1NR2(C=S)NR3NH2 (thiocarbazide), —O—NH2 (hydroxylamine), where each R1, R2, and R3 is independently H, or alkyl having 1-6 carbons.

In certain embodiments, the saccharide moiety includes a single carbohydrate moiety, or two or more carbohydrate moieties.

In certain embodiments, the method further comprises contacting the saccharide moiety with one or more glycosyl transferase(s), a sugar donor moiety, and other reactants required for glycosyl transferase activity for a sufficient time and under appropriate conditions to transfer a sugar from the sugar donor moiety to the saccharide moiety.

In certain embodiments, the glycosyl transferase(s) comprises one or more of: a β1-4N-acetylglucosaminyl transferase, an α1,3-fucosyl transferase, an α1,2-fucosyl transferase, an α1,4-fucosyl transferase, a β1-4-galactosyl transferase, or a sialyl transferase.

In certain embodiments, the saccharide moiety comprises a terminal GlcNAc, the sugar donor moiety is UDP-Gal, and the glycosyl transferase is a β1-4-galactosyl transferase.

In certain embodiments, the saccharide moiety comprises a terminal GlcNAc, the sugar donor moiety is UDP-GlcNAc and the glycosyl transferase is a β1-4N-acetylglucosaminyl transferase.

In certain embodiments, the first and second reactive groups produce a reaction product comprising an oxime, an amide, a hydrazone, a reduced hydrazone, a carbohydrazone, a thiocarbohydrazone, a sulfonylhydrazone, a semicarbazone, or a thiosemicarbazone.

In certain embodiments, the polypeptide is a therapeutic, diagnostic, or other protein selected from: Alpha-1 antitrypsin, Angiostatin, Antihemolytic factor, antibodies, Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, 1309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin, Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase; a transcriptional modulator that modulates cell growth, differentiation, or regulation, wherein the transcriptional modulator is from prokaryotes, viruses, or eukaryotes, including fungi, plants, yeasts, insects, and animals, including mammals; expression activator selected from cytokines, inflammatory molecules, growth factors, their receptors, oncogene products, interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; transcriptional activators and suppressors, e.g., p53, Tat, Fos, Myc, Jun, Myb, Rel; steroid hormone receptors selected from receptors for estrogen, progesterone, testosterone, aldosterone, LDL, or corticosterone; or an enzyme selected from: amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, or nucleases.

Another aspect of the invention provides a glycosylated polypeptide produced by any of the suitable subject methods.

Another aspect of the invention provides a method for generating an immunoconjugate comprising an antibody (or functional fragment/derivative thereof) and one or more therapeutic moieties, the method comprising: (1) incorporating one or more unnatural amino acid(s) at specified position(s) of the antibody using any of the suitable subject methods; (2) contacting the antibody with the one or more therapeutic moieties to form a conjugate that attaches the one or more therapeutic moieties to the unnatural amino acid(s) of the antibody.

In certain embodiments, the therapeutic moieties are different.

In certain embodiments, the therapeutic moieties are conjugated to the same unnatural amino acids.

In certain embodiments, the therapeutic moieties are conjugated to different unnatural amino acids.

In certain embodiments, the therapeutic moieties are cleavable under one or more conditions selected from: mild or weak acidic conditions (e.g., about pH 4-6, preferably about pH5), reductive environment (e.g., the presence of a reducing agent), divalent cations, or (optionally) heat.

Another aspect of the invention provides an immunoconjugate produced by any of the suitable subject methods.

Another aspect of the invention provides a method for immobilizing one or more polypeptide(s) to an array, the method comprising: (1) incorporating one or more unnatural amino acid(s) at specified position(s) of the polypeptide(s) using any of the suitable methods; (2) contacting the polypeptide(s) with a solid support to conjugate the polypeptide(s) through the unnatural amino acid(s).

In certain embodiments, the one or more polypeptides are attached to the solid support in a consistent orientation.

In certain embodiments, the active site(s) of each polypeptide(s) are accessible to potentially interacting molecules.

Another aspect of the invention provides a polypeptide array produced by any of the suitable subject methods.

All embodiments described above and those in other parts of the specification are contemplated to be able to freely combine with one or more other embodiments, even for those embodiments described under separate aspects of the invention, unless such combinations are specifically excluded or would contradict the general principles and/or teachings of the instant specification.

BRIEF DESCRIPTION OF THE FIGURES

FIGS. 4A-D demonstrates the replacement of Leu by Nal as detected in MALDI mass spectra of tryptic fragments of mDHFR.

DETAILED DESCRIPTION OF THE INVENTION

I. Overview

Figure 1:
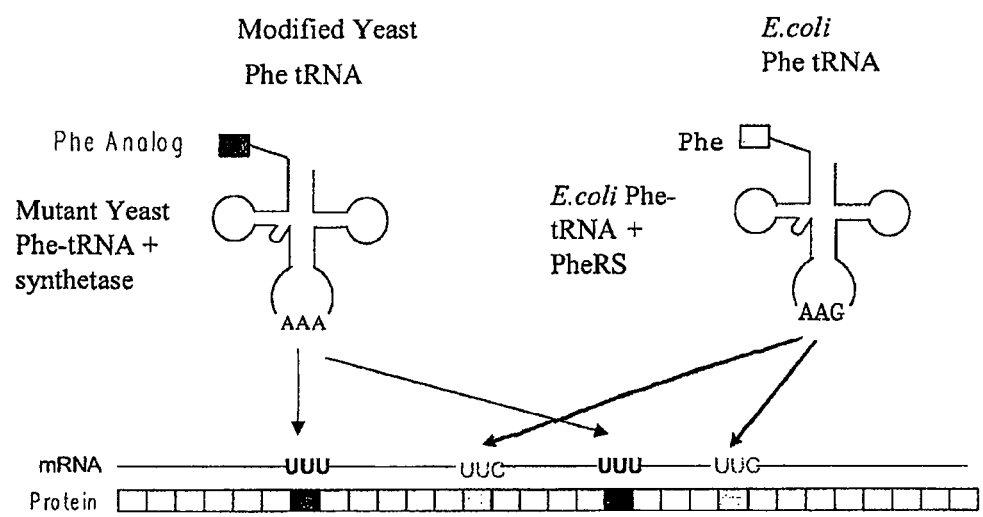
FIG. 1 shows a schematic diagram for multiple-site-specific incorporation of unnatural amino acid into the UUU codon.

Proteins are at the crossroads of virtually every biological process, from photosynthesis and vision to signal transduction and the immune response. These complex functions result from a polyamide based polymer consisting of twenty relatively simple building blocks arranged in a defined primary sequence.

The present invention includes methods and composition for use in the site-specific incorporation of unnatural amino acids directly into proteins in vivo. Importantly, the unnatural amino acid is added to the genetic repertoire, rather than substituting for one of the common 20 amino acids. The present invention provides methods for generating, methods for identifying and compositions comprising the components used by the biosynthetic machinery to incorporate an unnatural amino acid into a protein.

The present invention, e.g., (i) allows the site-selective insertion of one or more unnatural amino acids at any desired position of any protein, (ii) is applicable to both prokaryotic and eukaryotic cells, (iii) enables in vivo studies of mutant proteins in addition to the generation of large quantities of purified mutant proteins, and (iv) is adaptable to incorporate any of a large variety of unnatural amino acids, into proteins in vivo. Thus, in a specific polypeptide sequence a number of different site-selective insertions of unnatural amino acids is possible. Such insertions are optionally all of the same type (e.g., multiple examples of one type of unnatural amino acid inserted at multiple points in a polypeptide) or are optionally of diverse types (e.g., different unnatural amino acid types are inserted at multiple points in a polypeptide).

The invention provides methods and reagents for incorporating amino acid analogs into a target protein. The modified target proteins thus produced are useful for discovery of potentially useful therapeutic molecules, biomaterials, and other proteins of interest. Such proteins also are useful for functional and structural studies of proteins as well as for biochemical study of the translation system.

One aspect of the invention provides a polynucleotide encoding a modified tRNA based on a wild-type tRNA for a natural amino acid.

In certain embodiments, the natural amino acid is encoded by two or more genetic codes (thus encoded by degenerate genetic codes). In most, if not all cases, this includes 18 of the 20 natural amino acids, except Met and Trp. In these circumstances, to recognize all the degenerate genetic codes for the natural amino acid, the anticodon loop of the wild-type tRNA(s) relies on both wobble base-pairing and pure Watson-Crick base-pairing. The subject modified tRNA contains at least one modification in its anticodon loop, such that the modified anticodon loop now forms Watson-Crick base-pairing to one of the degenerate genetic codes, which the tRNA previously bind only through wobble base-pairing (see Example I below).

Since Watson-Crick base pairing is invariably stronger and more stable than wobble base pairing, the subject modified tRNA will preferentially bind to a previous wobble base-pairing genetic code (now through Watson-Crick base-pairing), over a previous Watson-Crick base-pairing (now through wobble base-pairing). Thus an analog may be incorporated at the subject codon, if the modified tRNA is charged with an analog of a natural amino acid, which may or may not be the same as the natural amino acid encoded by the codon in question.

For example, in Example II below, some Phe in mouse DHFR (mDHFR) are encoded by UUC codons, some others by UUU codons. The wild-type E. coli tRNA for Phe has a GAA anticodon sequence, and thus binds the UUC codons through Watson-Crick base-pairing, and binds the UUU codons through wobble base-pairing. Thus in E. coli, a modified tRNA, such as a yeast tRNA for Phe may have a modified anticodon sequence of AAA, so that it now preferentially binds to the previously "disfavored" UUU codons. When such a modified Phe tRNA is charged with Nal, it competes with the wild-type Phe tRNA charged with Phe for the UUU codon. But since the modified tRNA binds UUU through the stronger Watson-Crick base-pairing, Nal (rather than Phe) will be preferentially, if not exclusively, inserted in the UUU codons.

In fact, the anticodon sequence of the modified tRNA may be changed in such a way that it now recognizes a codon for a different natural amino acid. For example, in Example III, the Phe tRNA anticodon sequence is changed from GAA to CAA, which is capable of Watson-Crick base-pairing with a Leu (rather than a Phe) codon UUG. Such a modified Phe tRNA can now incorporate Nal into certain Leu codons.

Thus in certain embodiments, if it is desirable to incorporate certain amino acid analogs at codons for Met or Trp, a tRNA for a natural amino acid (e.g., a Met tRNA, a Trp tRNA, or even a Phe tRNA, etc.) may be modified to recognize the Met or Trp codon. Under this type of unique situation, both the modified tRNA and the natural tRNA compete to bind the same (single) genetic code through Watson-Crick base-pairing. Some but not all such codons will accept their natural amino acids, while others may accept amino acid analogs carried by the modified tRNA. Other factors, such as the abundance of the natural amino acid vs. that of the analog, may affect the final outcome.

This also applies to other situations where a modified tRNA competes with wild-type tRNA for any natural amino acids. Such modified tRNAs are within the scope of the instant invention.

In certain preferred embodiments, the modified tRNA is not charged or only inefficiently charged by an endogenous aminoacyl-tRNA synthetase (AARS) for any natural amino acid, such that the modified tRNA largely (if not exclusively) carries an amino acid analog, but not a natural amino acid. Although a subject modified tRNA may still be useful if it can be charged by the endogenous AARS with a natural amino acid.

In certain embodiments, the modified tRNA charged with an amino acid analog has such an overall shape and size that the analog-tRNA is a ribosomally acceptable complex, that is, the tRNA-analog complex can be accepted by the prokaryotic or eukaryotic ribosomes in an in vivo or in vitro translation system.

In certain embodiments, the modified tRNA can be efficiently charged to carry an analog of a natural amino acid. The amino acid analog may be a derivative of at least one of the 20 natural amino acids, with one or more functional groups not present in natural amino acids. For example, the functional group may be selected from the group consisting of: bromo-, iodo-, ethynyl-, cyano-, azido-, acetyl, aryl ketone, a photolabile group, a fluorescent group, and a heavy metal.

In one embodiment, the amino acid analog is a derivative of Phe, such as Nal.

In certain embodiments, the modified tRNA can be charged to carry the analog by a modified AARS with relaxed substrate specificity.

Preferably, the modified AARS specifically or preferentially charges the analog to the modified tRNA over any natural amino acid. In a preferred embodiment, the specificity constant for activation of the analog by the modified AARS (defined as $k_{cat}/K_M$) is at least about 2-fold larger than that for the natural amino acid, preferably about 3-fold, 4-fold, 5-fold or more than that for the natural amino acid.

In a preferred embodiment, the tRNA is $tRNA^{Phe}$, the degenerate codon is UUU, and the analog is L-3-(2-naphthyl)alanine (Nal).

In certain embodiments, the modified tRNA further comprises a mutation at the fourth, extended anticodon site for increase translational efficiency.

In certain embodiments, the modified tRNA is charged by the endogenous AARS at a rate no more than about 50%, 30%, 20%, 10%, 5%, 2%, or 1% of that of the tRNA.

Another aspect of the invention provides a modified tRNA encoded by any one of the subject polynucleotides.

Another aspect of the invention provides a method for incorporating an amino acid analog into a target protein at one or more specified positions, the method comprising: (1) providing to an environment a first subject polynucleotide for a modified tRNA, or a subject modified tRNA; (2) providing to the environment a second subject polynucleotide encoding a modified AARS with relaxed substrate specificity, or the modified AARS, wherein the modified AARS is capable of charging the modified tRNA with the analog; (3) providing to the environment the analog; (4) providing a template polynucleotide encoding the target protein, wherein the codon on the template polynucleotide for the specified position only forms Watson-Crick base-pairing with the modified tRNA; and, (5) allowing translation of the template polynucleotide to proceed, thereby incorporating the analog into the target protein at the specified position, wherein steps (1)-(4) are effectuated in any order.

In certain embodiments, the methods of the invention involve introducing into an environment (e.g., a cell or an in vitro translation system (IVT)) a first nucleic acid encoding an orthogonal/modified tRNA molecule that is not charged efficiently by an endogenous aminoacyl-tRNA synthetase in the cell/in vitro translation system (IVT), or the orthogonal/modified tRNA itself. The orthogonal/modified tRNA molecule has an anticodon complementary to a degenerate codon sequence, which is one of a plurality of codon sequences encoding a naturally occurring amino acid. Such a codon is said to be degenerate. According to the methods of this embodiment of the invention, a second nucleic acid encoding an orthogonal/modified aminoacyl tRNA synthetase (AARS) is also introduced into the cell/IVT. The orthogonal/modified AARS is capable of charging the orthogonal/modified tRNA with a chosen amino acid analog. The amino acid analog can then be provided to the cell so that it can be incorporated into one or more proteins within the cell or IVT.

Thus in certain embodiments, the environment is an in vitro translation system. For example, suitable IVT systems include the Wheat Germ Lysate-based PROTEINscript-PRO™, Ambion's E. coli system for coupled in vitro transcription/translation; or the rabbit reticulocyte lysate-based Retic Lysate IVT™ Kit from Ambion). Optionally, the in vitro translation system can be selectively depleted of one or more natural AARSs (by, for example, immunodepletion using immobilized antibodies against natural AARS) and/or natural amino acids so that enhanced incorporation of the analog can be achieved. Alternatively, nucleic acids encoding the re-designed AARSs may be supplied in place of recombinantly produced AARSs. The in vitro translation system is also supplied with the analogs to be incorporated into mature protein products.

In other embodiments, the environment is a cell. A variety of cells (or lysates thereof suitable for IVT) can be used in the methods of the invention, including, for example, a bacterial cell, a fungal cell, an insect cell, and a mammalian cell (e.g. a human cell or a non-human mammal cell). In one embodiment, the cell is an E. coli cell.

In certain embodiments, the amino acid analog can be provided by directly contacting the cell or IVT with the analog, for example, by applying a solution of the analog to the cell in culture, or by directly adding the analog to the IVT. The analog can also be provided by introducing one or more additional nucleic acid construct(s) into the cell/IVT, wherein the additional nucleic acid construct(s) encodes one or more amino acid analog synthesis proteins that are necessary for synthesis of the desired analog.

In certain embodiments, the additional nucleic acid construct(s) has an inducible promoter sequence that can induce expression of the one or more synthesis proteins.

The methods of this embodiment of the invention further involve introducing a template nucleic acid construct into the cell/IVT, the template encoding a protein, wherein the nucleic acid construct contains at least one degenerate codon sequence.

The nucleic acids introduced into the cell/IVT can be introduced as one construct or as a plurality of constructs. In certain embodiments, the various nucleic acids are included in the same construct. For example, the nucleic acids can be introduced in any suitable vectors capable of expressing the encoded tRNA and/or proteins in the cell/IVT. In one embodiment, the first and second nucleic acid sequences are provided in one or more plasmids. In another embodiment, the vector or vectors used are viral vectors, including, for example, adenoviral and lentiviral vectors. The sequences can be introduced with an appropriate promoter sequence for the cell/IVT, or multiple sequences that can be inducible for controlling the expression of the sequences.

In certain embodiments, the plasmid or plasmids containing the subject polynucleotides have one or more selectable markers, such as antibiotic resistance genes.

In certain embodiments, the first polynucleotide further comprises a first promoter sequence controlling the expression of the modified tRNA. The first promoter is an inducible promoter.

In certain embodiments, the second polynucleotide further comprises a second promoter sequence controlling the expression of the modified AARS.

In certain embodiments, the cell is auxotrophic for the amino acid naturally encoded by the degenerate codon.

In certain embodiments, the cell is auxotrophic for the natural amino acid encoded at the specified position.

In certain embodiments, the environment lacks endogenous tRNA that forms Watson-Crick base-pairing with the codon at the specified position.

When the cell has a tRNA that has an anticodon perfectly complementary to the degenerate codon, the methods can include a step of disabling the gene encoding such an endogenous tRNA.

Alternatively, the environment is a cell, and the method further comprises inhibiting one or more endogenous AARS that charges tRNAs that form Watson-Crick base-pairing with the codon.

In certain embodiments, the orthogonal tRNA and orthogonal aminoacyl tRNA-synthetase can be derived from an organism from a different species than that of the cell/the IVT. For example, a yeast tRNA and a yeast AARS may be used with an *E. coli* cell.

In certain embodiments, the method further comprises verifying the incorporation of the analog by, for example, mass spectrometry.

In certain embodiments, the method incorporates the analog into the position at an efficiency of at least about 50%, or 60%, 70%, 80%, 90%, 95%, 99% or nearly 100%.

II. Definitions

Before describing the present invention in detail, it is to be understood that this invention is not limited to particular compositions or biological systems, which can, of course, vary. It is also to be understood that the terminology used herein is for the purpose of describing particular illustrative embodiments only, and is not intended to be limiting. As used in this specification and the appended claims, the singular forms "a," "an," and "the" include plural referents unless the content clearly dictates otherwise. Thus, for example, reference to "a molecule" optionally includes a combination of two or more such molecules, and the like.

Unless specifically defined below, the terms used in this specification generally have their ordinary meanings in the art, within the general context of this invention and in the specific context where each term is used. Certain terms are discussed below or elsewhere in the specification, to provide additional guidance to the practitioner in describing the compositions and methods of the invention and how to make and use them. The scope an meaning of any use of a term will be apparent from the specific context in which the term is used.

"About" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

"Amino acid analog," "non-canonical amino acid," or "non-standard amino acid," used interchangeably, is meant to include all amino acid-like compounds that are similar in structure and/or overall shape to one or more of the twenty L-amino acids commonly found in naturally occurring proteins (Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y, as defined and listed in WIPO Standard ST.25 (1998), Appendix 2, Table 3). Amino acid analog can also be natural amino acids with modified side chains or backbones. Preferably, these analogs usually are not "substrates" for the amino acyl tRNA synthethases (AARSs) because of the normally high specificity of the AARSs. Although occasionally, certain analogs with structures/shapes sufficiently close to those of natural amino acids may be erroneously incorporated into proteins by AARSs, especially modified AARSs with relaxed substrate specificity. In a preferred embodiment, the analogs share backbone structures, and/or even the most side chain structures of one or more natural amino acids, with the only difference(s) being containing one or more modified groups in the molecule. Such modification may include, without limitation, substitution of an atom (such as N) for a related atom (such as S), addition of a group (such as methyl, or hydroxyl group, etc.) or an atom (such as Cl or Br, etc.), deletion of a group (supra), substitution of a covalent bond (single bond for double bond, etc.), or combinations thereof. Amino acid analogs may include α-hydroxy acids, and β-amino acids, and can also be referred to as "modified amino acids," or "unnatural AARS substrates."

The amino acid analogs may either be naturally occurring or unnaturally occurring (e.g. synthesized). As will be appreciated by those in the art, any structure for which a set of rotamers is known or can be generated can be used as an amino acid analog. The side chains may be in either the (R) or the (S) configuration (or D- or L-configuration). In a preferred embodiment, the amino acids are in the (S) or L-configuration.

Preferably, the overall shape and size of the amino acid analogs are such that, upon being charged to (natural or re-designed) tRNAs by (natural or re-designed) AARS, the analog-tRNA is a ribosomally accepted complex, i.e., the tRNA-analog complex can be accepted by the prokaryotic or eukaryotic ribosomes in an in vivo or in vitro translation system.

"Achor residues" are residue positions in AARS that maintain critical interactions between the AARS and the natural amino acid backbone.

"Backbone," or "template" includes the backbone atoms and any fixed side chains (such as the anchor residue side chains) of the protein (e.g., AARS). For calculation purposes, the backbone of an analog is treated as part of the AARS backbone.

"Protein backbone structure" or grammatical equivalents herein is meant the three dimensional coordinates that define the three dimensional structure of a particular protein. The structures which comprise a protein backbone structure (of a naturally occurring protein) are the nitrogen, the carbonyl carbon, the α-carbon, and the carbonyl oxygen, along with the direction of the vector from the α-carbon to the β-carbon.

The protein backbone structure which is input into the computer can either include the coordinates for both the backbone and the amino acid side chains, or just the backbone, i.e. with the coordinates for the amino acid side chains removed. If the former is done, the side chain atoms of each amino acid of the protein structure may be "stripped" or removed from the structure of a protein, as is known in the art, leaving only the coordinates for the "backbone" atoms (the nitrogen, carbonyl carbon and oxygen, and the α-carbon, and the hydrogens attached to the nitrogen and α-carbon).

Optionally, the protein backbone structure may be altered prior to the analysis outlined below. In this embodiment, the representation of the starting protein backbone structure is reduced to a description of the spatial arrangement of its secondary structural elements. The relative positions of the secondary structural elements are defined by a set of parameters called supersecondary structure parameters. These parameters are assigned values that can be systematically or randomly varied to alter the arrangement of the secondary structure elements to introduce explicit backbone flexibility. The atomic coordinates of the backbone are then changed to reflect the altered supersecondary structural parameters, and these new coordinates are input into the system for use in the subsequent protein design automation. For details, see U.S. Pat. No. 6,269,312, the entire content incorporated herein by reference.

"Conformational energy" refers generally to the energy associated with a particular "conformation", or three-dimensional structure, of a macromolecule, such as the energy associated with the conformation of a particular protein.

Interactions that tend to stabilize a protein have energies that are represented as negative energy values, whereas interactions that destabilize a protein have positive energy values. Thus, the conformational energy for any stable protein is quantitatively represented by a negative conformational energy value. Generally, the conformational energy for a particular protein will be related to that protein's stability. In particular, molecules that have a lower (i.e., more negative) conformational energy are typically more stable, e.g., at higher temperatures (i.e., they have greater "thermal stability"). Accordingly, the conformational energy of a protein may also be referred to as the "stabilization energy."

Typically, the conformational energy is calculated using an energy "force-field" that calculates or estimates the energy contribution from various interactions which depend upon the conformation of a molecule. The force-field is comprised of terms that include the conformational energy of the alpha-carbon backbone, side chain-backbone interactions, and side chain-side chain interactions. Typically, interactions with the backbone or side chain include terms for bond rotation, bond torsion, and bond length. The backbone-side chain and side chain-side chain interactions include van der Waals interactions, hydrogen-bonding, electrostatics and solvation terms. Electrostatic interactions may include coulombic interactions, dipole interactions and quadrapole interactions). Other similar terms may also be included. Force-fields that may be used to determine the conformational energy for a polymer are well known in the art and include the CHARMM (see, Brooks et al, J. Comp. Chem. 1983, 4:187-217; MacKerell et al., in The Encyclopedia of Computational Chemistry, Vol. 1:271-277, John Wiley & Sons, Chichester, 1998), AMBER (see, Cornell et al., J. Amer. Chem. Soc. 1995, 117:5179; Woods et al., J. Phys. Chem. 1995, 99:3832-3846; Weiner et al., J. Comp. Chem. 1986, 7:230; and Weiner et al., J. Amer. Chem. Soc. 1984, 106:765) and DREIDING (Mayo et al., J. Phys. Chem. 1990, 94-:8897) force-fields, to name but a few.

In a preferred implementation, the hydrogen bonding and electrostatics terms are as described in Dahiyat & Mayo, Science 1997 278:82). The force field can also be described to include atomic conformational terms (bond angles, bond lengths, torsions), as in other references. See e.g., Nielsen J E, Andersen K V, Honig B, Hooft R W W, Klebe G, Vriend G, & Wade R C, "Improving macromolecular electrostatics calculations," Protein Engineering, 12: 657662 (1999); Stikoff D, Lockhart D J, Sharp K A & Honig B, "Calculation of electrostatic effects at the amino-terminus of an alpha-helix," Biophys. J., 67: 2251-2260 (1994); Hendscb Z S, Tidor B, "Do salt bridges stabilize proteins—a continuum electrostatic analysis," Protein Science, 3: 211-226 (1994); Schneider J P, Lear J D, DeGrado W F, "A designed buried salt bridge in a heterodimeric coil," J. Am. Chem. Soc., 119: 5742-5743 (1997); Sidelar C V, Hendsch Z S, Tidor B, "Effects of salt bridges on protein structure and design," Protein Science, 7: 1898-1914 (1998). Solvation terms could also be included. See e.g., Jackson S E, Moracci M, elMastry N, Johnson C M, Fersht A R, "Effect of Cavity-Creating Mutations in the Hydrophobic Core of Chymotrypsin Inhibitor 2," Biochemistry, 32: 11259-11269 (1993); Eisenberg, D & McLachlan A D, "Solvation Energy in Protein Folding and Binding," Nature, 319: 199-203 (1986); Street A G & Mayo S L, "Pairwise Calculation of Protein Solvent-Accessible Surface Areas," Folding & Design, 3: 253-258 (1998); Eisenberg D & Wesson L, "Atomic solvation parameters applied to molecular dynamics of proteins in solution," Protein Science, 1: 227-235 (1992); Gordon & Mayo, supra.

"Coupled residues" are residues in a molecule that interact, through any mechanism. The interaction between the two residues is therefore referred to as a "coupling interaction." Coupled residues generally contribute to polymer fitness through the coupling interaction. Typically, the coupling interaction is a physical or chemical interaction, such as an electrostatic interaction, a van der Waals interaction, a hydrogen bonding interaction, or a combination thereof. As a result of the coupling interaction, changing the identity of either residue will affect the "fitness" of the molecule, particularly if the change disrupts the coupling interaction between the two residues. Coupling interaction may also be described by a distance parameter between residues in a molecule. If the residues are within a certain cutoff distance, they are considered interacting.

"Fitness" is used to denote the level or degree to which a particular property or a particular combination of properties for a molecule, e.g., a protein, are optimized. In certain embodiments of the invention, the fitness of a protein is preferably determined by properties which a user wishes to improve. Thus, for example, the fitness of a protein may refer to the protein's thermal stability, catalytic activity, binding affinity, solubility (e.g., in aqueous or organic solvent), and the like. Other examples of fitness properties include enantioselectivity, activity towards unnatural substrates, and alternative catalytic mechanisms. Coupling interactions can be modeled as a way of evaluating or predicting fitness (stability). Fitness can be determined or evaluated experimentally or theoretically, e.g. computationally.

Preferably, the fitness is quantitated so that each molecule, e.g., each amino acid will have a particular "fitness value". For example, the fitness of a protein may be the rate at which the protein catalyzes a particular chemical reaction, or the protein's binding affinity for a ligand. In a particularly preferred embodiment, the fitness of a protein refers to the conformational energy of the polymer and is calculated, e.g., using any method known in the art. See, e.g. Brooks B. R., Bruccoleri R E, Olafson, B D, States D J, Swaminathan S & Karplus M, "CHARMM: A Program for Macromolecular Energy, Minimization, and Dynamics Calculations," J. Comp. Chem., 4: 187-217 (1983); Mayo S L, Olafson B D & Goddard W A G, "DREIDING: A Generic Force Field for Molecular Simulations," J. Phys. Chem., 94: 8897-8909 (1990); Pabo C 0 & Suchanek E G, "Computer-Aided Model-Building Strategies for Protein Design," Biochemistry, 25: 5987-5991 (1986), Lazar G A, Desjarlais J R & Handel T M, "De Novo Design of the Hydrophobic Core of Ubiquitin," Protein Science, 6: 1167-1178 (1997); Lee C & Levitt M, "Accurate Prediction of the Stability and Activity Effects of Site Directed Mutagenesis on a Protein Core," Nature, 352: 448-451 (1991); Colombo G & Merz K M, "Stability and Activity of Mesophilic Subtilisin E and Its Thermophilic Homolog: Insights from Molecular Dynamics Simulations," J. Am. Chem. Soc., 121: 6895-6903 (1999); Weiner S J, Kollman P A, Case D A, Singh U C, Ghio C, Alagona G, Profeta S J, Weiner P, "A new force field for molecular mechanical simulation of nucleic acids and proteins," J. Am. Chem. Soc., 106: 765-784 (1984). Generally, the fitness of a protein is quantitated so that the fitness value increases as the property or combination of properties is optimized. For example, in embodiments where the thermal stability of a protein is to be optimized (conformational energy is preferably decreased), the fitness value may be the negative conformationl energy; i.e., $F=-E$.

The "fitness contribution" of a protein residue refers to the level or extent $f(i_a)$ to which the residue $i_a$, having an identity a, contributes to the total fitness of the protein. Thus, for example, if changing or mutating a particular amino acid residue will greatly decrease the protein's fitness, that residue is said to have a high fitness contribution to the polymer. By contrast, typically some residues $i_a$ in a protein may have a variety of possible identities a without affecting the protein's fitness. Such residues, therefore have a low contribution to the protein fitness.

"Dead-end elimination" (DEE) is a deterministic search algorithm that seeks to systematically eliminate bad rotamers and combinations of rotamers until a single solution remains. For example, amino acid residues can be modeled as rotamers that interact with a fixed backbone. The theoretical basis for DEE provides that, if the DEE search converges, the solution is the global minimum energy conformation (GMEC) with no uncertainty (Desmet et al., 1992).

Dead end elimination is based on the following concept. Consider two rotamers, $i_r$ and $i_t$, at residue i, and the set of all other rotamer configurations $\{S\}$ at all residues excluding i (of which rotamer $j_s$ is a member). If the pairwise energy contributed between $i_t$ and $j_s$ is higher than the pairwise energy between $i_t$ and $j_s$ for all $\{S\}$, then rotamer $i_t$ cannot exist in the global minimum energy conformation, and can be eliminated. This notion is expressed mathematically by the inequality.

$$E(i_r) + \sum_{j \neq i}^{N} E(i_r, j_s) > E(i_t) + \sum_{j \neq i}^{N} E(i_t, j_s)\{S\} \quad \text{(Equation A)}$$

If this expression is true, the single rotamer $i_t$ can be eliminated (Desmet et al., 1992).

In this form, Equation A is not computationally tractable because, to make an elimination, it is required that the entire sequence (rotamer) space be enumerated. To simplify the problem, bounds implied by Equation A can be utilized:

$$E(i_r) + \sum_{j \neq i}^{N} \min(s)E(i_r, j_s) > E(i_t) + \sum_{j \neq i}^{N} \max(s)E(i_t, j_s)\{S\} \quad \text{(Equation B)}$$

Using an analogous argument, Equation B can be extended to the elimination of pairs of rotamers inconsistent with the GMEC. This is done by determining that a pair of rotamers $i_r$ at residue i and $j_s$ at residue j, always contribute higher energies than rotamers $i_u$ and $j_v$ with all possible rotamer combinations $\{L\}$. Similar to Equation B, the strict bound of this statement is given by:

$$\varepsilon(i_r, j_s) + \sum_{k \neq i,j}^{N} \min(t)\varepsilon(i_r, j_s, k_t) > \quad \text{(Equation C)}$$

$$\varepsilon(i_u, j_v) + \sum_{k \neq i,j}^{N} \max(t)\varepsilon(i_u, j_v, k_i)$$

where $\epsilon$ is the combined energies for rotamer pairs $$\epsilon(i_r,j_s)=E(i_r)+E(j_s)+E(i_r,j_s) \quad \text{(Equation D)},$$

and $$\epsilon(i_r,j_s,k_t)=E(i_r,k_t)+E(j_s,k_t) \quad \text{(Equation E)}.$$

This leads to the doubles elimination of the pair of rotamers $i_r$ and $j_s$, but does not eliminate the individual rotamers completely as either could exist independently in the GMEC. The doubles elimination step reduces the number of possible pairs (reduces S) that need to be evaluated in the right-hand side of Equation 6, allowing more rotamers to be individually eliminated.

The singles and doubles criteria presented by Desmet et al. fail to discover special conditions that lead to the determination of more dead-ending rotamers For instance, it is possible that the energy contribution of rotamer $i_t$ is always lower than $i_r$ without the maximum of $i_t$ being below the minimum of $i_r$. To address this problem, Goldstein 1994 presented a modification of the criteria that determines if the energy profiles of two rotamers cross. If they do not, the higher energy rotamer can be determined to be dead-ending. The doubles calculation significantly more computational time than the singles calculation. To accelerate the process, other computational methods have been developed to predict the doubles calculations that will be the most productive (Gordon & Mayo, 1998). These kinds of modifications, collectively referred to as fast doubles, significantly improved the speed and effectiveness of DEE.

Several other modifications also enhance DEE. Rotamers from multiple residues can be combined into so-called superrotamers to prompt further eliminations (Desmet et al., 1994; Goldstein, 1994). This has the advantage of eliminating multiple rotamers in a single step. In addition, it has been shown that "splitting" the conformational space between rotamers improves the efficiency of DEE (Pierce et al., 2000). Splitting handles the following special case. Consider rotamer $i_r$. If a rotamer $i_{r2}$ contributes a lower energy than $i_r$ for a portion of the conformational space, and a rotamer $i_{r2}$ has a lower energy than $i_r$ for the remaining fraction, then $i_r$ can be eliminated. This case would not be detected by the less sensitive Desmet or Goldstein criteria. In the preferred implementations of the invention as described herein, all of the described enhancements to DEE were used.

For further discussion of these methods see, Goldstein, R. F. (1994), Efficient rotamer elimination applied to protein side-chains and related spin glasses, *Biophysical Journal* 66, 1335-1340; Desmet, J., De Maeyer, M., Hazes, B. & Lasters, I. (1992), The dead-end elimination theorem and its use in protein side-chain positioning. *Nature* 356, 539-542; Desmet, J., De Maeyer, M. & Lasters, I. (1994), In *The Protein Folding Problem and Tertiary Structure Prediction* (Jr., K. M. & Grand, S. L., eds.), pp. 307-337 (Birkhauser, Boston); De Maeyer, M., Desmet, J. & Lasters, I. (1997), All in one: a highly detailed rotamer library improves both accuracy and speed in the modeling of side chains by dead-end elimination, *Folding & Design* 2, 53-66, Gordon, D. B. & Mayo, S. L. (1998), Radical performance enhancements for combinatorial optimization algorithms based on the dead-end elimination theorem, *Journal of Computational Chemistry* 19, 1505-1514; Pierce, N. A., Spriet, J. A., Desmet, J., Mayo, S. L., (2000), Conformational splitting: A more powerful criterion for dead-end elimination; *Journal of Computational Chemistry* 21, 999-1009.

"Expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells such as Sf9, Hi5 or S2 cells and Baculovirus vectors, *Drosophila* cells (Schneider cells) and expression systems, and mammalian host cells and vectors.

"Host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells may be cultured in vitro or one or more cells in a non-human animal (e.g., a transgenic animal or a transiently transfected animal).

The methods of the invention may include steps of comparing sequences to each other, including wild-type sequence to one or more mutants. Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, "-", or "Δ") in the polymer sequence not containing the inserted or deleted residue.

"Homologous", in all its grammatical forms and spelling variations, refers to the relationship between two molecules (e.g. proteins, tRNAs, nucleic acids) that possess a "common evolutionary origin", including proteins from superfamilies in the same species of organism, as well as homologous proteins from different species of organism. Such proteins (and their encoding nucleic acids) have sequence and/or structural homology, as reflected by their sequence similarity, whether in terms of percent identity or by the presence of specific residues or motifs and conserved positions. Homologous molecules frequently also share similar or even identical functions.

The term "sequence similarity", in all its grammatical forms, refers to the degree of identity or correspondence between nucleic acid or amino acid sequences that may or may not share a common evolutionary origin (see, Reeck et al., supra). However, in common usage and in the instant application, the term "homologous", when modified with an adverb such as "highly", may refer to sequence similarity and may or may not relate to a common evolutionary origin.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., *Molecular Cloning: A Laboratory Manual*, Second Edition (1989) Cold Spring Harbor Laboratory Press, Cold Spring Harbor, N.Y.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

Unless specified, the term "standard hybridization conditions" refers to a $T_m$ of about 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligoncucleotide molecules used. Exemplary temperatures may be 37° C. (for 14-base oligonucleotides), 48° C. (for 17-base oligoncucleotides), 55° C. (for 20-base oligonucleotides) and 60° C. (for 23-base oligonucleotides). Exemplary suitable hybridization conditions for oligonucleotides include washing in 6×SSC/0.05% sodium pyrophosphate, or other conditions that afford equivalent levels of hybridization.

"Polypeptide," "peptide" or "protein" are used interchangably to describe a chain of amino acids that are linked together by chemical bonds called "peptide bonds." A protein or polypeptide, including an enzyme, may be a "native" or "wild-type", meaning that it occurs in nature; or it may be a "mutant", "variant" or "modified", meaning that it has been made, altered, derived, or is in some way different or changed from a native protein or from another mutant.

"Rotamer" is defined as a set of possible conformers for each amino acid or analog side chain. See Ponder, et al., Acad. Press Inc. (London) Ltd. pp. 775-791 (1987); Dunbrack, et al., Struc. Biol. 1(5):334-340 (1994); Desmet, et al., Nature 356:539-542 (1992). A "rotamer library" is a collection of a set of possible/allowable rotametic conformations for a given set of amino acids or analogs. There are two general types of rotamer libraries: "backbone dependent" and "backbone independent." A backbone dependent rotamer library allows different rotamers depending on the position of the residue in the backbone; thus for example, certain leucine rotamers are allowed if the position is within an α helix, and different leucine rotamers are allowed if the position is not in an α-helix. A backbone independent rotamer library utilizes all rotamers of an amino acid at every position. In general, a backbone independent library is preferred in the consideration of core residues, since flexibility in the core is important. However, backbone independent libraries are computationally more expensive, and thus for surface and boundary positions, a backbone dependent library is preferred. However, either type of library can be used at any position.

"Variable residue position" herein is meant an amino acid position of the protein to be designed that is not fixed in the design method as a specific residue or rotamer, generally the wild-type residue or rotamer. It should be noted that even if a position is chosen as a variable position, it is possible that the methods of the invention will optimize the sequence in such a way as to select the wild type residue at the variable position.

This generally occurs more frequently for core residues, and less regularly for surface residues. In addition, it is possible to fix residues as non-wild type amino acids as well.

"Fixed residue position" means that the residue identified in the three dimensional structure as being in a set conformation. In some embodiments, a fixed position is left in its original conformation (which may or may not correlate to a specific rotamer of the rotamer library being used). Alternatively, residues may be fixed as a non-wild type residue depending on design needs; for example, when known site-directed mutagenesis techniques have shown that a particular residue is desirable (for example, to eliminate a proteolytic site or alter the substrate specificity of an AARS), the residue may be fixed as a particular amino acid. Residues which can be fixed include, but are not limited to, structurally or biologically functional residues. For example, the anchor residues.

In certain embodiments, a fixed position may be "floated"; the amino acid or analog at that position is fixed, but different rotamers of that amino acid or analog are tested. In this embodiment, the variable residues may be at least one, or anywhere from 0.1% to 99.9% of the total number of residues. Thus, for example, it may be possible to change only a few (or one) residues, or most of the residues, with all possibilities in between.

As used herein, the term "orthogonal" refers to a molecule (e.g., an orthogonal tRNA (O-tRNA) and/or an orthogonal aminoacyl tRNA synthetase (O-RS)) that is used with reduced efficiency (as compared to wild-type or endogenous) by a system of interest (e.g., a translational system, e.g., a cell). Orthogonal refers to the inability or reduced efficiency, e.g., less than 20% efficient, less than 10% efficient, less than 5% efficient, or e.g., less than 1% efficient, of an orthogonal tRNA and/or orthogonal RS to function in the translation system of interest. For example, an orthogonal tRNA in a translation system of interest aminoacylates any endogenous RS of a translation system of interest with reduced or even zero efficiency, when compared to aminoacylation of an endogenous tRNA by the endogenous RS. In another example, an orthogonal RS aminoacylates any endogenous tRNA in the translation system of interest with reduced or even zero efficiency, as compared to aminoacylation of the endogenous tRNA by an endogenous RS. "Improvement in orthogonality" refers to enhanced orthogonality compared to a starting material or a naturally occurring tRNA or RS.

"Wobble degenerate codon" refers to a codon encoding a natural amino acid, which codon, when present in mRNA, is recognized by a natural tRNA anticodon through at least one non-Watson-Crick, or wobble base-pairing (e.g., A-C or G-U base-pairing). Watson-Crick base-pairing refers to either the G-C or A-U (RNA or DNA/RNA hybrid) or A-T (DNA) base-pairing. When used in the context of mRNA codon—tRNA anticodon base-pairing, Watson-Crick base-pairing means all codon-anticodon base-pairings are mediated through either G-C or A-U.

As used herein, proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are described herein and are generally available.

The term "preferentially aminoacylates" refers to an efficiency, e.g., about 20%, about 30%, about 40%, about 50%, about 60%, about 70%, about 75%, about 85%, about 90%, about 95%, about 99% or more efficient, at which an O-RS aminoacylates an 0-tRNA with an unnatural amino acid compared to a naturally occurring tRNA or starting material used to generate the O-tRNA. The unnatural amino acid is then incorporated into a growing polypeptide chain with high fidelity, e.g., at greater than about 20%, 30%, 40%, 50%, 60%, 75%, 80%, 90%, 95%, or greater than about 99% efficiency for a given codon.

The term "complementary" refers to components of an orthogonal pair, O-tRNA and O-RS that can function together, e.g., the O-RS aminoacylates the O-tRNA.

The term "derived from" refers to a component that is isolated from an organism or isolated and modified, or generated, e.g., chemically synthesized, using information of the component from the organism.

The term "translation system" refers to the components necessary to incorporate a naturally occurring or unnatural amino acid into a growing polypeptide chain (protein). For example, components can include ribosomes, tRNA(s), synthetas(es), mRNA and the like. The components of the present invention can be added to a translation system, in vivo or in vitro. An in vivo translation system may be a cell (eukaryotic or prokaryotic cell). An in vitro translation system may be a cell-free system, such as reconstituted one with components from different organisms (purified or recombinantly produced).

The term "inactive RS" refers to a synthetase that have been mutated so that it no longer can aminoacylate its cognate tRNA with an amino acid.

The term "selection agent" refers to an agent that when present allows for a selection of certain components from a population, e.g., an antibiotic, wavelength of light, an antibody, a nutrient or the like. The selection agent can be varied, e.g., such as concentration, intensity, etc.

The term "positive selection marker" refers to a marker than when present, e.g., expressed, activated or the like, results in identification of an organism with the positive selection marker from those without the positive selection marker.

The term "negative selection marker" refers to a marker than when present, e.g., expressed, activated or the like, allows identification of an organism that does not possess the desired property (e.g., as compared to an organism which does possess the desired property).

The term "reporter" refers to a component that can be used to select components described in the present invention. For example, a reporter can include a green fluorescent protein, a firefly luciferase protein, or genes such as β-gal/lacZ (β-galactosidase), Adh (alcohol dehydrogenase) or the like.

The term "not efficiently recognized" refers to an efficiency, e.g., less than about 10%, less than about 5%, or less than about 1%, at which a RS from one organism aminoacylates O-tRNA.

The term "eukaryote" refers to organisms belonging to the phylogenetic domain Eucarya such as animals (e.g., mammals, insects, reptiles, birds, etc.), ciliates, plants, fungi (e.g., yeasts, etc.), flagellates, microsporidia, protists, etc. Additionally, the term "prokaryote" refers to non-eukaryotic organisms belonging to the Eubacteria (e.g., *Escherichia coli, Thermus thermophilus*, etc.) and Archaea (e.g., *Methanococcus jannaschii, Methanobacterium thermoautotrophicum, Halobacterium* such as *Haloferax volcanii* and *Halobacterium* species NRC-1, *A. fulgidus, P. firiosus, P. horikoshii, A. pernix*, etc.) phylogenetic domains.

III. The Genetic Code, Host Cells, and the Degenerate Codons

The standard genetic code most cells use is listed below.

| | | The Genetic Code Middle | | | |
|---|---|---|---|---|---|
| First | U | C | A | G | Last |
| U | Phe | Ser | Tyr | Cys | U |
| | Phe | Ser | Tyr | Cys | C |
| | Leu | Ser | Stop (Ochre) | Stop (Umber) | A |
| | Leu | Ser | Stop (Amber) | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

The genetic code is degenerate, in that the protein biosynthetic machinery utilizes 61 mRNA sense codons to direct the templated polymerization of the 20 natural amino acid monomers. (Crick et al., Nature 192: 1227, 1961). Just two amino acids, i.e., methionine and tryptophan, are encoded by unique mRNA triplets.

The standard genetic code applies to most, but not all, cases. Exceptions have been found in the mitochondrial DNA of many organisms and in the nuclear DNA of a few lower organisms. Some examples are given in the following table.

Examples of non-standard genetic codes.

| Mitochondria | Vertibrates | UGA→ Trp; AGA, AGG → STOP |
|---|---|---|
| | Invertibrates | UGA→ Trp; AGA, AGG → Ser |
| | Yeasts | UGA→ Trp; CUN → Thr |
| | Protista | UGA→ Trp; |
| Nucleus | Bacteria | GUG, UUG, AUU, CUG → initiation |
| | Yeasts | CUG → Ser |
| | Ciliates | UAA, UAG → Gln |

*Plant cells use the standard genetic code in both mitochondria and the nucleus.

*Plant cells use the standard genetic code in both mitochondria and the nucleus.

The NCBI (National Center for Biotechnology Information) maintains a detailed list of the standard genetic code, and genetic codes used in various organisms, including the vertebrate mitochondrial code; the yeast mitochondrial code; the mold, protozoan, and coelenterate mitochondrial code and the mycoplasma/spiroplasma code; the invertebrate mitochondrial code; the ciliate, dasycladacean and hexamita nuclear code; the echinoderm and flatworm mitochondrial code; the euplotid nuclear code; the bacterial and plant plastid code; the alternative yeast nuclear code; the ascidian mitochondrial code; the alternative flatworm mitochondrial code; blepharisma nuclear code; chlorophycean mitochondrial code; trematode mitochondrial code; scenedesmus obliquus mitochondrial code; thraustochytrium mitochondrial code (all incorporated herein by reference). These are primarily based on the reviews by Osawa et al., *Microbiol. Rev.* 56: 229-264, 1992, and Jukes and Osawa, *Comp. Biochem. Physiol.* 106B: 489-494, 1993.

Host Cells

The methods of the invention can be practiced within a cell, which enables production levels of proteins to be made for practical purposes. Because of the high degree of conservation of the genetic code and the surrounding molecular machinery, method of the invention can be used in most cells.

In preferred embodiments, the cells used are culturable cells (i.e., cells that can be grown under laboratory conditions). Suitable cells include mammalian cells (human or non-human mammals), bacterial cells, and insect cells, etc.

Degenerate Codon Selection

As described above, all amino acids, with the exception of methionine and tryptophan are encoded by more than one codon. According to the methods of the invention, a codon that is normally used to encode a natural amino acid is reprogrammed to encode an amino acid analog. An amino acid analog can be a naturally occurring or canonical amino acid analog. In a preferred embodiment, the amino acid analog is not a canonically encoded amino acid.

The thermodynamic stability of a codon-anticodon pair can be predicted or determined experimentally. According to the invention, it is preferable that the orthogonal tRNA interacts with the degenerate codon with an affinity (at 37° C.) of at least about 1.0 kcal/mol more strongly, even more preferably 1.5 kcal/mole more strongly, and even more preferably more than 2.0 kcal/mol more strongly than a natural tRNA in the cell would recognize the same sequence. These values are known to one of skill in the art and can be determined by thermal denaturation experiments (see, e.g., Meroueh and Chow, *Nucleic Acids Res.* 27: 1118, 1999).

The following table lists some of the known anti-codon sequences for *E. coli*. In general, for any organism, tRNA anticodon sequence can be routinely determined using art-recognized technologies. For example, any tRNA gene can be amplified by, for example, PCR. Sequencing can be performed to determine the exact sequences of the anti-codon loop. Alternatively, biochemical binding assay may be used to determine the binding affinity of a purified tRNA to one of the 2-6 possible codons. The codon that binds the tRNA with the highest specificity/affinity presumably has pure Watson-Crick match at all three codon positions, thus determining the sequence of the anti-codon loop.

In general, the wobble base in the anti-codon loop tends to be G or U (rather than A or C).

The Degenerate Codons for E. coli

| Amino Acid | Anticodon | Base-paring at 3rd base | Codon | Amino Acid | Anticodon | Base-paring | Codon |
|---|---|---|---|---|---|---|---|
| Ala | GGC | W/C[1] | GCC | His | GUG | W/C | CAC |
| | | Wobble[2] | GCU | | | Wobble | CAU |
| | UGC | W/C | GCA | Ile | GAU | W/C | AUC |
| | | Wobble | GCG | | | Wobble | AUU |
| Asp | GUC | W/C | GAC | Leu | GAG | W/C | CUC |
| | | Wobble | GAU | | | Wobble | CUU |
| Asn | GUU | W/C | AAC | Lys | UUU | W/C | AAA |
| | | Wobble | AAU | | | Wobble | AAG |
| Cys | GCA | W/C | UGC | Phe | GAA | W/C | UUC |
| | | Wobble | UGU | | | Wobble | UUU |
| Glu | UUC | W/C | GGA | Ser | GGA | W/C | UUC |
| | | Wobble | GAG | | | Wobble | UCU |
| Gly | GCC | W/C | GGC | Tyr | GUA | W/C | UAC |
| | | Wobble | GGU | | | Wobble | UAU |

[1]Watson-Crick base pairing,
[2]Wobble base pairing

When the cell has a single tRNA that recognizes a codon through a perfect complementary interaction between the anticodon of the tRNA and one codon, and recognizes a second, degenerate codon through a wobble or other non-standard base pairing interaction, a new tRNA can be constructed having an anticodon sequence that is perfectly complementary to the degenerate codon.

When the cell has multiple tRNA molecules for a particular amino acid, and one tRNA has an anticodon sequence that is perfectly complementary to the degenerate codon selected, the gene encoding the tRNA can be disabled through any means available to one of skill in the art including, for example, site-directed mutagenesis or deletion of either the gene or the promoter sequence of the gene. Expression of the gene also can be disable through any antisense or RNA interference techniques.

IV. Unnatural Amino Acids

The first step in the protein engineering process is usually to select a set of unnatural amino acids that have the desired chemical properties. The selection of unnatural amino acids depends on pre-determined chemical properties one would like to have, and the modifications one would like to make in the target protein. Unnatural amino acids, once selected, can either be purchased from vendors, or chemically synthesized.

A wide variety of unnatural amino acids can be used in the methods of the invention. The unnatural amino acid can be chosen based on desired characteristics of the unnatural amino acid, e.g., function of the unnatural amino acid, such as modifying protein biological properties such as toxicity, biodistribution, or half life, structural properties, spectroscopic properties, chemical and/or photochemical properties, catalytic properties, ability to react with other molecules (either covalently or noncovalently), or the like.

As used herein an "unnatural amino acid" refers to any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

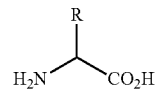

Formula I

An unnatural amino acid is typically any structure having Formula I wherein the R group is any substituent other than one used in the twenty natural amino acids. See, e.g., any biochemistry text such as Biochemistry by L. Stryer, 3rd ed. 1988, Freeman and Company, New York, for structures of the twenty natural amino acids. Note that, the unnatural amino acids of the present invention may be naturally occurring compounds other than the twenty alpha-amino acids above. Because the unnatural amino acids of the invention typically differ from the natural amino acids in side chain only, the unnatural amino acids form amide bonds with other amino acids, e.g., natural or unnatural, in the same manner in which they are formed in naturally occurring proteins. However, the unnatural amino acids have side chain groups that distinguish them from the natural amino acids. For example, R in Formula I optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto containing amino acids, amino acids comprising polyethylene glycol or polyether, heavy atom substituted amino acids, chemically cleavable and/or photocleavable amino acids, amino acids with an elongated side chains as compared to natural amino acids, e.g., polyethers or long chain hydrocarbons, e.g., greater than about 5 or greater than about 10 carbons, carbon-linked sugar-containing amino acids, redox-active amino acids, amino thioacid containing amino acids, and amino acids comprising one or more toxic moiety.

In addition to unnatural amino acids that contain novel side chains, unnatural amino acids also optionally comprise modified backbone structures, e.g., as illustrated by the structures of Formula II and III:

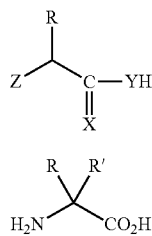

Formula II

Formula III wherein Z typically comprises OH, NH$_2$, SH, NH—R', or S—R'; X and Y, which may be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

For example, many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, β-substituted derivatives, cyclic derivatives, and amide substituted glutamine derivatives. Example phenylalanine analogs include, but are not limited to, meta-substituted phenylalanines, wherein the substituent comprises a hydroxy group, a methoxy group, a methyl group, an allyl group, an acetyl group, or the like.

Specific examples of unnatural amino acids include, but are not limited to, O-methyl-L-tyrosine, an L-3-(2-naphthyl) alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of non-limiting unnatural amino acids are provided in the figures, e.g., FIGS. 29, 30, and 31 of US 2003/0108885 A1 (entire content incorporated herein by reference).

Typically, the unnatural amino acids of the invention are selected or designed to provide additional characteristics unavailable in the twenty natural amino acids. For example, unnatural amino acid are optionally designed or selected to modify the biological properties of a protein, e.g., into which they are incorporated. For example, the following properties are optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Further details regarding unnatural amino acids are described in US 2003-0082575 A1, entitled "In vivo Incorporation of Unnatural Amino Acids," filed on Apr. 19, 2002, which is incorporated herein by reference.

Additionally, other examples optionally include (but are not limited to) an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged amino acid; a photoisomerizable amino acid; a biotin or biotin-analogue containing amino acid; a glycosylated or carbohydrate modified amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; and a cyclic amino acid other than proline.

V. Aminoacyl-tRNA Synthetases

The aminoacyl-tRNA synthetase (used interchangeably herein with AARS or "synthetase") used in the methods of the invention can be a naturally occurring synthetase derived from a different organism, a mutated synthetase, or a designed synthetase.

The synthetase used can recognize the desired (unnatural) amino acid analog selectively over related amino acids available to the cell. For example, when the amino acid analog to be used is structurally related to a naturally occurring amino acid in the cell, the synthetase should charge the orthogonal tRNA molecule with the desired amino acid analog with an efficiency at least substantially equivalent to that of, and more preferably at least about twice, 3 times, 4 times, 5 times or more than that of the naturally occurring amino acid. However, in cases in which a well-defined protein product is not necessary, the synthetase can have relaxed specificity for charging amino acids. In such an embodiment, a mixture of orthogonal tRNAs could be produced, with various amino acids or analogs.

In certain embodiments, it is preferable that the synthetase have activity both for the amino acid analog and for the amino acid that is encoded by the degenerate codon of the orthologous tRNA molecule. In the absence of the amino acid analog, this allows the cell to continue to grow, while upon addition of the amino acid analog to the cell, allows a switch to allow incorporation of the amino acid analog. The synthetase also should be relatively specific for the orthogonal tRNA molecule over other naturally occurring tRNA molecules within the cell. Choosing a tRNA-synthetase pair from an unrelated organism will generally allow for such selectivity. The selectivity of the synthetase for the orthogonal tRNA can be tested experimentally by testing the ability of the orthogonal synthetase to charge the natural tRNAs of the host cell with canonical amino acids. (Orthogonality could be confirmed by even natural amino acids, because tRNA recognition domain in synthetase might be different from that for amino acid analogs. Of course, amino acid analogs should be charged only into orthogonal tRNA efficiently by synthetase, after binding site of synthetase is appropriately modified). Such procedures are described, for example, in Doctor and Mudd, *J. Biol. Chem.* 238: 3677-3681, 1963; Wang et al., Science 292: 498-500, 2001).

The method involves introduction into the host cell of a heterologous aminoacyl-tRNA synthetase and its cognate tRNA. If cross-charging between the heterologous pair and the translational apparatus of the host is slow or absent, and if the analogue is charged only by the heterologous synthetase, insertion of the analog can be restricted (or at least biased) to sites characterized by the most productive base-pairing between the heterologous tRNA and the messenger RNA of interest.

A synthetase can be obtained by a variety of techniques known to one of skill in the art, including combinations of such techniques as, for example, computational methods, selection methods, and incorporation of synthetases from other organisms (see below).

In certain embodiments, synthetases can be used or developed that efficiently charge tRNA molecules that are not charged by synthetases of the host cell. For example, suitable pairs may be generally developed through modification of synthetases from organisms distinct from the host cell.

In certain embodiments, the synthetase can be developed by selection procedures.

In certain embodiments, the synthetase can be designed using computational techniques such as those described in Datta et al., *J. Am. Chem. Soc.* 124: 5652-5653, 2002, and in copending U.S. patent application Ser. No. 10/375,298 (or US patent application publication US20040053390A1, see below).

1. Computational Design of AARS

Specifically, in one embodiment, the subject method partly depends on the design and engineering of natural AARS to a modified form that has relaxed substrate specificity, such that it can uptake non-canonical amino acid analogs as a substrate, and charge a modified tRNA (with its anticodon changed) with such a non-canonical amino acid. The following sections briefly describe a method for the generation of such modified AARS, which method is described in more detail in US patent application publication US20040053390A1, the entire contents of which are incorporated herein by reference.

Briefly, the methods described therein relate to computational tools for modifying the substrate specificity of an AminoAcyl tRNA Synthetases (AARSs) through mutation to enable the enzyme to more efficiently utilize amino acid analog(s) in protein translation systems, either in vitro or in whole cells. A salient feature to the described invention is methods and tools for systematically redesigning the substrate binding site of an AARS enzyme to facilitate the use of unnatural substrates in the peptide or protein translation reaction the enzyme catalyzes.

According to the method, a rotamer library for the artificial amino acid is built by varying its torsional angles to create rotamers that would fit in the binding pocket for the natural substrate. The geometric orientation of the backbone of the amino acid analog is specified by the crystallographic orientation of the backbone of the natural substrate in the crystal structure. Amino acids in the binding pocket of the synthetase that interact with the side chain on the analog are allowed to vary in identity and rotameric conformation in the subsequent protein design calculations.

The protocol also employ a computational method to enhance the interactions between the substrate and the protein positions. This is done by scaling up the pair-wise energies between the substrate and the amino acids allowed at the design positions on the protein in the energy calculations. In an optimization calculation where the protein-substrate interactions are scaled up compared to the intra-protein interactions, sequence selection is biased toward selecting amino acids to be those that have favorable interaction with the substrate.

The described method helped to construct a new modified form of the *E. coli* phenylalanyl-tRNA synthetase, based on the known structure of the related *Thermus thermophilus* PheRS (tPheRS). The new modified form of the *E. coli* phenylalanyl-tRNA synthetase (ePheRS**) allows efficient in vivo incorporation of reactive aryl ketone functionality into recombinant proteins. The results described therein also demonstrate the general power of computational protein design in the development of aminoacyl-tRNA synthetases for activation and charging of unnatural amino acids.

A. Available Sequence and Structural Information for tRNA Synthetases

Protein translation from an mRNA template is carried out by ribosomes. During the translation process, each tRNA is matched with its amino acid long before it reaches the ribosome. The match is made by a collection of enzymes known as the aminoacyl-tRNA synthetases (AARS). These enzymes charge each tRNA with the proper amino acid, thus allowing each tRNA to make the proper translation from the genetic code of DNA (and the mRNA transcribed from the DNA) into the amino acid code of proteins.

Most cells make twenty different aminoacyl-tRNA synthetases, one for each type of amino acid. These twenty enzymes are each optimized for function with its own particular amino acid and the set of tRNA molecules appropriate to that amino acid. Aminoacyl-tRNA synthetases must perform their tasks with high accuracy. Many of these enzymes recognize their tRNA molecules using the anticodon. These enzymes make about one mistake in 10,000. For most amino acids, this level of accuracy is not too difficult to achieve, since most of the amino acids are quite different from one another.

In the subject method, an accurate description of the AARS binding pocket for tRNA is important for the computational design approach, since it depends on the crystal structure for the protein backbone descriptions, although in many cases it is perfectly acceptable to use crystal structure of a homologous protein (for example, a homolog from a related species) or even a conserved domain to substitute the crystallographic binding pocket structure description. The crystal structure also defines the orientation of the natural substrate amino acid in the binding pocket of a synthetase, as well as the relative position of the amino acid substrate to the synthetase residues, especially those residues in and around the binding pocket. To design the binding pocket for the analogs, it is preferred that these analogs bind to the synthetase in the same orientation as the natural substrate amino acid, since this orientation may be important for the adenylation step.

The AARSs may be from any organism, including prokaryotes and eukaryotes, with enzymes from bacteria, fungi, extremeophiles such as the archebacteria, worm, insects, fish, amphibian, birds, animals (particularly mammals and particularly human) and plants all possible.

As described above, most cells make twenty different aminoacyl-tRNA synthetases, one for each type of amino acid. Some suitable synthetases are known, including: yeast phenylalanyl-tRNA synthetase (Kwon et al., *J. Am. Chem. Soc.* 125: 7512-7513, 2003); *Methonococcus jannaschii* tyrosyl-tRNA synthetase (Wang et al., *Science* 292, 498-500, 2001); and yeast tyrosyl-tRNA synthetase (Ohno et al., *J. Biochem.* 130, 417-423, 2001). In fact, the crystal structures of nearly all 20 different AARS enzymes are currently available in the Brookhaven Protein Data Bank (PDB, see Bernstein et al., *J. Mol. Biol.* 112: 535-542, 1977). A list of all the AARSs with solved crystal structures as of April 2001 is available on the PDB website. For example, the crystal structure of *Thermus Aquaticus* Phenylalanyl tRNA Synthetase complexed with Phenylalanine has a resolution of 2.7 Å, and its PDB ID is 1B70.

The structure database or Molecular Modeling DataBase (MMDB) contains experimental data from crystallographic and NMR structure determinations. The data for MMDB are obtained from the Protein Data Bank (PDB). The NCBI (National Center for Biotechnology Information) has cross-linked structural data to bibliographic information, to the sequence databases, and to the NCBI taxonomy. Cn3D, the NCBI 3D structure viewer, can be used for easy interactive visualization of molecular structures from Entrez.

The Entrz 3D Domains database contains protein domains from the NCBI Conserved Domain Database (CDD). Computational biologists define conserved domains based on recurring sequence patterns or motifs. CDD currently contains domains derived from two popular collections, Smart and Pfam, plus contributions from colleagues at NCBI, such as COG. The source databases also provide descriptions and links to citations. Since conserved domains correspond to compact structural units, CDs contain links to 3D-structure via Cn3D whenever possible.

To identify conserved domains in a protein sequence, the CD-Search service employs the reverse position-specific BLAST algorithm. The query sequence is compared to a position-specific score matrix prepared from the underlying conserved domain alignment. Hits may be displayed as a pairwise alignment of the query sequence with a representative domain sequence, or as a multiple alignment. CD-Search now is run by default in parallel with protein BLAST searches. While the user waits for the BLAST queue to further process the request, the domain architecture of the query may already be studied. In addition, CDART, the Conserved Domain Architecture Retrieval Tool allows user to search for proteins with similar domain architectures. CDART uses precomputed CD-search results to quickly identify proteins with a set of domains similar to that of the query. For more details, see Marchler-Bauer et al., *Nucleic Acids Research* 31: 383-387, 2003; and Marchler-Bauer et al., *Nucleic Acids Research* 30: 281-283, 2002.

In addition, a database of known aminoacyl tRNA synthetases has been published by Maciej Szymanski, Marzanna A. Deniziak and Jan Barciszewski, in *Nucleic Acids Res.* 29:288-290, 2001 (titled "Aminoacyl-tRNA synthetases database"). A corresponding website (http://rose.man.poznan.pl/aars/seq_main.html) provides details about all known AARSs from different species. For example, according to the database, the Isoleucyl-tRNA Synthetase for the radioresistant bacteria *Deinococcus radiodurans* (Accession No. AAF10907) has 1078 amino acids, and was published by White et al. in *Science* 286:1571-1577 (1999); the Valyl-tRNA Synthetase for mouse (*Mus musculus*) has 1263 amino acids (Accession No. AAD26531), and was published by Snoek M. and van Vugt H. in *Immunogenetics* 49: 468-470 (1999); and the Phenylalanyl-tRNA Synthetase sequences for human, *Drosophila, S. pombe, S. cerevisiae, Candida albicans, E. coli*, and mumerous other bacteria including *Thermus aquaticus* ssp. *thermophilus* are also available. The database was last updated in September 2003. Similar information for other newly identified AARSs can be obtained, for example, by conducting a BLAST search using any of the known sequences in the AARS database as query against the available public (such as the non-redundant database at NCBI, or "nr") or proprietory private databases.

Alternatively, in certain embodiments, if the exact crystal structure of a particular AARS is not known, but its protein sequence is similar or homologous to a known AARS sequence with a known crystal structure. In such instances, it is expected that the conformation of the AARS in question will be similar to the known crystal structure of the homologous AARS. The known structure may, therefore, be used as the structure for the AARS of interest, or more preferably, may be used to predict the structure of the AARS of interest (i.e., in "homology modeling" or "molecular modeling"). As a particular example, the Molecular Modeling Database (MMDB) described above (see, Wang et al., *Nucl. Acids Res.* 2000, 28:243-245; Marchler-Bauer et al., *Nucl. Acids Res.* 1999, 27:240-243) provides search engines that may be used to identify proteins and/or nucleic acids that are similar or homologous to a protein sequence (referred to as "neighboring" sequences in the MMDB), including neighboring sequences whose three-dimensional structures are known. The database further provides links to the known structures along with alignment and visualization tools, such as Cn3D (developed by NCBI), RasMol, etc., whereby the homologous and parent sequences may be compared and a structure may be obtained for the parent sequence based on such sequence alignments and known structures.

The homologous AARS sequence with known 3D-structure is preferably at least about 60%, or at least about 70%, or at least about 80%, or at least about 90%, or at least about 95% identical to the AARS of interest in the active site region or the pocket region for amino acid substrate binding. Such active site or pocket site may not be continuous in the primary amino acid sequence of the AARS since distant amino acids may come together in the 3D-structure. In this case, sequence homology or identity can be calculated using, for example, the NCBI standard BLASTp programs for protein using default conditions, in regions aligned together (without insertions or deletions in either of the two sequences being compared) and including residues known to be involved in substrate amino acid binding. For example, the *Thermus Aquaticus* Phenylalanyl tRNA Synthetase alpha subunit appears to have an "insert" region from residues 156 to 165 when compared to its homologs from other species. This region can be disregarded in calculating sequence identity. Alternatively, the homologous AARS is preferably about 35%, or 40%, or 45%, or 50%, or 55% identical overall to the AARS of interest. The *E. coli* Phenylalanyl tRNA Synthetase alpha subunit is about 45% identical overall, and about 80% identical in the active site region to the *Thermus Aquaticus* Phenylalanyl tRNA Synthetase. The human Phenylalanyl tRNA Synthetase alpha subunits is about 62%, 60%, 54%, 50% identical overall to its *Drosophila*, worm (*C. elegans*), plant (*Arabidopsis thaliana*), yeast (*S. cerevisiae*) counterparts, respectively.

In the few cases where the structure for a particular AARS sequence may not be known or available, it is typically possible to determine the structure using routine experimental techniques (for example, X-ray crystallography and Nuclear Magnetic Resonance (NMR) spectroscopy) and without undue experimentation. See, e.g., *NMR of Macromolecules: A Practical Approach*, G. C. K. Roberts, Ed., Oxford University Press Inc., New York (1993); Ishima and Torchia, *Nat. Struct. Biol.* 7: 740-743, 2000; Gardner and Kay, *Annu. Rev. Bioph. Biom.* 27: 357-406, 1998; Kay, *Biochern. Cell. Biol.* 75: 1-15, 1997; Dayie et al., *Annu. Rev. Phys. Chem.* 47: 243-282, 1996; Wuthrich, *Acta Cyrstallogr. D* 51: 249-270, 1995; Kahn et al., *J. Synchrotron Radiat.* 7: 131-138, 2000; Oakley and Wilce, *Clin. Exp. Pharmacol. P.* 27: 145-151, 2000; Fourme et al., *J. Synchrotron Radiat.* 6: 834-844, 1999.

Alternatively, and in less preferable embodiments, the three-dimensional structure of a AARS sequence may be calculated from the sequence itself and using ab initio molecular modeling techniques already known in the art. See e.g., Smith et al., *J. Comput. Biol.* 4: 217-225, 1997; Eisenhaber et al., *Proteins* 24: 169-179, 1996; Bohm, *Biophys Chem.* 59: 1-32, 1996; Fetrow and Bryant, *BioTechnol.* 11: 479-484, 1993; Swindells and Thorton, *Curr. Opin. Biotech.* 2: 512-519, 1991; Levitt et al., *Annu. Rev. Biochem.* 66: 549-579, 1997; Eisenhaber et al., *Crit. Rev. Biochem. Mol.* 30:1-94, 1995; Xia et al., *J. Mol. Biol.* 300: 171-185, 2000; Jones, *Curr. Opin. Struc. Biol.* 10: 371-379, 2000. Three-dimensional structures obtained from ab initio modeling are typically less reliable than structures obtained using empirical (e.g., NMR spectroscopy or X-ray crystallography) or semi-empirical (e.g., homology modeling) techniques. However, such structures will generally be of sufficient quality, although less preferred, for use in the methods of this invention.

For additional details, see section B below.

B. Methods for Predicting 3D Structure Based on Sequence Homology

For AARS proteins that have not been crystallized or been the focus of other structural determinations, a computer-generated molecular model of the AARS and its binding site can nevertheless be generated using any of a number of techniques available in the art. For example, the Cα-carbon positions of the target AARS sequence can be mapped to a particular coordinate pattern of an AARS enzyme ("known AARS") having a similar sequence and deduced structure using homology modeling techniques, and the structure of the target protein and velocities of each atom calculated at a simulation temperature (To) at which a docking simulation with an amino acid analog is to be determined. Typically, such a protocol involves primarily the prediction of side-chain conformations in the modeled target AARS protein, while assuming a main-chain trace taken from a tertiary structure, such as provided by the known AARS protein. Computer programs for performing energy minimization routines are commonly used to generate molecular models. For example, both the CHARMM (Brooks et al. (1983) *J Comput Chem* 4:187-217) and AMBER (Weiner et al (1981) *J. Comput. Chem.* 106: 765) algorithms handle all of the molecular system setup, force field calculation, and analysis (see also, Eisenfield et al. (1991) *Am J Physiol* 261:C376-386; Lybrand (1991) *J Pharm Belg* 46:49-54; Froimowitz (1990) *Biotechniques* 8:640-644; Burbam et al. (1990) *Proteins* 7:99-111; Pedersen (1985) *Environ Health Perspect* 61:185-190; and Kini et al. (1991) *J Biomol Struct Dyn* 9:475-488). At the heart of these programs is a set of subroutines that, given the position of every atom in the model, calculate the total potential energy of the system and the force on each atom. These programs may utilize a starting set of atomic coordinates, the parameters for the various terms of the potential energy function, and a description of the molecular topology (the covalent structure). Common features of such molecular modeling methods include: provisions for handling hydrogen bonds and other constraint forces; the use of periodic boundary conditions; and provisions for occasionally adjusting positions, velocities, or other parameters in order to maintain or change temperature, pressure, volume, forces of constraint, or other externally controlled conditions.

Most conventional energy minimization methods use the input coordinate data and the fact that the potential energy function is an explicit, differentiable function of Cartesian coordinates, to calculate the potential energy and its gradient (which gives the force on each atom) for any set of atomic positions. This information can be used to generate a new set of coordinates in an effort to reduce the total potential energy and, by repeating this process over and over, to optimize the molecular structure under a given set of external conditions. These energy minimization methods are routinely applied to molecules similar to the subject AARS proteins.

In general, energy minimization methods can be carried out for a given temperature, Ti, which may be different than the docking simulation temperature, To. Upon energy minimization of the molecule at Ti, coordinates and velocities of all the atoms in the system are computed. Additionally, the normal modes of the system are calculated. It will be appreciated by those skilled in the art that each normal mode is a collective, periodic motion, with all parts of the system moving in phase with each other, and that the motion of the molecule is the superposition of all normal modes. For a given temperature, the mean square amplitude of motion in a particular mode is inversely proportional to the effective force constant for that mode, so that the motion of the molecule will often be dominated by the low frequency vibrations.

After the molecular model has been energy minimized at Ti, the system is "heated" or "cooled" to the simulation temperature, To, by carrying out an equilibration run where the velocities of the atoms are scaled in a step-wise manner until the desired temperature, To, is reached. The system is further equilibrated for a specified period of time until certain properties of the system, such as average kinetic energy, remain constant. The coordinates and velocities of each atom are then obtained from the equilibrated system.

Further energy minimization routines can also be carried out. For example, a second class of methods involves calculating approximate solutions to the constrained EOM for the protein. These methods use an iterative approach to solve for the Lagrange multipliers and, typically, only need a few iterations if the corrections required are small. The most popular method of this type, SHAKE (Ryckaert et al. (1977) *J Comput Phys* 23:327; and Van Gunsteren et al. (1977) *Mol Phys* 34:1311) is easy to implement and scales as O(N) as the number of constraints increases. Therefore, the method is applicable to macromolecules such as AARS proteins. An alternative method, RATTLE (Anderson (1983) *J Comput Phys* 52:24) is based on the velocity version of the Verlet algorithm. Like SHAKE, RATTLE is an iterative algorithm and can be used to energy minimize the model of a subject AARS protein.

C. Alternative Methods

In other embodiments, rather than holding the identity of the amino acid analog constant and varying the AARS structure (by modeling several different mutant structures), the subject method is carried out using the molecular model(s) for a single Modified AARS (e.g., in which one more non-anchor amino acid residues are changed) and sampling a variety of different amino acid analogs or potential fragments thereof, to identify analogs which are likely to interact with, and be substrates for the modified AARS enzyme. This approach can make use of coordinate libraries for amino acid analogs (including rotamer variants) or libraries of functional groups and spacers that can be joined to form the side-chain of an amino acid analog.

Using such approaches as described above, e.g., homology modeling, a coordinate set for the binding site for the modified AARS can be derived.

There are a variety of computational methods that can be readily adapted for identifying the structure of amino acid analogs that would have appropriate steric and electronic properties to interact with the substrate binding site of a Modified AARS. See, for example, Cohen et al. (1990) *J. Med. Cam.* 33: 883-894; Kuntz et al. (1982) *J. Mol. Biol* 161: 269-288; DesJarlais (1988) *J. Med. Cam.* 31: 722-729; Bartlett et al. (1989) (*Spec. Publ., Roy. Soc. Chem.*) 78: 182-196; Goodford et al. (1985) *J. Med. Cam.* 28: 849-857; DesJarlais et al. *J. Med. Cam.* 29: 2149-2153). Directed methods generally fall into two categories: (1) design by analogy in which 3-D structures of known molecules (such as from a crystallographic database) are docked to the AARS binding site structure and scored for goodness-of-fit; and (2) de novo design, in which the amino acid analog model is constructed piece-wise in the AARS binding site. The latter approach, in particular, can facilitate the development of novel molecules, uniquely designed to bind to the subject Modified AARS binding site.

In an illustrative embodiment, the design of potential amino acid analogs that may function with a particular modified AARS begins from the general perspective of shape complimentary for the substrate binding site of the enzyme, and a search algorithm is employed which is capable of scanning a database of small molecules of known three-dimensional structure for candidates which fit geometrically into the substrate binding site. Such libraries can be general small molecule libraries, or can be libraries directed to amino acid analogs or small molecules which can be used to create amino acid analogs. It is not expected that the molecules found in the shape search will necessarily be leads themselves, since no evaluation of chemical interaction necessarily be made during the initial search. Rather, it is anticipated that such candidates might act as the framework for further design, providing molecular skeletons to which appropriate atomic replacements can be made. Of course, the chemical complimentary of these molecules can be evaluated, but it is expected that atom types will be changed to maximize the electrostatic, hydrogen bonding, and hydrophobic interactions with the substrate binding site. Most algorithms of this type provide a method for finding a wide assortment of chemical structures that may be complementary to the shape of the AARS substrate binding site.

For instance, each of a set of small molecules from a particular data-base, such as the Cambridge Crystallographic Data Bank (CCDB) (Allen et al. (1973) *J. Chem. Doc.* 13: 119), is individually docked to the binding site of the modified AARS in a number of geometrically permissible orientations with use of a docking algorithm. In a preferred embodiment, a set of computer algorithms called DOCK, can be used to characterize the shape of invaginations and grooves that form the binding site. See, for example, Kuntz et al. (1982) *J. Mol. Biol.* 161: 269-288. The program can also search a database of small molecules for templates whose shapes are complementary to particular binding site of the modified AARS. Exemplary algorithms that can be adapted for this purpose are described in, for example, DesJarlais et al. (1988) *J Med Chem* 31:722-729.

The orientations are evaluated for goodness-of-fit and the best are kept for further examination using molecular mechanics programs, such as AMBER or CHARMM. Such algorithms have previously proven successful in finding a variety of molecules that are complementary in shape to a given binding site of a receptor or enzyme, and have been shown to have several attractive features. First, such algorithms can retrieve a remarkable diversity of molecular architectures. Second, the best structures have, in previous applications to other proteins, demonstrated impressive shape complementarity over an extended surface area. Third, the overall approach appears to be quite robust with respect to small uncertainties in positioning of the candidate atoms.

In certain embodiments, the subject method can utilize an algorithm described by Goodford (1985, *J Med Chem* 28:849-857) and Boobbyer et al. (1989, *J Med Chem* 32:1083-1094). Those papers describe a computer program (GRID) which seeks to determine regions of high affinity for different chemical groups (termed probes) on the molecular surface of the binding site. GRID hence provides a tool for suggesting modifications to known ligands that might enhance binding. It may be anticipated that some of the sites discerned by GRID as regions of high affinity correspond to "pharmacophoric patterns" determined inferentially from a series of known ligands. As used herein, a pharmacophoric pattern is a geometric arrangement of features of the anticipated amino acid analog that is believed to be important for binding. Goodsell and Olson (1990, *Proteins: Struct Funct Genet.* 8:195-202) have used the Metropolis (simulated annealing) algorithm to dock a single known ligand into a target protein, and their approach can be adapted for identifying suitable amino acid analogs for docking with the AARS binding site. This algorithm can allow torsional flexibility in the amino acid side-chain and use GRID interaction energy maps as rapid lookup tables for computing approximate interaction energies.

Yet a further embodiment of the present invention utilizes a computer algorithm such as CLIX which searches such databases as CCDB for small molecules which can be oriented in the substrate binding site of the AARS in a way that is both sterically acceptable and has a high likelihood of achieving favorable chemical interactions between the candidate molecule and the surrounding amino acid residues. The method is based on characterizing the substrate binding site in terms of an ensemble of favorable binding positions for different chemical groups and then searching for orientations of the candidate molecules that cause maximum spatial coincidence of individual candidate chemical groups with members of the ensemble. The current availability of computer power dictates that a computer-based search for novel ligands follows a breadth-first strategy. A breadth-first strategy aims to reduce progressively the size of the potential candidate search space by the application of increasingly stringent criteria, as opposed to a depth-first strategy wherein a maximally detailed analysis of one candidate is performed before proceeding to the next. CLIX conforms to this strategy in that its analysis of binding is rudimentary—it seeks to satisfy the necessary conditions of steric fit and of having individual groups in "correct" places for bonding, without imposing the sufficient condition that favorable bonding interactions actually occur. A ranked "shortlist" of molecules, in their favored orientations, is produced which can then be examined on a molecule-by-molecule basis, using computer graphics and more sophisticated molecular modeling techniques. CLIX is also capable of suggesting changes to the substituent chemical groups of the candidate molecules that might enhance binding. Again, the starting library can be of amino acid analogs or of molecules which can be used to generate the side-chain of an amino acid analog.

The algorithmic details of CLIX is described in Lawerence et al. (1992) Proteins 12:31-41, and the CLIX algorithm can be summarized as follows. The GRID program is used to determine discrete favorable interaction positions (termed target sites) in the binding site of the AARS protein for a wide variety of representative chemical groups. For each candidate ligand in the CCDB an exhaustive attempt is made to make coincident, in a spatial sense in the binding site of the protein, a pair of the candidate's substituent chemical groups with a pair of corresponding favorable interaction sites proposed by GRID. All possible combinations of pairs of ligand groups with pairs of GRID sites are considered during this procedure. Upon locating such coincidence, the program rotates the candidate ligand about the two pairs of groups and checks for steric hindrance and coincidence of other candidate atomic groups with appropriate target sites. Particular candidate/orientation combinations that are good geometric fits in the binding site and show sufficient coincidence of atomic groups with GRID sites are retained.

Consistent with the breadth-first strategy, this approach involves simplifying assumptions. Rigid protein and small molecule geometry is maintained throughout. As a first approximation rigid geometry is acceptable as the energy minimized coordinates of the binding site of the modified AARS, describe an energy minimum for the molecule, albeit a local one.

A further assumption implicit in CLIX is that the potential ligand, when introduced into the substrate binding site of the Modified AARS, does not induce change in the protein's stereochemistry or partial charge distribution and so alter the basis on which the GRID interaction energy maps were computed. It must also be stressed that the interaction sites predicted by GRID are used in a positional and type sense only, i.e., when a candidate atomic group is placed at a site predicted as favorable by GRID, no check is made to ensure that the bond geometry, the state of protonation, or the partial charge distribution favors a strong interaction between the protein and that group. Such detailed analysis should form part of more advanced modeling of candidates identified in the CLIX shortlist.

Yet another embodiment of a computer-assisted molecular design method for identifying amino acid analogs that may be utilized by a predetermined Modified AARS comprises the de novo synthesis of potential inhibitors by algorithmic connection of small molecular fragments that will exhibit the desired structural and electrostatic complementarity with the substrate binding site of the enzyme. The methodology employs a large template set of small molecules with are iteratively pieced together in a model of the AARS' substrate binding site. Each stage of ligand growth is evaluated according to a molecular mechanics-based energy function, which considers van der Waals and coulombic interactions, internal strain energy of the lengthening ligand, and desolvation of both ligand and enzyme. The search space can be managed by use of a data tree which is kept under control by pruning according to the binding criteria.

In yet another embodiment, potential amino acid analogs can be determined using a method based on an energy minimization-quenched molecular dynamics algorithm for determining energetically favorable positions of functional groups in the substrate binding site of a modified AARS enzyme. The method can aid in the design of molecules that incorporate such functional groups by modification of known amino acid and amino acid analogs or through de novo synthesis.

For example, the multiple copy simultaneous search method (MCSS) described by Miranker et al. (1991) Proteins 11: 29-34 can be adapted for use in the subject method. To determine and characterize a local minima of a functional group in the force field of the protein, multiple copies of selected functional groups are first distributed in a binding site of interest on the AARS protein. Energy minimization of these copies by molecular mechanics or quenched dynamics yields the distinct local minima. The neighborhood of these minima can then be explored by a grid search or by constrained minimization. In one embodiment, the MCSS method uses the classical time dependent Hartee (TDH) approximation to simultaneously minimize or quench many identical groups in the force field of the protein.

Implementation of the MCSS algorithm requires a choice of functional groups and a molecular mechanics model for each of them. Groups must be simple enough to be easily characterized and manipulated (3-6 atoms, few or no dihedral degrees of freedom), yet complex enough to approximate the steric and electrostatic interactions that the functional group would have in substrate binding to the site of the AARS protein. A preferred set is, for example, one in which most organic molecules can be described as a collection of such groups (*Patai's Guide to the Chemistry of Functional Groups*, ed. S. Patai (New York: John Wiley, and Sons, (1989)). This includes fragments such as acetonitrile, methanol, acetate, methyl ammonium, dimethyl ether, methane, and acetaldehyde.

Determination of the local energy minima in the binding site requires that many starting positions be sampled. This can be achieved by distributing, for example, 1,000-5,000 groups at random inside a sphere centered on the binding site; only the space not occupied by the protein needs to be considered. If the interaction energy of a particular group at a certain location with the protein is more positive than a given cut-off (e.g. 5.0 kcal/mole) the group is discarded from that site. Given the set of starting positions, all the fragments are minimized simultaneously by use of the TDH approximation (Elber et al. (1990) *J Am Chem Soc* 112: 9161-9175). In this method, the forces on each fragment consist of its internal forces and those due to the protein. The essential element of this method is that the interactions between the fragments are omitted and the forces on the protein are normalized to those due to a single fragment. In this way simultaneous minimization or dynamics of any number of functional groups in the field of a single protein can be performed.

Minimization is performed successively on subsets of, e.g. 100, of the randomly placed groups. After a certain number of step intervals, such as 1,000 intervals, the results can be examined to eliminate groups converging to the same minimum. This process is repeated until minimization is complete (e.g. RMS gradient of 0.01 kcal/mole/Å). Thus the resulting energy minimized set of molecules comprises what amounts to a set of disconnected fragments in three dimensions representing potential side-chains for amino acid analogs.

The next step then is to connect the pieces with spacers assembled from small chemical entities (atoms, chains, or ring moieties) to form amino acid analogs, e.g., each of the disconnected can be linked in space to generate a single molecule using such computer programs as, for example, NEWLEAD (Tschinke et al. (1993) *J Med Chem* 36: 3863, 3870). The procedure adopted by NEWLEAD executes the following sequence of commands (1) connect two isolated moieties, (2) retain the intermediate solutions for further processing, (3) repeat the above steps for each of the intermediate solutions until no disconnected units are found, and (4) output the final solutions, each of which is single molecule. Such a program can use for example, three types of spacers: library spacers, single-atom spacers, and fuse-ring spacers. The library spacers are optimized structures of small molecules such as ethylene, benzene and methylamide. The output produced by programs such as NEWLEAD consist of a set of molecules containing the original fragments now connected by spacers. The atoms belonging to the input fragments maintain their original orientations in space. The molecules are chemically plausible because of the simple makeup of the spacers and functional groups, and energetically acceptable because of the rejection of solutions with van-der Waals radii violations.

In addition, the order in which the steps of the present method are performed is purely illustrative in nature. In fact, the steps can be performed in any order or in parallel, unless otherwise indicated by the present disclosure.

Furthermore, the method of the present invention may be performed in either hardware, software, or any combination thereof, as those terms are currently known in the art. In particular, the present method may be carried out by software, firmware, or microcode operating on a computer or computers of any type. Additionally, software embodying the present invention may comprise computer instructions in any form (e.g., source code, object code, interpreted code, etc.) stored in any computer-readable medium (e.g., ROM, RAM, magnetic media, punched tape or card, compact disc (CD) in any form, DVD, etc.). Furthermore, such software may also be in the form of a computer data signal embodied in a carrier wave, such as that found within the well-known Web pages transferred among devices connected to the Internet. Accordingly, the present invention is not limited to any particular platform, unless specifically stated otherwise in the present disclosure.

Exemplary computer hardware means suitable for carrying out the invention can be a Silicon Graphics Power Challenge server with 10 R10000 processors running in parallel. Suitable software development environment includes CERIUS2 by Biosym/Molecular Simulations (San Diego, Calif.), or other equivalents.

The computational method described above has been effectively used in modifying enzymes of the protein synthesis machinery (e.g. AARS) to allow incorporation of unnatural amino acids. The same suite of computational tools can also be leveraged to design the final products (e.g., monoclonal antibodies or other therapeutics) in which the unnatural amino acids would be incorporated so as to enhance or modify their structural or functional properties.

While particular embodiments of the present invention have been shown and described, it will be apparent to those skilled in the art that changes and modifications may be made without departing from this invention in its broader aspect and, therefore, the appended claims are to encompass within their scope all such changes and modifications as fall within the true spirit of this invention.

2. Adoption of AARS from Different Organisms

A second strategy for generating an orthogonal tRNA/synthetase pair involves importing a tRNA/synthetase pair from another organism into the translation system of interest, such as *Escherichia coli*. In this particular example, the properties of the heterologous synthetase candidate include, e.g., that it does not charge *Escherichia coli* tRNA reasonably well (preferably not at all), and the properties of the heterologous tRNA candidate include, e.g., that it is not acylated by *Escherichia coli* synthetase to a reasonable extent (preferably not at all). In addition, the O-tRNA derived therefrom is orthogonal to all *Escherichia coli* synthetases.

Schimmel et al. reported that *Escherichia coli* GlnRS (EcGlnRS) does not acylate *Saccharomyces cerevisiae* tRNAGln (EcGlnRS lacks an N-terminal RNA-binding domain possessed by *Saccharomyces cerevisiae* GlnRS (ScGlnRS)). See, E. F. Whelihan and P. Schimmel, EMBO J., 16:2968 (1997). For example, the *Saccharomyces cerevisiae* amber suppressor tRNAGln (SctRNAGlnCUA) was analyzed to determine whether it is also not a substrate for EcGlnRS. In vitro aminoacylation assays showed this to be the case; and in vitro suppression studies show that the SctRNAGlnCUA is competent in translation. See, e.g., Liu and Schultz, Proc. Natl. Acad. Sci. USA, 96:4780 (1999). It was further shown that ScGlnRS does not acylate any *Escherichia coli* tRNA, only the SctRNAGlnCUA in vitro. The degree to which ScGlnRS is able to aminoacylate the SctRNAGlnCUA in *Escherichia coli* was also evaluated using an in vivo complementation assay. An amber nonsense mutation was introduced at a permissive site in the β-lactamase gene. Suppression of the mutation by an amber suppressor tRNA should produce full-length β-lactamase and confer ampicillin resistance to the cell. When only SctRNAGlnCUA is expressed, cells exhibit an $IC_{50}$ of 20 µg/mL ampicillin, indicating virtually no acylation by endogenous *Escherichia coli* synthetases; when SctRNAGlnCUA is coexpressed with ScGlnRS, cells acquire an $IC_{50}$ of about 500 µg/mL ampicillin, demonstrating that ScGlnRS acylates SctRNAGlnCUA efficiently in *Escherichia coli*. See, Liu and Schultz, Proc. Natl. Acad. Sci. USA, 96:4780 (1999). The *Saccharomyces cerevisiae* tRNAGlnCUA/GlnRS is orthogonal to *Escherichia coli*.

This strategy was also applied to a tRNAAsp/AspRS system. *Saccharomyces cerevisiae* $tRNA^{Asp}$ is known to be orthogonal to *Escherichia coli* synthetases. See, e.g., B. P. Doctor and J. A. Mudd, J. Biol. Chem., 238:3677 (1963); and, Y. Kwok and J. T. Wong, Can. J. Biochem., 58:213 (1980). It was demonstrated that an amber suppressor tRNA derived from it ($SctRNA^{Asp}_{CUA}$) is also orthogonal in *Escherichia coli* using the in vivo β-lactamase assay described above. However, the anticodon of $tRNA^{Asp}$ is a critical recognition element of AspRS, see, e.g., R. Giege, C. Florentz, D. Kern, J. Gangloff, G. Eriani and D. Moras, Biochimie, 78:605 (1996), and mutation of the anticodon to CUA results in a loss of affinity of the suppressor for AspRS. An *Escherichia coli* AspRS E93K mutant has been shown to recognize *Escherichia coli* amber suppressor $tRNA^{Asp}_{CUA}$ about an order of magnitude better than wt AspRS. See, e.g., F. Martin, 'Thesis', Universite Louis Pasteur, Strasbourg, France, 1995. It was speculated that introduction of the related mutation in *Saccharomyces cerevisiae* AspRS (E 188K) might restore its affinity for $SctRNA^{Asp}_{CUA}$. It was determined that the *Saccharomyces cerevisiae* AspRS(E188K) mutant does not acylate *Escherichia coli* tRNAs, but charges $SctRNA^{Asp}_{CUA}$ with moderate efficiency as shown by in vitro aminoacylation experiments. See, e.g., M. Pastrnak, T. J. Magliery and P. G. Schultz, Helv. Chim. Acta, 83:2277 (2000).

A similar approach involves the use of a heterologous synthetase as the orthogonal synthetase but a mutant initiator tRNA of the same organism or a related organism as the orthogonal tRNA. RajBhandary and coworkers found that an amber mutant of human initiator tRNA$^{fMet}$ is acylated by Escherichia coli GlnRS and acts as an amber suppressor in yeast cells only when EcGlnRS is coexpressed. See, A. K. Kowal, C. Kohrer and U. L. RajBhandary, Proc. Natl. Acad. Sci. USA, 98:2268 (2001). This pair thus represents an orthogonal pair for use in yeast. Also, an Escherichia coli initiator tRNA$^{fMet}$ amber mutant was found that is inactive toward any Escherichia coli synthetases. A mutant yeast TyrRS was selected that charges this mutant tRNA, resulting in an orthogonal pair in Escherichia coli. See, A. K. Kowal, et al, (2001), supra.

Using the methods of the present invention, the pairs and components of pairs desired above are evolved to generate orthogonal tRNA/synthetase pairs that possess desired characteristic, e.g., that can preferentially aminoacylate an O-tRNA with an unnatural amino acid.

In certain embodiments, the O-tRNA and the O-RS can be derived by mutation of a naturally occurring tRNA and RS from a variety of organisms. In one embodiment, the O-tRNA and O-RS are derived from at least one organism, where the organism is a prokaryotic organism, e.g., Methanococcus jannaschii, Methanobacterium thermoautotrophicum, Halobacterium, Escherichia coli, A. fulgidus, P. furiosus, P. horikoshii, A. pernix, T. thermophilus, or the like. Optionally, the organism is a eukaryotic organism, e.g., plants (e.g., complex plants such as monocots, or dicots), algea, fungi (e.g., yeast, etc), animals (e.g., mammals, insects, arthropods, etc.), insects, protists, or the like. Optionally, the O-tRNA is derived by mutation of a naturally occurring tRNA from a first organism and the O-RS is derived by mutation of a naturally occurring RS from a second organism. In one embodiment, the O-tRNA and O-RS can be derived from a mutated tRNA and mutated RS. In certain embodiments, the O-RS and O-tRNA pair from a first organism is provided to a translational system of a second organism, which optionally has non-functional endogenous RS/tRNA pair with respect to the codons recognized by the O-tRNA.

The O-tRNA and the O-RS also can optionally be isolated from a variety of organisms. In one embodiment, the O-tRNA and O-RS are isolated from at least one organism, where the organism is a prokaryotic organism, e.g., Methanococcus jannaschii, Methanobacterium thermoautotrophicum, Halobacterium, Escherichia coli, A. fulgidus, P. furiosus, P. horikoshii, A. pernix, T. thermophilus, or the like. Optionally, the organism is a eukaryotic organism, e.g., plants (e.g., complex plants such as monocots, or dicots), algea, fungi (e.g., yeast, etc), animals (e.g., mammals, insects, arthropods, etc.), insects, protists, or the like. Optionally, the O-tRNA is isolated from a naturally occurring tRNA from a first organism and the O-RS is isolated from a naturally occurring RS from a second organism. In one embodiment, the O-tRNA and O-RS can be isolated from one or more library (which optionally comprises one or more O-tRNA and/or O-RS from one or more organism (including those comprising prokaryotes and/or eukaryotes).

The orthogonal tRNA-RS pair, e.g., derived from at least a first organism or at least two organisms, which can be the same or different, can be used in a variety of organisms, e.g., a second organism. The first and the second organisms of the methods of the present invention can be the same or different. As described above, the individual components of a pair can be derived from the same organism or different organisms.

For example, tRNA can be derived from a prokaryotic organism, e.g., an archaebacterium, such as Methanococcus jannaschii and Halobacterium NRC-1 or a eubacterium, such as Escherichia coli, while the synthetase can be derived from same or another prokaryotic organism, such as, Methanococcus jannaschii, Archaeoglobus fulgidus, Methanobacterium thermoautotrophicum, P. furiosus, P. horikoshii, A. pernix, T. thermophilus, Halobacterium, Escherichia coli or the like. Eukaryotic sources can also be used, e.g., plants (e.g., complex plants such as monocots, or dicots), algae, protists, fungi (e.g., yeast, etc.), animals (e.g., mammals, insects, arthropods, etc.), or the like.

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from the second organism; and, selecting for surviving cells in the first set that fail to survive in the duplicate cell set, where the first set and the duplicate cell set are grown in the presence of a selection agent, and where the surviving cells comprise the orthogonal tRNA-tRNA synthetase pair for use in the in the in vivo translation system of the second organism. In one embodiment, comparing and selecting includes an in vivo complementation assay. In another embodiment, the concentration of the selection agent is varied. The same assay may also be conducted in an in vitro system based on the second organism.

3. Generation of AARS by Mutagenesis and Selection/Screening

In certain embodiments, the AARS capable of charging a particular orthogonal tRNA with a particular unnatural amino acid can be obtained by mutagenesis of the AARS to generate a library of candidates, followed by screening and/or selection of the candidate AARS's capable of their desired function. Such orthogonal AARSs (O-RSs) and orthogonal tRNAs (O-tRNAs) may be used for in vitro/in vivo production of desired proteins with modified unnatural amino acids.

Thus methods for generating components of the protein biosynthetic machinery, such as the O-RSs, O-tRNAs, and orthogonal O-tRNA/O-RS pairs that can be used to incorporate an unnatural amino acid are provided in the present invention. Methods for selecting an orthogonal tRNA-tRNA synthetase pair for use in in vivo translation system of an organism are also provided below.

In one embodiment, methods for producing at least one recombinant orthogonal aminoacyl-tRNA synthetase (O-RS) comprise: (a) generating a library of (optionally mutant) RSs derived from at least one aminoacyl-tRNA synthetase (RS) from a first organism, e.g., a eukaryotic organism (such as a yeast), or a prokaryotic organism, such as Methanococcus jannaschii, Methanobacterium thermoautotrophicum, Halobacterium, Escherichia coli, A. fulgidus, P. furiosus, P. horikoshii, A. pernix, T. thermophilus, or the like; (b) selecting (and/or screening) the library of RSs (optionally mutant RSs) for members that aminoacylate an orthogonal tRNA (O-tRNA) in the presence of an unnatural amino acid and a natural amino acid, thereby providing a pool of active (optionally mutant) RSs; and/or, (c) selecting (optionally through negative selection) the pool for active RSs (e.g., mutant RSs) that preferentially aminoacylate the O-tRNA in the absence of the unnatural amino acid, thereby providing the at least one recombinant O-RS; wherein the at least one recombinant O-RS preferentially aminoacylates the O-tRNA with the unnatural amino acid. Recombinant O-RSs produced by the methods are also included in the present invention.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, e.g., alanine.

Libraries of mutant RSs can be generated using various mutagenesis techniques known in the art. For example, the mutant RSs can be generated by site-specific mutations, random mutations, diversity generating recombination mutations, chimeric constructs, and by other methods described herein or known in the art.

In one embodiment, selecting (and/or screening) the library of RSs (optionaly mutant RSs) for members that are active, e.g., that aminoacylate an orthogonal tRNA (O-tRNA) in the presence of an unnatural amino acid and a natural amino acid, includes: introducing a positive selection or screening marker, e.g., an antibiotic resistance gene, or the like, and the library of (optionally mutant) RSs into a plurality of cells, wherein the positive selection and/or screening marker comprises at least one codon, whose translation (optionally conditionally) depends on the ability of a candidate O-RS to charge the O-tRNA (with either a natural and/or a unnatural amino acid); growing the plurality of cells in the presence of a selection agent; identifying cells that survive (or show a specific response) in the presence of the selection and/or screening agent by successfully translate the codon in the positive selection or screening marker, thereby providing a subset of positively selected cells that contains the pool of active (optionally mutant) RSs. Optionally, the selection and/or screening agent concentration can be varied. Preferably, the cells do not contain any functional endogenous tRNA/RS pair that can help to translate the codon. The endogenous tRNA/RS pair may be disabled by gene deletion and/or RS inhibitors.

Since many essential genes of the cell likely also contain such codon that depends on the ability of O-RS to charge O-tRNA at the absence of functional endogenous RS/tRNA pair, in one embodiment, no extra positive selection markers are needed for the positive selection process—the survival of the cell can be used as a readout of the positive selection process.

In one aspect, the positive selection marker is a chloramphenicol acetyltransferase (CAT) gene. Optionally, the positive selection marker is a β-lactamase gene. In another aspect the positive screening marker comprises a fluorescent or luminescent screening marker or an affinity based screening marker (e.g., a cell surface marker).

In a similar embodiment, a cell-free in vitro system may be used to test the ability of O-RS to charge O-tRNA in a positive screening. For example, the ability of the in vitro system to translate a positive screening gene, such as a fluorescent marker gene, may depend on the ability of O-RS to charge O-tRNA to read through a codon of the marker gene.

In one embodiment, negatively selecting or screening the pool for active RSs (optionally mutants) that preferentially aminoacylate the O-tRNA in the absence of the unnatural amino acid includes: introducing a negative selection or screening marker with the pool of active (optionally mutant) RSs from the positive selection or screening into a plurality of translational system, wherein the negative selection or screening marker comprises at least one codon (e.g., codon for a toxic marker gene, e.g., a ribonuclease barnase gene), whose translation depends on the ability of a candidate O-RS to charge the O-tRNA (with a natural amino acid); and, identifying the translation system that shows a specific screening response in a first media supplemented with the unnatural amino acid and a screening or selection agent, but fail to show the specific response in a second media supplemented with the natural amino acid and the selection or screening agent, thereby providing surviving cells or screened cells with the at least one recombinant O-RS.

For example, in an in vitro negative selection system, if the successful translation of a toxin gene depends on the ability of O-RS to charge O-tRNA to read through at least one codon of the toxin gene, the ability of the system to produce the toxin protein at the presence of the unnatural amino acid, but not the presence of the natural amino acid reflects the ability of the O-RS to charge O-tRNA with unnatural amino acid but not natural amino acid.

In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a *eubacterium*, a plant, an insect, a protist, etc. In other embodiments, the screening marker comprises a fluorescent or luminescent screening marker or an affinity based screening marker.

Also, some aspects include wherein the negative selction marker comprises a ribonuclease barnase gene (which comprises at least one said codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O-RS) can further comprise: (d) isolating the at least one recombinant O-RS; (e) generating a second set of O-RS (optionally mutated) derived from the at least one recombinant O-RS; and, (f) repeating steps (b) and (c) until a mutated O-RS is obtained that comprises an ability to preferentially aminoacylate the O-tRNA. Optionally, steps (d)-(f) are repeated, e.g., at least about two times. In one aspect, the second set of mutated O-RS derived from at least one recombinant O-RS can be generated by mutagenesis, e.g., random mutagenesis, site-specific mutagenesis, recombination or a combination thereof.

The stringency of the selection/screening steps, e.g., the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the unnatural amino acid or an analogue. In one embodiment, the mutated synthetase is displayed on a cell surface, on a phage display or the like.

The methods embodied herein optionally comprise wherein the unnatural amino acid is selected from, e.g.: an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine A recombinant O-RS produced by the methods herein is also included in the current invention.

In a related aspect, methods for producing a recombinant orthogonal tRNA (O-tRNA) include: (a) generating a library of mutant tRNAs derived from at least one tRNA, from a first organism; (b) selecting (e.g., negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS (O-RS), thereby providing at least one recombinant O-tRNA; wherein the at least one recombinant O-tRNA recognizes a degenerate codon and is not efficiency recognized by the RS from the second organism and is preferentially aminoacylated by the O-RS.

In some embodiments the at least one tRNA that preferentially binds to a degenerate codon with stronger affinity than that of a corresponding endogenous tRNA. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, e.g., prokaryotes (e.g., *Methanococcus jannaschii, Methanobacteium thermoautotrophicum, Escherichia coli, Halobacterium*, etc.), eukaryotes, mammals, fungi, yeasts, archaebacteria, eubacteria, plants, insects, protists, etc. Additionally, the recombinant tRNA is optionally aminoacylated by an unnatural amino acid, wherein the unnatural amino acid is biosynthesized in vivo either naturally or through genetic manipulation. The unnatural amino acid is optionally added to a growth medium for at least the first or second organism.

Methods for generating specific O-tRNA/O-RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS (O-RS), thereby providing at least one recombinant O-tRNA. The at least one recombinant O-tRNA preferentially recognizes a degenerate codon and is not efficiently recognized by the RS from the second organism and is preferentially aminoacylated by the O-RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of an unnatural amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the unnatural amino acid, thereby providing the at least one specific O-tRNA/O-RS pair, wherein the at least one specific O-tRNA/O-RS pair comprises at least one recombinant O-RS that is specific for the unnatural amino acid and the at least one recombinant O-tRNA. Specific O-tRNA/O-RS pairs produced by the methods are included. Additionally, such methods include wherein the first and third organism are the same (e.g., *Methanococcus jannaschii*).

The organisms of the present invention comprise a variety of organism and a variety of combinations. For example, the first and the second organisms of the methods of the present invention can be the same or different. In one embodiment, the organisms are optionally a prokaryotic organism, e.g., *Methanococcus jannaschii, Methanobacterium thermoautotrophicum, Halobacterium, Escherichia coli, A. fulgidus, P. furiosus, P. horikoshii, A. pernix, T. thermophilus*, or the like. Alternatively, the organisms optionally comprise a eukaryotic organism, e.g., plants (e.g., complex plants such as monocots, or dicots), algae, protists, fungi (e.g., yeast, etc), animals (e.g., mammals, insects, arthropods, etc.), or the like. In another embodiment, the second organism is a prokaryotic organism, e.g., *Methanococcus jannaschii, Methanobacterium thermoautotrophicum, Halobacterium, Escherichia coli, A. fulgidus, Halobacterium, P. furiosus, P. horikoshii, A. pernix, T. thermophilus*, or the like. Alternatively, the second organism can be a eukaryotic organism, e.g., a yeast, a animal cell, a plant cell, a fungus, a mammalian cell, or the like. In various embodiments the first and second organisms are different.

The various methods of the invention (above) optionally comprise wherein selecting or screening comprises one or more positive or negative selection or screening, e.g., a change in amino acid permeability, a change in translation efficiency, and a change in translational fidelity. Additionally, the one or more change is optionally based upon a mutation in one or more gene in an organism in which an orthogonal tRNA-tRNA synthetase pair are used to produce such protein. Selecting and/or screening herein optionally comprises wherein at least 2 codons within one or more selection gene or within one or more screening gene are used. Such multiple codons are optionally within the same gene or within different screening/selection genes. Additionally, the optional multiple codons are optionally different codons or comprise the same type of codons.

Kits are an additional feature of the invention. For example, the kits can include one or more translation system as noted above (e.g., a cell), one or more unnatural amino acid, e.g., with appropriate packaging material, containers for holding the components of the kit, instructional materials for practicing the methods herein and/or the like. Similarly, products of the translation systems (e.g., proteins such as EPO analogues comprising unnatural amino acids) can be provided in kit form, e.g., with containers for holding the components of the kit, instructional materials for practicing the methods herein and/or the like.

VI. Nucleic Acid and Polypeptide Sequence Variants

As described herein, the invention provides for nucleic acid polynucleotide sequences and polypeptide amino acid sequences, e.g., O-tRNAs and O-RSs (and their coding polynucleotides thereof), and, e.g., compositions and methods comprising the sequences. Examples of the sequences, e.g., O-tRNAs and O-RSs are disclosed herein. However, one of skill in the art will appreciate that the invention is not limited to those sequences disclosed herein. One of skill will appreciate that the present invention also provides many related and unrelated sequences with the functions described herein, e.g., encoding an O-tRNA or an O-RS.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

VII. Exemplary Uses

Well over 100 non-coded amino acids (all ribosomally acceptable) have been reportedly introduced into proteins using other methods (see, for example, Schultz et al., *J. Am. Chem. Soc.*, 103: 1563-1567, 1981; Hinsberg et al., *J. Am. Chem. Soc.*, 104: 766-773, 1982; Pollack et al., *Science*, 242: 1038-1040, 1988; Nowak et al., *Science*, 268: 439-442, 1995) all these analogs may be used in the subject methods for efficient incorporation of these analogs into protein products. In general, the method of the instant invention can be used to incorporate amino acid analogs into protein products either in vitro or in vivo.

In another preferred embodiment, two or more analogs may be used in the same in vitro or in vivo translation system, each with its O-tRNA/O-RS pairs. This is more easily accomplished when a natural amino acid is encoded by four or more codons (such as six for Leu and Arg). However, for amino acids encoded by only two codons, one can be reserved for the natural amino acid, while the other "shared" by one or more amino acid analog(s). These analogs may resemble only one natural amino acid (for example, different Phe analogs), or resemble different amino acids (for example, analogs of Phe and Tyr).

For in vitro use, one or more O-RSs of the instant invention can be recombinantly produced and supplied to any the available in vitro translation systems (such as the commercially available Wheat Germ Lysate-based PROTEINscript-PRO™, Ambion's *E. coli* system for coupled in vitro transcription/translation; or the rabbit reticulocyte lysate-based Retic Lysate IVT™ Kit from Ambion). Optionally, the in vitro translation system can be selectively depleted of one or more natural AARSs (by, for example, immunodepletion using immobilized antibodies against natural AARS) and/or natural amino acids so that enhanced incorporation of the analog can be achieved. Alternatively, nucleic acids encoding the re-designed O-RSs may be supplied in place of recombinantly produced AARSs. The in vitro translation system is also supplied with the analogs to be incorporated into mature protein products.

Although in vitro protein synthesis usually cannot be carried out on the same scale as in vivo synthesis, in vitro methods can yield hundreds of micrograms of purified protein containing amino acid analogs. Such proteins have been produced in quantities sufficient for their characterization using circular dichroism (CD), nuclear magnetic resonance (NMR) spectrometry, and X-ray crystallography. This methodology can also be used to investigate the role of hydrophobicity, packing, side chain entropy and hydrogen bonding in determining protein stability and folding. It can also be used to probe catalytic mechanism, signal transduction and electron transfer in proteins. In addition, the properties of proteins can be modified using this methodology. For example, photo-caged proteins can be generated that can be activated by photolysis, and novel chemical handles have been introduced into proteins for the site specific incorporation of optical and other spectroscopic probes.

The development of a general approach for the incorporation of amino acid analogs into proteins in vivo, directly from the growth media, would greatly enhance the power of unnatural amino acid mutagenesis. For example, the ability to synthesize large quantities of proteins containing heavy atoms would facilitate protein structure determination, and the ability to site-specifically substitute fluorophores or photocleavable groups into proteins in living cells would provide powerful tools for studying protein function in vivo. Alternatively, one might be able to enhance the properties of proteins by providing building blocks with new functional groups, such as a keto-containing amino acid.

For in vivo use, one or more AARS of the instant invention can be supplied to a host cell (prokaryotic or eukaryotic) as genetic materials, such as coding sequences on plasmids or viral vectors, which may optionally integrate into the host genome and constitutively or inducibly express the re-designed AARSs. A heterologous or endogenous protein of interest can be expressed in such a host cell, at the presence of supplied amino acid analogs. The protein products can then be purified using any art-recognized protein purification techniques, or techniques specially designed for the protein of interest.

The above described uses are merely a few possible means for generating a transcript which encodes a polypeptide. In general, any means known in the art for generating transcripts can be employed to synthesize proteins with amino acid analogs. For example, any in vitro transcription system or coupled transcription/translation systems can be used for generate a transcript of interest, which then serves as a template for protein synthesis. Alternatively, any cell, engineered cell/cell line, or functional components (lysates, membrane fractions, etc.) that is capable of expressing proteins from genetic materials can be used to generate a transcript. These means for generating a transcript will typically include such components as RNA polymerase (T7, SP6, etc.) and co-factors, nucleotides (ATP, CTP, GTP, UTP), necessary transcription factors, and appropriate buffer conditions, as well as at least one suitable DNA template, but other components may also added for optimized reaction condition. A skilled artisan would readily envision other embodiments similar to those described herein.

The following section describes a few specific uses of the instant methods and systems for unnatural amino acid incorporation. These are meant to be illustrative and by no means limiting in any respect.

A. Long-acting Human Protein Pharmaceuticals

Most administered protein pharmaceuticals are cleared rapidly from the body, necessitating frequent, often daily injections. Thus there is considerable interest in developing long-acting protein therapeutics that are able to maintain efficacious levels in the body for long periods of time, providing patients with greater therapeutic benefits. For example, PEGylation-based drug delivery technology, the most commonly used method for increasing protein half-life, is already used in six approved drugs, with annual sales exceeding an aggregate of US$3.0 billion. The field is expanding rapidly, with over a dozen additional PEGylation-based drugs in the product pipelines of leading biotechnology and pharmaceutical companies.

PEGylation is a process to covalently attach oligosaccharides and synthetic polymers such as polyethylene glycol (PEG) site-specifically onto therapeutic protein molecules. PEGylation can significantly enhance protein half-life by shielding the polypeptide from proteolytic enzymes and increasing the apparent size of the protein, thus reducing clearance rates. Moreover, PEG conjugates can enhance protein solubility and have beneficial effects on biodistribution. The physical and pharmacological properties of PEGylated proteins are affected by the number and the size of PEG chains attached to the polypeptide, the location of the PEG sites, and the chemistry used for PEGylation. Examples of PEG conjugation to proteins include reactions of N-hydroxysuccinimidyl ester derivatized PEGs with lysine, 1,4-addition reactions of maleimide and vinylsulfone derivatized PEGs with cysteine, and condensation of hydrazide containing PEGs with aldehydes generated by oxidation of glycoproteins. When more than one reactive site is present in a protein (e.g., multiple amino or thiol groups) or reactive electrophiles are used, nonselective attachment of one or multiple PEG molecules can occur, leading to the generation of a heterogeneous mixture that is difficult to separate. The lack of selectivity and positional control in the attachment of PEG chains can lead to significant losses in biological activity and possibly enhanced immunogenicity of the conjugated protein. In fact, historically, loss of biological activity and product heterogeneity have been the two most common problems encountered in the development of long-acting protein pharmaceuticals using standard PEGylation techniques. Modification of proteins with amine-reactive PEGs typically results in drastic loss of biological activity due to modification of lysine residues located in regions of the protein important for biological activity. In certain situations, bioactivity of growth hormones may be reduced 400-fold or more. For example, bioactivity of GCSF is reduced 1,000-fold when the proteins are modified using conventional amine-PEGylation technologies (Clark et al., J. Biol. Chem. 271: 21969, 1996; Bowen et al., Exp. Hematol. 27, 425, 1999). Thus there is a need for a method that allows for the completely site-specific and irreversible attachment of PEG chains to proteins.

It would be advantageous to use advanced protein engineering technologies to create long-acting, "patient friendly" human protein pharmaceuticals, by, for example, incorporating unnatural amino acids into a drug protein, such that the engineered drug protein may achieve longer half life and/or sustained or even enhanced biological activity. Towards this end, the instant invention may be used to overcome problems such as heterogeneity and loss of activity inherent in standard amine-PEGylation techniques. Incorporating unnatural amino acids will provide unique, pre-determined sites away from the binding or the catalytic site on the target protein where PEG molecules can be site-specifically conjugated. In addition, PEG molecules may be attached to unnatural amino acids through techniques other than amine-PEGylation, thus sparing the primary amine groups of lysines from undesirable PEGylation. The major advantages of such protein engineering technologies include the creation of next-generation, proprietary proteins that:

Are homogeneously modified
Retain high biological activity and remain longer in the body
Have increased potency and stability and decreased immunogenicity
Are consistent lot to lot in biological activities These techniques may be used to enhance the half-life, efficacy, and/or safety of bio-pharmaceuticals in all areas, including the specific field of cancer, endocrinology, infectious disease, and inflammation, etc.

As an illustrative example, the copper-mediated Huisgen [3+2] cycloaddition (Tornoe et al., *J. Org. Chem.* 67: 3057, 2002; Rostovtsev et al., *Angew. Chem., Int. Ed.* 41: 596, 2002; and Wang et al., *J. Am. Chem. Soc.* 125: 3192, 2003) of an azide and an alkyne is orthogonal to all functional groups found in proteins, and forms a stable triazole linkage, this reaction can be used for the selective PEGylation of proteins. For example, Deiters et al. (*Bioorg. Med. Chem. Lett.* 14(23): 5743-5745, 2004) report a generally applicable PEGylation methodology based on the site-specific incorporation of para-azidophenylalanine into proteins in yeast. The azido group was used in a mild [3+2] cycloaddition reaction with an alkyne derivatized PEG reagent to afford selectively PEGylated protein. This strategy should be useful for the generation of selectively PEGylated proteins for therapeutic applications.

B. Enhance Half-Life of Cytokines and Growth Factors Through Increased Recycling:

Besides clearance through kidneys and the liver, a significant proportion of biotherapeutics are cleared through receptor-mediated degradation. Cytokines and growth factors, when bound to their receptors, are internalized into cellular compartments called endosomes where the receptor-ligand complexes are degraded. However, those ligands that dissociate rapidly from their receptors in the endosome are recycled back to the cell surface and avoid depletion, thereby eliciting increased half-life.

Sarkar et al. reported an approach to use natural amino acids to design a variant of G-CSF, which has reduced binding affinity for its receptor in the endosome, thus achieving a half-life of 500 hours, compared to only about 50 hours for unmodified GSCF (Sarkar et al., Nature Biotechnology 20, 908-913, 2002). Specifically, Sarkar et al. used computationally predicted histidine substitutions that switch protonation states between cell-surface and endosomal pH. Molecular modeling of binding electrostatics indicates two different single-histidine mutants that fulfill the design requirements. Experimental assays demonstrate that each mutant indeed exhibits an order-of-magnitude increase in medium half-life along with enhanced potency due to increased endocytic recycling.

However, chemistries offered by natural amino acids to modulate the binding process are limited in number and scope. In contrast, unnatural amino acids will offer a significantly better spectrum of useful chemistries, and thus more control on ligand-receptor binding affinities. Such improvements will exhibit more efficient ligand recycling, leading to increase in ligand half-life by orders of magnitudes. This method for designing cytokines and growth factors that exhibit reduced receptor-mediated degradation will be very useful in providing an alternative strategy for increasing half-life of those molecules that are not amenable to PEGylation.

Thus the instant invention provides a method to incorporate unnatural amino acids, the unique chemistries of which can be leveraged for designing the next generation of cytokines and growth factors that maintain high binding affinities for receptors on the cell surface, while having significantly lower binding affinities once they are internalized.

C. Glycosylation Through Unnatural Amino Acids

The post-translational modification of proteins by glycosylation can affect protein folding and stability, modify the intrinsic activity of proteins, and modulate their interactions with other biomolecules. See, e.g., Varki, Glycobiology 3: 97-130, 1993. Natural glycoproteins are often present as a population of many different glycoforms, which makes analysis of glycan structure and the study of glycosylation effects on protein structure and function difficult. Therefore, methods for the synthesis of natural and unnatural homogeneously glycosylated proteins are needed for the systematic understanding of glycan function, and for the development of improved glycoprotein therapeutics.

One previously known approach for making proteins having desired glycosylation patterns makes use of glycosidases to convert a heterogeneous natural glycoprotein to a simple homogenous core, onto which saccharides can then be grafted sequentially with glycosyl transferases. See, e.g., Witte et al., J. Am. Chem. Soc. 119: 2114-2118, 1997. A limitation of this approach is that the primary glycosylation sites are predetermined by the cell line in which the protein is expressed. Alternatively, a glycopeptide containing the desired glycan structure can be synthesized by solid phase peptide synthesis. This glycopeptide can be coupled to other peptides or recombinant protein fragments to afford a larger glycoprotein by native chemical ligation (see, e.g., Shin et al., J. Am. Chem. Soc. 121: 11684-11689, 1999), expressed protein ligation (see, e.g., Tolbert and Wong, J. Am. Chem. Soc. 122: 5421-5428, 2000), or with engineered proteases (see, e.g., Witte et al., J. Am. Chem. Soc. 120: 1979-1989, 1998). Both native chemical ligation and expressed protein ligation are most effective with small proteins, and necessitate a cysteine residue at the N-terminus of the glycopeptide. When a protease is used to ligate peptides together, the ligation site must be placed far away from the glycosylation site for good coupling yields. See, e.g., Witte et al., J. Am. Chem. Soc. 120: 1979-1989, 1998. A third approach is to modify proteins with saccharides directly using chemical methods. Good selectivity can be achieved with haloacetamide saccharide derivatives, which are coupled to the thiol group of cysteine (see, e.g., Davis and Flitsch, Tetrahedron Lett. 32: 6793-6796, 1991; and Macmillan et al., Org Lett 4: 1467-1470, 2002). But this method can become problematic with proteins that have more than one cysteine residue.

Accordingly, a need exists for improved methods for making glycoproteins having a desired glycosylation pattern. The instant invention fulfills this and other needs.

The instant invention provides methods for synthesis of glycoproteins. These methods involve, in some embodiments, incorporating into a protein an unnatural amino acid that comprises a first reactive group; and contacting the protein with a saccharide moiety that comprises a second reactive group, wherein the first reactive group reacts with the second reactive group, thereby forming a covalent bond that attaches the saccharide moiety to the unnatural amino acid of the protein.

Glycoproteins produced by these methods are also included in the invention.

The first reactive group is, in some embodiments, an electrophilic moiety (e.g., a keto moiety, an aldehyde moiety, and/or the like), and the second reactive group is a nucleophilic moiety. In some embodiments, the first reactive group is a nucleophilic moiety and the second reactive group is an electrophilic moiety (e.g., a keto moiety, an aldehyde moiety, and/or the like). For example, an electrophilic moiety is attached to the saccharide moiety and the nucleophilic moiety is attached to the unnatural amino acid. The saccharide moiety can include a single carbohydrate moiety, or the saccharide moiety can include two or more carbohydrate moieties.

In some embodiments, the methods further involve contacting the saccharide moiety with a glycosyl transferase, a sugar donor moiety, and other reactants required for glycosyl transferase activity for a sufficient time and under appropriate conditions to transfer a sugar from the sugar donor moiety to the saccharide moiety. The product of this reaction can, if desired, be contacted by at least a second glycosyl transferase, together with the appropriate sugar donor moiety.

In certain embodiments, the method further comprises contacting the saccharide moiety with one or more of a β1-4N-acetylglucosaminyl transferase, an α1,3-fucosyl transferase, an α1,2-fucosyl transferase, an α1,4-fucosyl transferase, a β1-4-galactosyl transferase, a sialyl transferase, and/or the like, to form a biantennary or triantennary oligosaccharide structure.

In one embodiment, the saccharide moiety comprises a terminal GlcNAc, the sugar donor moiety is UDP-Gal and the glycosyl transferase is a β-1,4-galactosyl transferase.

In one embodiment, the saccharide moiety comprises a terminal GlcNAc, the sugar donor moiety is UDP-GlcNAc and the glycosyl transferase is a β1-4N-acetylglucosaminyl transferase.

Optionally, the method further comprises contacting the product of the N-acetylglucosaminyl transferase reaction with a β1-4-mannosyl transferase and GDP-mannose to form a saccharide moiety that comprises Manβ1-4GlcNAcβ1-4GlcNAc—. Optionally, the method further comprises contacting the Manβ1-4GlcNAcβ1-4GlcNAc-moiety with an α1-3mannosyl transferase and GDP-mannose to form a saccharide moiety that comprises Manα1-3Manβ1-4GlcNAcβ1-4GlcNAc—. Optionally, the method further comprises contacting the Manα1-3Manβ1-4GlcNAcβ1-4GlcNAc-moiety with an α1-6 mannosyl transferase and GDP-mannose to form a saccharide moiety that comprises Manα1-6(Manα1-3)Manβ1-4GlcNAcβ1-4GlcNAc—.

Optionally, the method further comprises contacting the Manα1-6(Manα1-3)Manβ1-4GlcNAcβ1-4GlcNAc-moiety with a β1-2N-acetylglucosaminyl transferase and UDP-GlcNAc to form a saccharide moiety that comprises Manα1-6(GlcNAcβ1-2Manα1-3)Manβ1-4GlcNAcβ1-4GlcNAc—. Optionally, the method further comprises contacting the Manα1-6(GlcNAcβ1-2Manα1-3)Manβ1-4GlcNAcβ1-4GlcNAc-moiety with a β1-2N-acetylglucosaminyl transferase and UDP-GlcNAc to form a saccharide moiety that comprises GlcNAcβ1-2Manα1-6(GlcNAcβ1-2Manα1-3)Manβ1-4GlcNAcβ1-4GlcNAc—.

The step of incorporating into a protein an unnatural amino acid that comprises a first reactive group, in some embodiments, comprises using an orthogonal tRNA/orthogonal aminoacyl-tRNA synthetase (O-tRNA/O-RS) pair, where the O-tRNA preferentially recognizes a degenerate codon for wild-type tRNA, and incorporates the unnatural amino acid into the protein in response to the degenerate codon, and wherein the O-RS preferentially aminoacylates the O-tRNA with the unnatural amino acid. In some embodiments, the unnatural amino acid is incorporated into the polypeptide in vivo.

The invention also provides glycoproteins that comprise a saccharide moiety and a polypeptide. In certain embodiments in the glycoproteins of the invention, the saccharide moiety is attached to the polypeptide by a reaction product of a nucleophilic reaction between a first reactive group attached to an unnatural amino acid present in the polypeptide and a second reactive group attached to the saccharide moiety. In certain embodiments, the first reactive group is an electrophilic moiety (e.g., keto moiety, aldehyde moiety, and/or the like) and the second reactive group is a nucleophilic moiety.

A wide variety of suitable reactive groups are known to those of skill in the art. Such suitable reactive groups can include, for example, amino, hydroxyl, carboxyl, carboxylate, carbonyl, alkenyl, alkynyl, aldehyde, ester, ether (e.g. thio-ether), amide, amine, nitrile, vinyl, sulfide, sulfonyl, phosphoryl, or similarly chemically reactive groups. Additional suitable reactive groups include, but are not limited to, maleimide, N hydroxysuccinimide, sulfo-N-hydroxysuccinimide, nitrilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acyl-imidazole, imidazolecarbamate, vinylsulfone, succinimidylcarbonate, arylazide, anhydride, diazoacetate, benzophenone, isothiocyanate, isocyanate, imidoester, fluorobenzene, biotin and avidin.

In some embodiments, one of the reactive groups is an electrophilic moiety, and the second reactive group is a nucleophilic moiety. Either the nucleophilic moiety or the electrophilic moiety can be attached to the side-chain of the unnatural amino acid; the corresponding group is then attached to the saccharide moiety.

Suitable electrophilic moieties that react with nucleophilic moieties to form a covalent bond are known to those of skill in the art. In certain embodiments, such electrophilic moieties include, but are not limited to, e.g., carbonyl group, a sulfonyl group, an aldehyde group, a ketone group, a hindered ester group, a thioester group, a stable imine group, an epoxide group, an aziridine group, etc.

Suitable nucleophilic moieties that can react with electrophilic moiety are known to those of skill in the art. In certain embodiments, such nucleophiles include, for example, aliphatic or aromatic amines, such as ethylenediamine. In certain embodiments, the nucleophilic moieties include, but are not limited to, e.g., —NR1—NH$_2$ (hydrazide), —NR1(C=O)NR2NH2 (semicarbazide), —NR1(C=S)NR2NH2 (thiosemicarbazide), —(C=O)NR1NH2 (carbonylhydrazide), —(C=S)NR1NH2 (thiocarbonylhydrazide), —(SO$_2$)NR1NH2 (sulfonylhydrazide), —NR1NR2(C=O)NR3NH2 (carbazide), NR1NR2(C=S)NR3NH2 (thiocarbazide), —O—NH$_2$ (hydroxylamine), and the like, where each R1, R2, and R3 is independently H, or alkyl having 1-6 carbons, preferably H. In certain embodiments, the reactive group is a hydrazide, hydroxylamine, semicarbazide, carbohydrazide, a sulfonylhydrazide, or the like.

The product of the reaction between the nucleophile and the electrophilic moiety typically incorporates the atoms originally present in the nucleophilic moiety. Typical linkages obtained by reacting the aldehydes or ketones with the nucleophilic moieties include reaction products such as an oxime, an amide, a hydrazone, a reduced hydrazone, a carbohydrazone, a thiocarbohydrazone, a sulfonylhydrazone, a semicarbazone, a thiosemicarbazone, or similar functionality, depending on the nucleophilic moiety used and the electrophilic moiety (e.g., aldehyde, ketone, and/or the like) that is reacted with the nucleophilic moiety. Linkages with carboxylic acids are typically referred to as carbohydrazides or as hydroxamic acids. Linkages with sulfonic acids are typically referred to as sulfonylhydrazides or N-sulfonylhydroxylamines. The resulting linkage can be subsequently stabilized by chemical reduction.

Other aspects of the invention include methods for synthesis of a glycoprotein by incorporating into a protein an unnatural amino acid that comprises a saccharide moiety. A glycoprotein produced by the method is also a feature of the invention. In certain embodiments, the incorporating step comprises using an orthogonal tRNA/orthogonal aminoacyl-tRNA synthetase (O-tRNA/O-RS) pair, wherein the O-tRNA recognizes a degenerate codon and incorporates the unnatural amino acid that comprises a saccharide moiety (e.g., a β-O-GlcNAc-L-serine, a tri-acetyl-β-GlcNAc-serine, a tri-O-acetyl-GalNAc-α-threonine, an α-GalNAc-L-threonine, and/or the like) into the protein in response to the degenerate codon, and wherein the O-RS preferentially aminoacylates the O-tRNA with the unnatural amino acid. In one embodiment, the incorporating step is performed in vivo.

These methods can further involve contacting the saccharide moiety with a glycosyl transferase, a sugar donor moiety, and other reactants required for glycosyl transferase activity for a sufficient time and under appropriate conditions to transfer a sugar from the sugar donor moiety to the saccharide moiety. In certain embodiments, the method further comprises contacting the product of the glycosyl transferase reaction with at least a second glycosyl transferase and a second sugar donor moiety. In other words, the invention provides methods in which an amino acid-linked saccharide moiety or an unnatural amino acid that includes a saccharide moiety is further glycosylated. These glycosylation steps are preferably (though not necessarily) carried out enzymatically using, for example, a glycosyltransferase, glycosidase, or other enzyme known to those of skill in the art. In some embodiments, a plurality of enzymatic steps are carried out in a single reaction mixture that contains two or more different glycosyl transferases. For example, one can conduct a galactosylating and a sialylating step simultaneously by including both sialyl transferase and galactosyl transferase in the reaction mixture.

For enzymatic saccharide syntheses that involve glycosyl transferase reactions, the recombinant cells of the invention optionally contain at least one heterologous gene that encodes a glycosyl transferase. Many glycosyl transferases are known, as are their polynucleotide sequences. See, e.g., "The WWW Guide To Cloned Glycosyl transferases," (available on the World Wide Web). Glycosyl transferase amino acid sequences and nucleotide sequences encoding glycosyl transferases from which the amino acid sequences can be deduced are also found in various publicly available databases, including GenBank, Swiss-Prot, EMBL, and others.

In certain embodiments, a glycosyl transferase of the invention includes, but is not limited to, e.g., a galactosyl transferase, a fucosyl transferase, a glucosyl transferase, an N-acetylgalactosaminyl transferase, an N-acetylglucosaminyl transferase, a glucuronyl transferase, a sialyl transferase, a mannosyl transferase, a glucuronic acid transferase, a galacturonic acid transferase, an oligosaccharyl transferase, and the like. Suitable glycosyl transferases include those obtained from eukaryotes or prokaryotes.

An acceptor for the glycosyl transferases will be present on the glycoprotein to be modified by the methods of the invention. Suitable acceptors, include, for example, galactosyl acceptors such as Galβ1,4GalNAc-; Galβ1,3GalNAc-; lacto-N-tetraose-; Galβ1,3GlcNAc-; Galβ1,4GlcNAc-; Galβ1,3Ara-; Galβ1,6GlcNAc-; and Galβ1,4Glc-(lactose). Other acceptors known to those of skill in the art (see, e.g., Paulson et al., J. Biol. Chem. 253: 5617-5624, 1978). Typically, the acceptors form part of a saccharide moiety chain that is attached to the glycoprotein.

In one embodiment, the saccharide moiety comprises a terminal GlcNAc, the sugar donor moiety is UDP-GlcNAc and the glycosyl transferase is a β1-4N-acetylglucosaminyl transferase. In another embodiment, the saccharide moiety comprises a terminal GlcNAc, the sugar donor moiety is UDP-Gal and the glycosyl transferase is a β1-4-galactosyl transferase. Additional sugars can be added.

The glycosylation reactions include, in addition to the appropriate glycosyl transferase and acceptor, an activated nucleotide sugar that acts as a sugar donor for the glycosyl transferase. The reactions can also include other ingredients that facilitate glycosyl transferase activity. These ingredients can include a divalent cation (e.g., $Mg^{2+}$ or $Mn^{2+}$), materials necessary for ATP regeneration, phosphate ions, and organic solvents. The concentrations or amounts of the various reactants used in the processes depend upon numerous factors including reaction conditions such as temperature and pH value, and the choice and amount of acceptor saccharides to be glycosylated. The reaction medium may also comprise solubilizing detergents (e.g., Triton or SDS) and organic solvents such as methanol or ethanol, if necessary.

The invention also provides host cells (e.g., mammalian cells, yeast cells, bacterial cells, plant cells, fungal cells, archaebacterial cells, insect cells, and/or the like) that are useful for synthesizing a glycoprotein. These host cells contain: a) (optionally) an unnatural amino acid that comprises a saccharide moiety (which may be synthesized by the host cell itself, or be provided exogenously through the culture media or extracellular environment in which the host cell lives); b) an orthogonal tRNA that recognizes a degenerate codon (supra); c) an orthogonal aminoacyl tRNA synthetase (O-RS) that catalyzes attachment of the unnatural amino acid to the orthogonal tRNA; d) (optionally) a polynucleotide that encodes a glycosyl transferase; and e) a polynucleotide sequence that encodes a target/desired polypeptide and comprises at least one degenerate codon that can be preferentially recognized by the O-tRNA.

Also provided by the invention are compositions that include a translation system. The translation systems include an orthogonal tRNA (O-tRNA) and an orthogonal aminoacyl tRNA synthetase (O-RS), wherein the O-RS preferentially aminoacylates the O-tRNA with an unnatural amino acid that comprises a saccharide moiety (e.g., a β-O-GlcNAc-L-serine, a tri-acetyl-β-GlcNAc-serine, a tri-O-acetyl-GalNAc-α-threonine, an α-GalNAc-L-threonine, and/or the like), and the O-tRNA recognizes at least one degenerate codon described above.

As used herein, the term "saccharide moiety" refers to natural and unnatural sugar moieties (i.e., a unnaturally occurring sugar moiety, e.g., a sugar moiety that is modified, e.g., at one or more hydroxyl or amino positions, e.g., dehydroxylated, deaminated, esterified, etc., e.g., 2-deoxyGal is an example of an unnatural sugar moiety).

The term "carbohydrate" has the general formula $(CH_2O)_n$, and includes, but is not limited to, e.g., monosaccharides, disaccharides, oligosaccharides and polysaccharides. Oligosaccharides are chains composed of saccharide units, which are alternatively known as sugars. Saccharide units can be arranged in any order and the linkage between two saccharide units can occur in any of approximately ten different ways. The following abbreviations are used herein: Ara=arabinosyl; Fru=fructosyl; Fuc=fucosyl; Gal=galactosyl; GalNAc=N-acetylgalactosaminyl; Glc=glucosyl; GlcNAc=N-acetylglucosaminyl; Man=mannosyl; and NeuAc=sialyl (typically N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3; 2→3; 2-3; or (2,3). Natural and unnatural linkages (e.g., 1-2; 1-3; 1-4; 1-6; 2-3; 2-4; 2-6; etc.) between two sugars are included in the invention. Each saccharide is a pyranose.

The term "sialic acid" (abbreviated "Sia") refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid) (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al., J. Biol. Chem. 261: 11550-11557, 1986; Kanamori et al., J. Biol. Chem. 265: 21811-21819, 1990). Also included are 9-substituted sialic acids such as a 9-O—C11-C6 acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, Glycobiology 2: 25-40, 1992; Sialic Acids: Chemistry, Metabolism and Function, R. Schauer, Ed. (Springer-Verlag, New York (1992). The synthesis and use of sialic acid compounds in a sialylation procedure is described in, for example, international application WO 92/16640 (entire contents incorporated herein by reference).

Donor substrates for glycosyl transferases are activated nucleotide sugars. Such activated sugars generally consist of uridine and guanosine diphosphate, and cytidine monophosphate, derivatives of the sugars in which the nucleoside diphosphate or monophosphate serves as a leaving group. Bacterial, plant, and fungal systems can sometimes use other activated nucleotide sugars.

The incorporation of an unnatural amino acid, e.g., an unnatural amino acid comprising a moiety where a saccharide moiety can be attached, or an unnatural amino acid that includes a saccharide moiety, can be done to, e.g., tailor changes in protein structure and/or function, e.g., to change size, acidity, nucleophilicity, hydrogen bonding, hydrophobicity, accessibility of protease target sites, target access to a protein moiety, etc. Proteins that include an unnatural amino acid, e.g., an unnatural amino acid comprising a moiety where a saccharide moiety can be attached, or an unnatural amino acid that includes a saccharide moiety, can have enhanced, or even entirely new, catalytic or physical properties. For example, the following properties are optionally modified by inclusion of an unnatural amino acid, e.g., an unnatural amino acid comprising a moiety where a saccharide moiety can be attached, or an unnatural amino acid that includes a saccharide moiety into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one unnatural amino acid, e.g., an unnatural amino acid comprising a moiety where a saccharide moiety can be attached, or an unnatural amino acid that includes a saccharide moiety are useful for, e.g., novel therapeutics, diagnostics, catalytic enzymes, industrial enzymes, binding proteins (e.g., antibodies), and e.g., the study of protein structure and function. See, e.g., Dougherty, (2000) Unnatural Amino Acids as Probes of Protein Structure and Function, Current Opinion in Chemical Biology, 4:645-652.

In one aspect of the invention, a composition includes at least one protein with at least one, e.g., at least about two, three, four, five, six, seven, eight, nine, or at least about ten or more unnatural amino acids, e.g., an unnatural amino acid comprising a moiety where a saccharide moiety can be attached, or an unnatural amino acid that includes a saccharide moiety, and/or which include another unnatural amino acid. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein substituted with the unnatural amino acid, e.g., an unnatural amino acid comprising a moiety where a saccharide moiety can be attached, or an unnatural amino acid that includes a saccharide moiety. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different, or a combination of multiple unnatural amino acids of the same kind with at least one different unnatural amino acid.

Essentially any protein (or portion thereof) that includes an unnatural amino acid, e.g., an unnatural amino acid comprising a moiety where a saccharide moiety is attached, such as an aldehyde- or keto-derivatized amino acid, or an unnatural amino acid that includes a saccharide moiety (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate degenerate codons in a relevant translation system. Common sequence repositories for known proteins include GenBank EMBL, DDBJ and the NCBI. Other repositories can easily be identified by searching the internet.

Typically, the proteins are, e.g., at least about 60%, 70%, 75%, 80%, 90%, 95%, or at least about 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more unnatural amino acid, e.g., an unnatural amino acid comprising a moiety where a saccharide moiety is attached, or an unnatural amino acid that includes a saccharide moiety, can be found, but not limited to, those in WO 2002/085923, supra. Examples of therapeutic, diagnostic, and other proteins that can be modified to comprise one or more unnatural amino acid that comprises an amino acid, where a saccharide moiety is linked and/or an unnatural amino acid that includes a saccharide moiety include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, 1309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO", representing a preferred target for modification by the incorporation of one or more unnatural amino acid), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation of an unnatural amino acid, e.g., an unnatural amino acid comprising a moiety where a saccharide moiety can be attached, or an unnatural amino acid that includes a saccharide moiety described herein, includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more unnatural amino acid that comprises an amino acid, where a saccharide moiety is linked, and/or an unnatural amino acid that includes a saccharide moiety) include expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one unnatural amino acid, e.g., an unnatural amino acid comprising a moiety where a saccharide moiety is attached, or an unnatural amino acid that includes a saccharide moiety, are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many proteins that can be modified according to the invention are commercially available (see, e.g., the Sigma BioSciences catalogue and price list), and the corresponding protein sequences and genes and, typically, many variants thereof, are well-known (see, e.g., Genbank). Any of them can be modified by the insertion of one or more unnatural amino acid that comprises an amino acid, where a saccharide moiety is linked, or that includes an unnatural amino acid that includes a saccharide moiety according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids, specificity, reduction of LD50 or other side effects, ability to enter the body through the gastric tract (e.g., oral availability), or the like. Examples of relevant diagnostic properties include shelf half-life, stability, diagnostic activity, detectability, specificity, or the like. Examples of relevant enzymatic properties include shelf half-life, stability, specificity, enzymatic activity, production capability, or the like.

A variety of other proteins can also be modified to include one or more unnatural amino acids of the invention. For example, the invention can include substituting one or more natural amino acids in one or more vaccine proteins with an unnatural amino acid that comprises an amino acid, where a saccharide moiety is linked, or by incorporating an unnatural amino acid that includes a saccharide moiety, e.g., in proteins from infectious fungi, e.g., *Aspergillus, Candida* species; bacteria, particularly *E. coli*, which serves a model for pathogenic bacteria, as well as medically important bacteria such as Staphylococci (e.g., *aureus*), or Streptococci (e.g., *pneumoniae*); protozoa such as sporozoa (e.g., *Plasmodia*), rhizopods (e.g., *Entamoeba*) and flagellates (Trypanosoma, *Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for modification by incorporation of unnatural amino acids and/or saccharide additions of invention.

In certain embodiments, the protein or polypeptide of interest (or portion thereof) in the methods and/or compositions of the invention is encoded by a nucleic acid. Typically, the nucleic acid comprises at least one degenerate codon, at least about two, three, four, five, six, seven, eight, nine, or at least about ten or more degenerate codons.

Thus the above-described artificial (e.g., man-made, and not naturally occurring) polypeptides and polynucleotides are also features of the invention.

An artificial polynucleotide of the invention includes, e.g., (a) a polynucleotide comprising a nucleotide sequence encoding an artificial polypeptide of the invention; (b) a polynucleotide that is complementary to or that encodes a polynucleotide sequence of (a); (c) a nucleic acid that hybridizes to a polynucleotide of (a) or (b) under stringent conditions over substantially the entire length of the nucleic acid; (d) a polynucleotide that is at least about 95%, preferably at least about 98% identical to a polynucleotide of (a), (b), or (c); and, (e) a polynucleotide comprising a conservative variation of (a), (b), (c), or (d).

Because the glycopolypeptides of the invention provide a variety of new polypeptide sequences (e.g., comprising an unnatural amino acid that comprises an amino acid, where a saccharide moiety can be linked, or an unnatural amino acid that includes a saccharide moiety in the case of proteins synthesized in the translation systems herein, or, e.g., in the case of the novel synthetases, novel sequences of standard amino acids), the glycopolypeptides also provide new structural features which can be recognized, e.g., in immunological assays. Thus antibodies and antisera that are specifically immunoreactive with an artificial polypeptide of the invention are also provided. In other words, the generation of antisera, which specifically bind the polypeptides of the invention, as well as the polypeptides which are bound by such antisera, are a feature of the invention.

Such antibodies or antisera preferably have minimum, or no cross-reactivity with the wild-type version of the antigen that do not contain the unnatural amino acids.

Unnatural amino acids are generally described above. Of particular interest for making glycoproteins of the invention are unnatural amino acids in which R in Formula I includes a moiety that can react with a reactive group that is attached to a saccharide moiety, to link the saccharide moiety to a protein that includes the unnatural amino acid. Suitable R groups include, for example, keto-, azido-, hydroxyl-, hydrazine, cyano-, halo-, aminooxy-, alkenyl, alkynyl, carbonyl, ether, thiol, seleno-, sulfonyl-, borate, boronate, phospho, phosphono, phosphine, heterocyclic, enone, imine, aldehyde, ester, thioacid, thioester, hindered ester, hydroxylamine, amine, and the like, or any combination thereof. In some embodiments, the unnatural amino acids have a photoactivatable cross-linker.

In addition to unnatural amino acids that contain novel side chains, unnatural amino acids also optionally comprise modified backbone structures, e.g., as illustrated by the structures of Formula II and III:

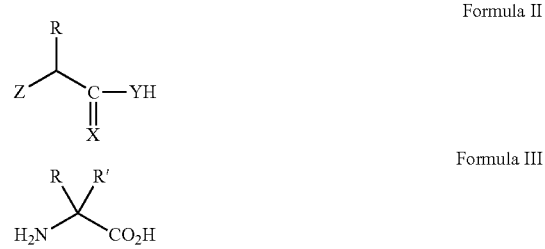

Formula II

Formula III wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3-, 4-, 6-, 7-, 8-, and 9-membered ring proline analogues, β and γ amino acids such as substituted β-alanine and γ-amino butyric acid.

For example, many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, meta-substituted, ortho-substituted, and/or para-substituted phenylalanines, wherein the substituent comprises a hydroxy group, a methoxy group, a methyl group, an allyl group, an aldehyde or keto group, or the like.

Specific examples of unnatural amino acids include, but are not limited to, p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, β-O-GlcNAc-L-serine, a tri-O-acetyl-GalNAc-α-threonine, an α-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, those listed below, or elsewhere herein, and the like. The structures of a variety of unnatural amino acids are provided in, for example, FIGS. 17, 18, 19, 26, and 29 of WO 2002/085923 (incorporated herein by reference).

Unnatural amino acids suitable for use in the methods of the invention also include those that have a saccharide moiety attached to the amino acid side chain. In one embodiment, an unnatural amino acid with a saccharide moiety includes a serine or threonine amino acid with a Man, GalNAc, Glc, Fuc, or Gal moiety. Examples of unnatural amino acids that include a saccharide moiety include, but are not limited to, e.g., a tri-O-acetyl-GlcNAcβ-serine, a β-O-GlcNAc-L-serine, a tri-O-acetyl-GalNAc-α-threonine, an α-GalNAc-L-threonine, an O-Man-L-serine, a tetra-acetyl-O-Man-L-serine, an O-GalNAc-L-serine, a tri-acetyl-O-GalNAc-L-serine, a Glc-L-serine, a tetraacetyl-Glc-L-serine, a fuc-L-serine, a tri-acetyl-fuc-L-serine, an O-Gal-L-serine, a tetra-acetyl-O-Gal-L-serine, a beta-O-GlcNAc-L-threonine, a tri-acetyl-beta-GlcNAc-L-threonine, an O-Man-L-threonine, a tetra-acetyl-O-Man-L-threonine, an O-GalNAc-L-threonine, a tri-acetyl-O-GalNAc-L-threonine, a Glc-L-threonine, a tetraacetyl-Glc-L-threonine, a fuc-L-threonine, a tri-acetyl-fuc-L-threonine, an O-Gal-L-threonine, a tetra-acetyl-O-Gal-L-serine, and the like. The invention includes unprotected and acetylated forms of the above. See also WO 03/031464 A2, entitled "Remodeling and Glycoconjugation of Peptides"; and, U.S. Pat. No. 6,331,418, entitled "Saccharide Compositions, Methods and Apparatus for their synthesis." (all incorporated herein by reference).

Many of the unnatural amino acids provided above are commercially available, e.g., from Sigma (USA) or Aldrich (Milwaukee, Wis., USA). Those that are not commercially available are optionally synthesized as provided in the examples of US 2004/138106 A1 (incorporated herein by reference) or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). See also WO 02/085923 for additional synthesis of unnatural amino acids.

For example, meta-substituted phenylalanines are synthesized in a procedure as outlined in WO 02/085923 (see, e.g., FIG. 14 of the publication). Typically, NBS (N-bromosuccinimide) is added to a meta-substituted methylbenzene compound to give a meta-substituted benzyl bromide, which is then reacted with a malonate compound to give the meta substituted phenylalanine. Typical substituents used for the meta position include, but are not limited to, ketones, methoxy groups, alkyls, acetyls, and the like. For example, 3-acetyl-phenylalanine is made by reacting NBS with a solution of 3-methylacetophenone. For more details see the examples below. A similar synthesis is used to produce a 3-methoxy phenylalanine. The R group on the meta position of the benzyl bromide in that case is —OCH$_3$. See, e.g., Matsoukas et al., J. Med. Chem., 1995, 38, 4660-4669.

In some embodiments, the design of unnatural amino acids is biased by known information about the active sites of synthetases, e.g., orthogonal tRNA synthetases used to aminoacylate an orthogonal tRNA. For example, three classes of glutamine analogs are provided, including derivatives substituted at the nitrogen of amide (1), a methyl group at the γ-position (2), and a N-Cγ-cyclic derivative (3). Based upon the x-ray crystal structure of E. coli GlnRS, in which the key binding site residues are homologous to yeast GlnRS, the analogs were designed to complement an array of side chain mutations of residues within a 10 Å shell of the side chain of glutamine, e.g., a mutation of the active site Phe233 to a small hydrophobic amino acid might be complemented by increased steric bulk at the Cγ position of Gln.

For example, N-phthaloyl-L-glutamic 1,5-anhydride (compound number 4 in FIG. 23 of WO 02/085923) is optionally used to synthesize glutamine analogs with substituents at the nitrogen of the amide. See, e.g., King & Kidd, A New Synthesis of Glutamine and of γ-Dipeptides of Glutamic Acid from Phthylated Intermediates. J. Chem. Soc., 3315-3319, 1949; Friedman & Chatterrji, Synthesis of Derivatives of Glutamine as Model Substrates for Anti-Tumor Agents. J. Am. Chem. Soc. 81, 3750-3752, 1959; Craig et al., Absolute Configuration of the Enantiomers of 7-Chloro-4 [[4-(diethylamino)-1-methylbutyl]amino]quinoline (Chloroquine). J. Org. Chem. 53, 1167-1170, 1988; and Azoulay et al., Glutamine analogues as Potential Antimalarials, Eur. J. Med. Chem. 26, 201-5, 1991. The anhydride is typically prepared from glutamic acid by first protection of the amine as the phthalimide followed by refluxing in acetic acid. The anhydride is then opened with a number of amines, resulting in a range of substituents at the amide. Deprotection of the phthaloyl group with hydrazine affords a free amino acid as shown in FIG. 23 of WO 2002/085923.

Substitution at the γ-position is typically accomplished via alkylation of glutamic acid. See, e.g., Koskinen & Rapoport, Synthesis of 4-Substituted Prolines as Conformationally Constrained Amino Acid Analogues. J. Org. Chem. 54, 1859-

1866, 1989. A protected amino acid, e.g., as illustrated by compound number 5 in FIG. 24 of WO 02/085923, is optionally prepared by first alkylation of the amino moiety with 9-bromo-9-phenylfluorene (PhflBr) (see, e.g., Christie & Rapoport, Synthesis of Optically Pure Pipecolates from L-Asparagine. Application to the Total Synthesis of (+)-Apovincamine through Amino Acid Decarbonylation and Iminium Ion Cyclization. J. Org. Chem. 1989, 1859-1866, 1985) and then esterification of the acid moiety using O-tert-butyl-N,N'-diisopropylisourea. Addition of $KN(Si(CH_3)_3)_2$ regioselectively deprotonates at the α-position of the methyl ester to form the enolate, which is then optionally alkylated with a range of alkyl iodides. Hydrolysis of the t-butyl ester and Phfl group gave the desired γ-methyl glutamine analog (Compound number 2 in FIG. 24 of WO 02/085923).

An N-Cγ cyclic analog, as illustrated by Compound number 3 in FIG. 25 of WO 02/085923, is optionally prepared in 4 steps from Boc-Asp-Ot-Bu as previously described. See, e.g., Barton et al., Synthesis of Novel α-Amino-Acids and Derivatives Using Radical Chemistry: Synthesis of L- and D-α-Amino-Adipic Acids, L-α-aminopimelic Acid and Appropriate Unsaturated Derivatives. Tetrahedron Lett. 43, 4297-4308, 1987, and Subasinghe et al., Quisqualic acid analogues: synthesis of beta-heterocyclic 2-aminopropanoic acid derivatives and their activity at a novel quisqualate-sensitized site. J. Med. Chem. 35 4602-7, 1992. Generation of the anion of the N-t-Boc-pyrrolidinone, pyrrolidinone, or oxazolidone followed by the addition of the compound 7, as shown in FIG. 25, results in a Michael addition product. Deprotection with TFA then results in the free amino acids.

In addition to the above unnatural amino acids, a library of tyrosine analogs has also been designed. Based upon the crystal structure of *B. stearothermophilus* TyrRS, whose active site is highly homologous to that of the *M. jannashii* synthetase, residues within a 10 Å shell of the aromatic side chain of tyrosine were mutated (Y32, G34, L65, Q155, D158, A167, Y32 and D158). The library of tyrosine analogs, as shown in FIG. 26 of WO 02/085923, has been designed to complement an array of substitutions to these active site amino acids. These include a variety of phenyl substitution patterns, which offer different hydrophobic and hydrogen-bonding properties. Tyrosine analogs are optionally prepared using the general strategy illustrated by WO 02/085923 (see, e.g., FIG. 27 of the publication). For example, an enolate of diethyl acetamidomalonate is optionally generated using sodium ethoxide. A desired tyrosine analog can then be prepared by adding an appropriate benzyl bromide followed by hydrolysis.

Many biosynthetic pathways already exist in cells for the production of amino acids and other compounds. While a biosynthetic method for a particular unnatural amino acid may not exist in nature, e.g., in *E. coli*, the invention provide such methods. For example, biosynthetic pathways for unnatural amino acids are optionally generated in *E. coli* by adding new enzymes or modifying existing *E. coli* pathways. Additional new enzymes are optionally naturally occurring enzymes or artificially evolved enzymes. For example, the biosynthesis of p-aminophenylalanine (as presented, e.g., in WO 02/085923) relies on the addition of a combination of known enzymes from other organisms. The genes for these enzymes can be introduced into a cell, e.g., an *E. coli* cell, by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, e.g., as developed by Maxygen, Inc., is optionally used to develop novel enzymes and pathways. See, e.g., Stemmer 1994, "Rapid evolution of a protein in vitro by DNA shuffling," Nature 370(4): 389-391; and Stemmer, 1994, "DNA shuffling by random fragmentation and reassembly: In vitro recombination for molecular evolution," Proc. Natl. Acad. Sci. USA. 91: 10747-10751. Similarly DesignPath™, developed by Genencor is optionally used for metabolic pathway engineering, e.g., to engineer a pathway to create an unnatural amino acid in *E. coli*. This technology reconstructs existing pathways in host organisms using a combination of new genes, e.g., identified through functional genomics, and molecular evolution and design. Diversa Corporation also provides technology for rapidly screening libraries of genes and gene pathways, e.g., to create new pathways.

Typically, the biosynthesis methods of the invention, e.g., the pathway to create p-aminophenylalanine (pAF) from chorismate, do not affect the concentration of other amino acids produced in the cell. For example a pathway used to produce pAF from chorismate produces pAF in the cell while the concentrations of other aromatic amino acids typically produced from chorismate are not substantially affected. Typically the unnatural amino acid produced with an engineered biosynthetic pathway of the invention is produced in a concentration sufficient for efficient protein biosynthesis, e.g., a natural cellular amount, but not to such a degree as to affect the concentration of the other amino acids or exhaust cellular resources. Typical concentrations produced in vivo in this manner are about 10 mM to about 0.05 mM. Once a bacterium is transformed with a plasmid comprising the genes used to produce enzymes desired for a specific pathway and a twenty-first amino acid, e.g., pAF, dopa, O-methyl-L-tyrosine, or the like, is generated, in vivo selections are optionally used to further optimize the production of the unnatural amino acid for both ribosomal protein synthesis and cell growth.

One protein therapeutics that can benefit from this aspect of the invention is Genzyme Corporation's (Cambridge, Mass.) Cerezyme® (imiglucerase for injection), which is an enzymatically active recombinant glucocerebrosidase for treating Gaucher's disease. Gaucher's disease is an autosomal recessive lysosomal storage disorder characterized by a deficiency in a lysosomal enzyme, glucocerebrosidase ("GCR"), which hydrolyzes the glycolipid glucocerebroside. In Gaucher's patients, deficiency in this enzyme causes the lycolipid glucocerebroside, which arises primarily from degradation of glucosphingolipids from membranes of white blood cells and senescent red blood cells, to accumulate in large quantities in lysosomes of phagocytic cells, mainly in the liver, spleen and bone marrow. Clinical manifestations of the disease include splenomegaly, hepatomegaly, skeletal disorders, thrombocytopenia and anemia.

Prior treatments for patients suffering from this disease include administration of analgesics for relief of bone pain, blood and platelet transfusions, and in severe cases, splenectomy. Joint replacements may be necessary for patients who experience bone erosion. Brady (New England Journal of Medicine 275: 312, 1966) proposed enzyme replacement therapy with GCR as a treatment for Gaucher's disease. However, Furbish et al. (Biochem. Biophys. Research Communications 81: 1047, 1978) observed that infused human placental GCR does not reach the site at which it is active, namely lysosomes of cells of the reticuloendothelial system, but rather is taken up by hepatocytes. Furbish et al. (Biochem. Biophys. Acta 673: 425, 1981) improved delivery of human placental GCR to phagocytic cells by treating the GCR sequentially with neuraminidase, β-galactosidase and β-N-acetylhexosaminidase, and demonstrated that the treated GCR was taken up more efficiently by rat Kupffer cells than untreated protein. Sorge et al. (Proc. Nat'l. Acad. Sci., USA 82: 7289, 1985) and Tsuji et al. (J. Biol. Chem. 261: 50, 1986) describe cloning and sequencing of a gene encoding human GCR.

Genzyme Corp. developed and produced in mammalian cell culture (CHO, or Chinese Hamster Overy cells) a recombinant analogue of the human enzyme β-Glucocerebrosidase (β-D-glucosyl-N-acylsphingosine glucohydrolase, E.C. 3.2.1.45), which it calls Cerezyme® (imiglucerase for injection). Purified imiglucerase is a monomeric glycoprotein of 497 amino acids, containing 4 N-linked glycosylation sites (Mr=60,430). Imiglucerase differs from placental glucocerebrosidase by one amino acid at position 495, where histidine is substituted for arginine. The oligosaccharide chains at the glycosylation sites have been modified to terminate in mannose sugars. The modified carbohydrate structures on imiglucerase are somewhat different from those on placental glucocerebrosidase. These mannose-terminated oligosaccharide chains of imiglucerase are specifically recognized by endocytic carbohydrate receptors on macrophages, the cells that accumulate lipid in Gaucher disease. See U.S. Pat. Nos. 5,236,838 and 5,549,892. In clinical trials, Cerezyme® improved anemia and thrombocytopenia, reduced spleen and liver size, and decreased cachexia to a degree similar to that observed with Ceredase® (alglucerase injection).

One problem of Cerezyme® (imiglucerase for injection) is its apparent serum half-life. During one-hour intravenous infusions of four doses (7.5, 15, 30, 60 U/kg) of Cerezyme® (imiglucerase for injection), steady-state enzymatic activity was achieved by 30 minutes. However, following infusion, plasma enzymatic activity declined rapidly with a half-life ranging from 3.6 to 10.4 minutes. Plasma clearance ranged from 9.8 to 20.3 mL/min/kg (mean±S.D., 14.5±4.0 mL/min/kg). The volume of distribution corrected for weight ranged from 0.09 to 0.15 L/kg (0.12±0.02 L/kg). These variables do not appear to be influenced by dose or duration of infusion. The pharmacokinetics of Cerezyme® do not appear to be different from placental-derived alglucerase (Ceredase®). This necessitates the need to administer relatively large amounts of Cerezyme® (imiglucerase for injection) to the patient, especially in long-term treatment, which can become quite expensive. In fact, Cerezyme® treatment generally requires life-long, intravenous infusions at least once every 2 weeks, making it inconvenient for most patients, and prohibitively expensive (and therefore unavailable) to patients in poor countries.

The instant invention can be used to incorporate unnatural amino acid(s) into the recombinant Cerezyme® and increase its half-life without substantially lose its intended bioactivity, thus significantly reduce the amount of enzymes needed per patient in a given amount of treatment period. This will reduce the cost and/or increase profit margin, resulting in a cheaper, if not better therapeutics that is more affordable.

D. Multi-Drug Immunoconjugates

The global market for monoclonal antibody therapeutics reached a total of $7.2 billion in 2003. The market has been growing at an impressive compound average annual growth rate of 53% over the previous five years, and is estimated to reach US$26 billion by the end of the decade (average annual growth rate of 18%).

More than 270 industry antibody R&D projects related to cancer therapy have been identified. Among them, there are almost 100 industry related R&D projects utilizing conjugated antibodies as a therapeutic strategy, some are already in different phases of clinical development (see Monoclonal Antibody Therapeutics: Current Market Dynamics & Future Outlook, Research and Markets Ltd, 2004; Improved Monoclonals on the Rise, Research and Markets Ltd, 2004; Anticancer Monoclonal Antibody Database, Bioportfolio, 2003).

Immunoconjugation may be used to increase the therapeutic efficacies of antibodies. However, current technologies allow attachment of only a single type of drug to an antibody. This is primarily due to the limitations in the scope of chemistries available in the set of natural amino acids, which do not allow precise control over the immunoconjugation processes.

Attempts to attach multiple drugs on an antibody using current technologies lead to significant heterogeneity from molecule to molecule, and inconsistencies from lot to lot. This is far from ideal in the context of tumor therapies, since the best strategy to treat tumors is frequently through using cocktails of drugs.

Unnatural amino acids can be used to provide a wide variety of new chemistries to attach drugs site-specifically, thus enabling the provision of tumor-targeted, multi-drug regimens to cancer patients. For example, the instant methods can be used to produce immunoconjugates either by attaching a single type of drug site-specifically on to antibodies and antibody fragments to overcome issues related to heterogeneity, or by attaching multiple drug-types site-specifically on to antibodies and antibody fragments in a stoichiometrically controlled manner. In other words, the methods of the instant invention can be used to design a novel class of immunoconjugates that carry a combination of drugs that can be delivered simultaneously and specifically to the tumor, where the therapeutic molecules in the medicament are highly homogeneous, with lot to lot consistency. The major advantages of such immunoconjugates include:

Simultaneous targeted delivery of multiple drugs that act synergistically in killing tumor cells Combining drugs that act in different phases of the cell cycle to increase the number of cells exposed to cytotoxic effects Focused delivery of the cytotoxic agents to tumor cells maximizing its antitumor effect Minimized exposure to normal tissue Precise control over drug payloads and drug ratios leading to homogenous final products For example, EP0328147B1 describes novel immunoconjugates, methods for their production, pharmaceutical compositions and method for delivering cytotoxic anthracyclines to a selected population of cells desired to be eliminated. More particularly, the invention relates to immunoconjugates comprised of an antibody reactive with a selected cell population to be eliminated, the antibody having a number of cytotoxic anthracycline molecules covalently linked to its structure. Each anthracycline molecule is conjugated to the antibody via a linker arm, the anthracycline being bound to that linker via an acid-sensitive acylhydrazone bond at the 13-keto position of the anthracycline. A preferred embodiment of the invention relates to an adriamycin immunoconjugate wherein adriamycin is attached to the linker arm through an acylhydrazone bond at the 13-keto position. The linker additionally contains a disulfide or thioether linkage as part of the antibody attachment to the immunoconjugate. The immunoconjugates and methods of the invention are useful in antibody-mediated drug delivery systems for the preferential killing of a selected cell population in the treatment of diseases such as cancers and other tumors, non-cytocidal viral or other pathogenic infections, and autoimmune disorders.

In that particular example, the antibody-drug linkage is limited to a disulfide or a thioether bond, which in general will likely lead to the heterogeneity and inconsistency problem described above. And there is few control, if any, about the attachment of multiple drugs. The instant invention allows multiple unnatural amino acids with different chemistry to be incorporated at different pre-determined positions of the antibody or its fragment, thus allowing multiple drug molecules to be site-specifically attached to the immunoconjugate.

Thus the invention provides an immunoconjugate comprising an antibody (or its functional fragment) specific for a target (e.g., a target cell), the antibody (or fragment or functional equivalent thereof) conjugated, at specific, pre-determined positions, with two or more therapeutic molecules, wherein each of the positions comprise an unnatural amino acid. In certain embodiments, the antibody fragments are $F(ab)_2$, Fab', Fab, or Fv fragments.

In certain embodiments, the two or more therapeutic molecules are the same. In certain embodiments, the two or more therapeutic molecules are different. In certain embodiments, the therapeutic molecules are conjugated to the same unnatural amino acids. In certain embodiments, the therapeutic molecules are conjugated to different unnatural amino acids.

In certain embodiments, the nature or chemistry of the unnatural amino acid/therapeutic molecule linkage allows cleavage of the linkage under certain conditions, such as mild or weak acidic conditions (e.g., about pH 4-6, preferably about pH5), reductive environment (e.g., the presence of a reducing agent), or divalent cations, and is optionally accelerated by heat. See EP0318948A2.

In certain embodiments, the unnatural amino acid(s) and/or the thrapeutic molecule comprises a chemically reactive moiety. The moiety may be strongly electrophilic or nucleophilic and thereby be available for reacting directly with the therapeutic molecule or the antibody or fragment thereof. Alternatively, the moiety may be a weaker electrophile or nucleophile and therefore require activation prior to the conjugation with the therapeutic molecule or the antibody or fragment thereof. This alternative would be desirable where it is necessary to delay activation of the chemically reactive moiety until an agent is added to the molecule in order to prevent the reaction of the agent with the moiety. In either scenario, the moiety is chemically reactive, the scenarios differ (in the reacting with antibody scenario) by whether following addition of an agent, the moiety is reacted directly with an antibody or fragment thereof or is reacted first with one or more chemicals to render the moiety capable of reacting with an antibody or fragment thereof. In certain embodiments, the chemically reactive moiety includes an amino group, a sulfhydryl group, a hydroxyl group, a carbonyl-containing group, or an alkyl leaving group.

In certain embodiments, the therapeutic molecule is conjugated to the antibody through a linker/spacer (e.g., one or more repeats of methylene ($—CH_2—$), methyleneoxy ($—CH_2—O—$), methylenecarbonyl ($—CH_2—CO—$), amino acids, or combinations thereof).

Therapeutic molecules may include drugs, toxins (e.g., icin, abrin, diptheria toxin, and *Pseudomonas* exotoxin A), biological response modifiers, radiodiagnostic compounds, radiotherapeutic compounds, and derivatives or combinations thereof.

The invention also provides the use of the subject translation systems, host cells, and methods for generating such immunoconjugates.

E. Multiprotein Complexes

Unnatural amino acids can also be used to join two or more proteins or protein sub-units with unique functionalities. For example, bispecific antibodies may be generated by linking two antibodies (or functional parts thereof or derivatives thereof, such as Fab, Fab', Fd, Fv, scFv fragments, etc.) through unnatural amino acids incorporated therein.

Although the electrophilic moiety (e.g., a keto moiety, an aldehyde moiety, and/or the like) and nucleophilic moiety described above in subsection C are introduced in the context of attaching sugar moieties to proteins, the same set of electrophilic and nucleophilic moieties may be used to join two protein molecules, such as two antibody molecules.

Thus the instant invention provides methods for synthesis of multi-protein conjugates. These methods involve, in some embodiments, incorporating into a first protein (e.g., a first antibody) a first unnatural amino acid that comprises a first reactive group; and contacting the first protein with a second protein (e.g., a second antibody) comprising a second unnatural amino acid that comprises a second reactive group, wherein the first reactive group reacts with the second reactive group, thereby forming a covalent bond that attaches the second protein to the first protein.

The first reactive group is, in some embodiments, an electrophilic moiety (e.g., a keto moiety, an aldehyde moiety, and/or the like), and the second reactive group is a nucleophilic moiety. In some embodiments, the first reactive group is a nucleophilic moiety and the second reactive group is an electrophilic moiety (e.g., a keto moiety, an aldehyde moiety, and/or the like). For example, an electrophilic moiety is attached to the unnatural amino acid of the first Ab, and the nucleophilic moiety is attached to the unnatural amino acid of the second Ab.

Different functional domains of different proteins may be linked together through similar fashion to create novel proteins with novel functions (e.g., novel transcription factors with unique combination of DNA binding and transcription activation domains; novel enzymes with novel regulatory domains, etc.).

F. pH-Sensitive Binding

Many protein interactions are pH-sensitive, in the sense that binding affinity of one protein for its usual binding partner may change as environmental pH changes. For example, many ligands (such as insulin, interferons, growth hormone, etc.) bind their respective cell-surface receptors to elicit signal transduction. The ligand-receptor complex will then be internalized by receptor-mediated endocytosis, and go through a successive series of more and more acidic endosomes. Eventually, the ligand-receptor interaction is weakened at a certain acidic pH (e.g., about pH 5.0), and the ligand dissociates from the receptor. Some receptors (and perhaps some ligands) may be recycled back to cell surface. There, they may be able to bind their respective normal binding partners.

If the pH-sensitive binding can be modulated such that the ligand-receptor complex can be dissociated at a relatively higher pH, then certain ligands may be dissociated earlier from their receptors, and become preferentially recycled to cell surface rather than be degraded. This will result in an increased in vivo half-life of such ligands, which might be desirable since less insulin may be needed for the same (or better) efficacy in diabete patients.

In other situations, it might be desirable to modulate the pH-sensitive binding by favoring binding at a lower pH.

For example, monoclonal antibodies are generally very specific for their targets. However, in many applications, such as in cancer therapy, they tend to elicit certain side effects by, for example, binding to non-tumor tissues. One reason could be that the tumor targets against which monoclonal antibodies are raised are not specifically expressed on tumor cells, but are also expressed (although may be in smaller numbers) on some healthy cells. Such side effects are generally undesirable, and there is a need for antibodies with an improved specificity.

The pH of human blood is highly regulated and maintained in the range of about 7.6-7.8. On the other hand, tumor cells have an extracellular pH of 6.3-6.5, due to the accumulation of metabolic acids that are inefficiently cleared because of poor tumor vascularization. If the interaction between a tumor antigen and its therapeutic antibody can be modulated such that at low pH, the binding is favored, the tumor-antibody may have an added specificity/affinity/selectivity for those tumor antigens, even though the same tumor antigens are also occasionally found on normal tissues.

In fact, such modified antibodies may be desirable not only for cancer therapy, but also desirable for any antigen-antibody binding that may occur at a lower-than-normal level of pH.

Certainly, in the tumor antibody case, differences other than pH-sensitive binding in the extracellular region outside a tumor may also be explored to enhance tumor-specific binding. Such differences may include hypoxia condition and/or differences in the enzymes present in the extracellular environment of tumors relative to healthy tissues.

Tumor Hypoxia. Due to the increased metabolic needs of tumor cells and the fact that tumor growth exceeds that of its supporting vasculature, oxygen is often in short supply in or around tumor tissues. This leads to tumor hypoxia. Certain enzymes are expressed during hypoxia, which characteristics have been exploited to convert cancer prodrugs into active agents.

Tumor-Specific Extracellular Enzymes. Some tumor-specific enzymes that accumulate in the local extracellular tumor environment can also be investigated as prodrug activators.

While it has been known that there are differences in the micro-environment of tumors and non-tumor tissues, such differences have not been used to design and prepare antitumor antibodies with improved specificity.

The co-pending U.S. Ser. No. 11/094,625, filed on Mar. 30, 2005, describes methods, systems and reagents for regulating pH-sensitive protein interaction by incorporating non-natural amino acids into the protein (e.g. an antibody, or its functional fragment, derivative, etc.). The application also discloses specific uses in regulating pH-sensitive binding of antibodies to tumor site, by conferring enhanced tumor-specificity/selectivity. In that embodiment, the non-natural amino acids preferably have desirable side-chain pKa's, such that at below physiological pH (e.g. about pH 6.3-6.5) the non-natural amino acid confer enhanced binding to tumor antigens in acidic environments. Such non-natural amino acids can be incorporated by the subject methods and systems. The entire content of U.S. Ser. No. 11/094,625 is incorporated herein by reference.

G. Coupling of Proteins to Protein Arrays

One key technology that can enable high throughput, highly parallel analysis of polypeptides is the protein array (also called a microarray). A protein microarray typically consists of many polypeptides, each of which is attached to a solid support. The polypeptides in the microarray can be contacted with other molecules to determine, for example, whether the molecule binds to or otherwise interacts with one or more of the polypeptides in the array. Thus, it is desirable that each polypeptide in an array be attached to the solid support in a consistent orientation. Attachment of every polypeptide in the array at or near its amino terminus or its carboxyl terminus, for example, can help ensure that the active site or sites of each polypeptide are accessible to potentially interacting molecules. Moreover, the attachment of the polypeptide should not disrupt the conformation of the polypeptide, particularly if one desires to detect an activity of the immobilized polypeptides. Thus, a need exists for improved protein arrays, and methods for their preparation. The present invention fulfills these and other needs.

The instant invention provides systems and methods to produce protein arrays, which are arrays of polypeptides on solid supports. The methods and systems of the invention allow one to couple a polypeptide to a solid support in such a manner as to preserve the function of the polypeptides. The covalent or non-covalent attachment generally does not substantially affect the structure, function, or biological activity of the polypeptide. The polypeptides that are used in the arrays of the invention incorporate at least one unnatural amino acid, and where the side chain of the amino acid has a reactive group that can be used to couple the polypeptide to any suitable solid support. The arrays find use in a wide variety of applications.

The invention provides protein arrays where a polypeptide is attached to a solid support, and where the polypeptide incorporates at least one unnatural amino acid and the polypeptide is attached to the solid support by a chemical linkage that is formed from the reaction product between a first reactive group that is on the side chain of the unnatural amino acid and a second reactive group that is attached to a solid support. In this array, the first reactive group can be an electrophile, e.g., a keto or an aldehyde moiety and the second reactive group can be a nucleophilic moiety. Alternatively, the first reactive group can be a nucleophilic moiety and the second reactive group can be an electrophile, a keto or an aldehyde moiety.

A wide variety of suitable reactive groups are well known to those of skill in the art. Such suitable reactive groups can include but are not limited to, for example, amino, hydroxyl, carboxyl, carboxylate, aldehyde, ester, ether (e.g. thio-ether), amide, amine, nitrile, vinyl, sulfide, sulfonyl, phosphoryl, or similarly chemically reactive groups. Additional suitable reactive groups include, but are not limited to, maleimide, N hydroxysuccinimide, sulfo-N-hydroxysuccinimide, nitfilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acyl-imidazole, imidazolecarbamate, vinylsulfone, succinimidylcarbonate, arylazide, anhydride, diazoacetate, benzophenone, isothiocyanate, isocyanate, imidoester, fluorobenzene.

In some embodiments, one of the reactive groups is an electrophilic moiety, and the second reactive group is a nucleophilic moiety. Either the nucleophilic moiety or the electrophilic moiety can be attached to the side chain of the unnatural amino acid. That reactive group is then used in a reaction that couples the polypeptide to the solid support.

Suitable electrophilic moieties that react with nucleophilic moieties to form a covalent bond are known to those of skill in the art. Such electrophilic moieties include, but are not limited to, e.g., carbonyl group, a sulfonyl group, an aldehyde group, a ketone group, a hindered ester group, a thioester group, a stable imine group, an epoxide group, an aziridine group, etc.

The nucleophilic moiety used in the reactive group can be any suitable nucleophile, including but not limited to: aliphatic or aromatic amines, such as ethylenediamine, —NR'—NH$_2$ (hydrazide), —NR'(C=O)NR2NH2 (semicarbazide), —NR'(C=S)NR2NH2 (thiosemicarbazide), —(C=O)NR1NH2 (carbonylhydrazide), —(C=S)NR'NH$_2$ (thiocarbonylhydrazide), —(SO$_2$)NR'NH$_2$ (sulfonylhydrazide), —NR1NR2 (C=O)NRNH$_2$ (carbazide), —NR1NR2(C=S) NR'NH$_2$ (thiocarbazide), and —NH$_2$ (hydroxylamine), where each R1, R2, and R3 is independently H, or alkyl having 1-6 carbons, preferably H. In general, hydrazides, hydroxylamines, semicarbazides, sulfonylhydrazide, and carbonylhydrazides are all suitable nucleophilic moieties.

The reaction product of the nucleophile and the electrophile can be an oxime, an amide, a hydrazone, a carbohydrazone, a thiocarbohydrazone, a sulfonylhydrazone, a semicarbazone or a thiosemicarbazone. In some embodiments, the reaction product is a reduced hydrazone.

In some embodiments, one or more of the attached polypeptides on the protein array is at least about 6-50 amino acids in length, and in other embodiments, one or more of the attached polypeptides is at least about 50-100 amino acids or more in length. More specifically, at least about 50% of the attached polypeptides can be at least about 6-50 amino acids in length, or at least about 50% of the attached polypeptides are at least about 50-100 amino acids in length. In other embodiments, at least one of the attached polypeptides is a full-length polypeptide, while in other embodiments, at least one of the attached polypeptides is a fragment or portion of a full-length polypeptide.

The solid support used in the protein arrays can be any composition or format, without limitation. In one embodiment, the array is a logical array. In other embodiments, the protein array uses a microwell plate. In still other embodiments, the solid support used in the array is a bead to which is attached the polypeptide.

In some embodiments, the protein arrays of the invention have a plurality of different polypeptides. For example, a protein array can have at least about 10 different polypeptides, at least about 100 different polypeptides, or at least about 1000 different polypeptides.

In some embodiments, the polypeptides on the array carry modifications from posttranslational processing. These modifications can include, but are not limited to, glycosylation, phosphorylation, acetylation, methylation, myristoylation, prenylation, or proteolytic processing. In other embodiments, a polypeptide on the protein array is homologous to a native polypeptide.

It is not intended that the source of the polypeptide with the unnatural amino acid used on the protein array be particularly limited. The polypeptide can be produced in vivo, or can be produced synthetically. In one particular embodiment, the polypeptide with at least one unnatural amino acid is produced using a translation system that uses a nucleotide sequence with a degenerate codon, an orthogonal tRNA with an anticodon loop complementary to the degenerate codon (in Watson-Crick base pair), and an aminoacyl tRNA synthetase that preferentially aminoacylates the tRNA with an unnatural amino acid, and where the unnatural amino acid is incorporated into the polypeptide at the site of the degenerate codon.

In other embodiments, the invention provides methods for attaching the polypeptide to the solid support, thereby producing the protein array. In one aspect, the invention provides a method for attaching at least one polypeptide to a solid support, where the method uses the steps of incorporating into the polypeptide at least one unnatural amino acid that has a first reactive group and then reacting the first reactive group with a second reactive group that is attached to a solid support, thereby forming a covalent bond and attaching the polypeptide to the solid support. In this method, the first reactive group can be an electrophile, e.g., a keto or an aldehyde moiety and the second reactive group can be a nucleophilic moiety; or alternatively, the first reactive group can be a nucleophilic moiety and the second reactive group can be an electrophile, e.g., a keto or an aldehyde moiety. In a variation of this method, the first reactive group, the second reactive group, or both can comprise a chemically protected moiety, and the method can further incorporate a deprotecting step prior to the reacting step. The protection/deprotection system can be a photolabile system (e.g., photodeprotection).

The polypeptides used in this method can be produced in an in vivo translation system, or produced synthetically. The polypeptide can be subject to posttranslational processing, including but not limited to, glycosylation, phosphorylation, acetylation, methylation, myristoylation, prenylation, or proteolytic processing. The polypeptide used in the method can be a full-length polypeptide, or alternatively, can be a fragment or portion of a full-length polypeptide.

In the methods for attaching the polypeptide to the solid support, any suitable nucleophile reactive group can be used. Suitable nucleophiles include —NR1-NH$_2$ (hydrazide), —NR'(C=O)NR2NH$_2$ (semicarbazide), —NR1(C=S) NR2NH$_2$ (thiosemicarbazide), —(C=O)NR'NH$_2$ (carbonylhydrazide), —(C=S)NR1NH2 (thiocarbonylhydrazide), —(SO$_2$)NR'NH$_2$ (sulfonylhydrazide), —NRINR2(C=O) NR'NH$_2$ (carbazide), —NR'NR2(C=S)NR3NH2 (thiocarbazide), and —NH$_2$ (hydroxylamine), where each R1, R2, and R 3 is independently H, or alkyl having 1-6 carbons. The nucleophilic moiety can include any suitable nucleophile, e.g., hydrazide, hydroxylamine, semicarbazide, or carbonylhydrazide. In some methods, the second reactive group includes a linker that is attached to the solid support. That linker can be attached to the solid support after the first reactive group is reacted with the second reactive group. In other embodiments, the first reactive group includes a linker that is attached to the polypeptide.

In the methods for attaching the polypeptide to the solid support, any suitable solid support of any composition or format without limitation can be used. In one embodiment, the solid support that forms the array forms a logical array. In other embodiments, the solid supports makes use of a microwell plate. In still other embodiments, the solid support used in the array is a bead to which is attached the polypeptide.

In the methods for attaching the polypeptide to the solid support, a plurality of polypeptides can be optionally attached to the solid support. In this case, each of the polypeptides is attached to a discrete region of the solid support to form a protein array. It is not intended that the size of the polypeptides used in these methods be limited (supra).

The invention also provides biosensors that use protein arrays as described above. In one embodiment, the invention provides a biosensor that uses a polypeptide attached to a solid support by a chemical linkage that results from the reaction product between a first reactive group that is on a side chain of an unnatural amino acid incorporated into the polypeptide and a second reactive group that is attached to the solid support. In one embodiment, the polypeptide used in the biosensor is an antibody.

The invention provides methods for making a protein array, where the attachment between the polypeptide and the solid support is not limited to covalent linkages.

This method uses the steps of providing a solid support that has one or more binding or reactive moiety, providing a polypeptide of interest that incorporates one or more unnatural amino acids, and contacting the polypeptide of interest to the binding or reactive moiety, where the binding or reactive moiety binds to or reacts with the polypeptide of interest. In one embodiment of this method, the unnatural amino acid reacts with the reactive moiety to bind the protein of interest to the solid support. In another embodiment, the unnatural amino acid is bound to or uses a linker that binds to the binding moiety to bind the protein of interest to the solid support. For example, the linker can include a biotin and the binding moiety can incorporate avidin.

The invention also provides protein arrays that do not rely on covalent linkages to provide the attachment between the polypeptide and the solid support. These arrays incorporate a polypeptide attached to a solid support, wherein the polypeptide incorporates at least one unnatural amino acid and the polypeptide is attached to the solid support by a linkage that uses a non-covalent interaction between a chemical moiety on the side chain of the unnatural amino acid and a second chemical moiety that is attached to a solid support. The non-covalent interaction can be an ionic interaction or a van der Waals interaction. For example, unnatural amino acid side chains with suitable acidic groups will form strong associations with solid supports carrying hydroxyl or other negatively charged groups. In other variations of this system, other types of moieties having a strong affinity for each other can be incorporated into the reactive groups on the unnatural amino acid side chains and the solid support. For example, an unnatural amino acid side chain can be coupled with biotin through a suitable reactive group, while the solid support can be coated with avidin, resulting in an extremely strong non-covalent binding between the polypeptide containing the unnatural amino acid and the solid support.

Another example of a non-covalent interaction between the polypeptide and the solid phase that finds particular use with the invention is the use of specific antibodies. In this embodiment, an antibody can be raised against an unnatural amino acid side chain. If that unnatural amino acid is incorporated into a polypeptide, and that antibody is affixed to a solid phase, e.g., in a microwell plate array, the antibody then serves as an amino acid specific tether to bind the polypeptide to the solid phase.

The invention also provides a method for attaching at least one polypeptide to a solid support, where the method includes incorporating into the polypeptide at least one unnatural amino acid having a side chain with a first chemical moiety, providing a solid support with a second chemical moiety, providing a linker, where the linker has a third and fourth chemical moieties, and combining the polypeptide, the linker, and the solid support under conditions whereby the first chemical moiety on the polypeptide attaches to the third chemical moiety on the linker and the second chemical moiety on the solid support attaches to the fourth chemical moiety on the linker, thereby forming a bridge between the polypeptide and the solid support and attaching the polypeptide to the solid support.

In some embodiments of this method, the linker is reacted with the polypeptide prior to reaction with the solid support, or alternatively, is reacted with the solid support prior to reaction with the polypeptide. The attachment between the first chemical moiety on the polypeptide and the third chemical moiety on the linker can be covalent or non-covalent. In the case where the attachment between the first and third chemical moieties is non-covalent, cognate moieties, such as avidin and biotin can be use for coupling.

In other embodiments, the attachment between the second chemical moiety on the solid support and the fourth chemical moiety on the linker can be covalent or noncovalent. In the case where it is non-covalent, an avidin-biotin-coupling can be used.

As used herein in this aspect of the invention, the term "solid support" refers to a matrix of material in a substantially fixed arrangement that can be functionalized to allow synthesis, attachment or immobilization of polypeptides, either directly or indirectly. The term "solid support" also encompasses terms such as "resin" or "solid phase." A solid support may be composed of polymers, e.g., organic polymers such as polystyrene, polyethylene, polypropylene, polyfluoroethylene, polyethyleneoxy, and polyacrylamide, as well as copolymers and grafts thereof. A solid support may also be inorganic, such as glass, silica, silicon, controlled-pore-glass (CPG), reverse-phase silica, or any suitable metal. In addition to those described herein, it is also intended that the term "solid support" include any solid support that has received any type of coating or any other type of secondary treatment, e.g. Langmuir-Blodgett films, self-assembled monolayers; (SAM), sol-gel, or the like.

As used herein, "array" or "microarray" is an arrangement of elements (e.g., polypeptides), e.g., present on a solid support and/or in an arrangement of vessels. While arrays are most often thought of as physical elements with a specified spatial-physical relationship, the present invention can also make use of "logical" arrays, which do not have a straightforward spatial organization. For example, a computer system can be used to track the location of one or several components of interest that are located in or on physically disparate components. The computer system creates a logical array by providing a "lookup" table of the physical location of array members. Thus, even components in motion can be part of a logical array, as long as the members of the array can be specified and located. This is relevant, e.g., where the array of the invention is present in a flowing microscale system, or when it is present in one or more microtiter trays.

Certain array formats are sometimes referred to as a "chip" or "biochip." An array can comprise a low-density number of addressable locations, e.g., 2 to about 10, 10 medium-density, e.g., about a hundred or more locations, or a high-density number, e.g., a thousand or more. Typically, the chip array format is a geometrically-regular shape that allows for facilitated fabrication, handling, placement, stacking, reagent introduction, detection, and storage. It can, however, be irregular. In one typical format, an array is configured in a row and column format, with regular spacing between each location of member sets on the array. Alternatively, the locations can be bundled, mixed, or homogeneously blended for equalized treatment or sampling. An array can comprise a plurality of addressable locations configured so that each location is spatially addressable for high-throughput handling, robotic delivery, masking, or sampling of reagents. An array can also be configured to facilitate detection or quantitation by any particular means, including but not limited to, scanning by laser illumination, confocal or deflective light gathering, CCD detection, and chemical luminescence. "Array" formats, as recited herein, include but are not limited to, arrays (i.e., an array of a multiplicity of chips), microchips, microarrays, a microarray assembled on a single chip, arrays of biomolecules attached to microwell plates, or any other appropriate format for use with a system of interest.

VIII. General Techniques

General texts which describe molecular biological techniques, which are applicable to the present invention, such as cloning, mutation, cell culture and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 2002) ("Ausubel")). These texts describe mutagenesis, the use of vectors, promoters and many other relevant topics related to, e.g., the generation of orthogonal tRNA, orthogonal synthetases, and pairs thereof.

Various types of mutagenesis are used in the present invention, e.g., to produce novel sythetases or tRNAs. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, are also included in the present invention. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures as well as the following publications and references cited within: Sieber, et al., Nature Biotechnology, 19:456-460 (2001); Ling et al., Approaches to DNA mutagenesis: an overview, Anal Biochem. 254(2): 157-178 (1997); Dale et al., Oligonucleotide-directed random mutagenesis using the phosphorothioate method, Methods Mol. Biol. 57:369-374 (1996); I. A. Lorimer, I. Pastan, Nucleic Acids Res. 23, 3067-8 (1995); W. P. C. Stemmer, Nature 370, 389-91 (1994); Arnold, Protein engineering for unusual environments, Current Opinion in Biotechnology 4:450-455 (1993); Bass et al., Mutant Trp repressors with new DNA-binding specificities, Science 242:240-245 (1988); Fritz et al., Oligonucleotide-directed construction of mutations: a gapped duplex DNA procedure without enzymatic reactions in vitro, Nucl. Acids Res. 16: 6987-6999 (1988); Kramer et al., Improved enzymatic in vitro reactions in the gapped duplex DNA approach to oligonucleotide-directed construction of mutations, Nucl. Acids Res. 16: 7207 (1988); Sakamar and Khorana, Total synthesis and expression of a gene for the a-subunit of bovine rod outer segment guanine nucleotide-binding protein (transducin), Nucl. Acids Res. 14: 6361-6372 (1988); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Carter, Improved oligonucleotide-directed mutagenesis using M13 vectors, Methods in Enzymol. 154: 382-403 (1987); Kramer & Fritz Oligonucleotide-directed construction of mutations via gapped duplex DNA, Methods in Enzymol. 154:350-367 (1987); Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel et al., Rapid and efficient site-specific mutagenesis without phenotypic selection, Methods in Enzymol. 154, 367-382 (1987); Zoller & Smith, Oligonucleotide-directed mutagenesis: a simple method using two oligonucleotide primers and a single-stranded DNA template, Methods in Enzymol. 154:329-350 (1987); Carter, Site-directed mutagenesis, Biochem. J. 237:1-7 (1986); Eghtedarzadeh & Henikoff, Use of oligonucleotides to generate large deletions, Nucl. Acids Res. 14: 5115 (1986); Mandecki, Oligonucleotide-directed double-strand break repair in plasmids of Escherichia coli: a method for site-specific mutagenesis, Proc. Natl. Acad. Sci. USA, 83:7177-7181 (1986); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Wells et al., Importance of hydrogen-bond formation in stabilizing the transition state of subtilisin, Phil. Trans. R. Soc. Lond. A 317: 415-423 (1986); Botstein & Shortle, Strategies and applications of in vitro mutagenesis, Science 229:1193-1201 (1985); Carter et al., Improved oligonucleotide site-directed mutagenesis using M13 vectors, Nucl. Acids Res. 13: 4431-4443 (1985); Grundstrom et al., Oligonucleotide-directed mutagenesis by microscale 'shotgun' gene synthesis, Nucl. Acids Res. 13: 3305-3316 (1985); Kunkel, Rapid and efficient site-specific mutagenesis without phenotypic selection, Proc. Natl. Acad. Sci. USA 82:488-492 (1985); Smith, In vitro mutagenesis, Ann. Rev. Genet. 19:423-462 (1985); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Wells et al., Cassette mutagenesis: an efficient method for generation of multiple mutations at defined sites, Gene 34:315-323 (1985); Kramer et al., The gapped duplex DNA approach to oligonucleotide-directed mutation construction, Nucl. Acids Res. 12: 9441-9456 (1984); Kramer et al., Point Mismatch Repair, Cell 38:879-887 (1984); Nambiar et al., Total synthesis and cloning of a gene coding for the ribonuclease S protein, Science 223: 1299-1301 (1984); Zoller & Smith, Oligonucleotide-directed mutagenesis of DNA fragments cloned into M13 vectors, Methods in Enzymol. 100:468-500 (1983); and Zoller & Smith, Oligonucleotide-directed mutagenesis using M13-derived vectors: an efficient and general procedure for the production of point mutations in any DNA fragment, Nucleic Acids Res. 10:6487-6500 (1982). Additional details on many of the above methods can be found in Methods in Enzymology Volume 154, which also describes useful controls for trouble-shooting problems with various mutagenesis methods.

Oligonucleotides, e.g., for use in mutagenesis of the present invention, e.g., mutating libraries of synthetases, or altering tRNAs, are typically synthesized chemically according to the solid phase phosphoramidite triester method described by Beaucage and Caruthers, Tetrahedron Letts. 22(20):1859-1862, (1981) e.g., using an automated synthesizer, as described in Needham-VanDevanter et al., Nucleic Acids Res., 12:6159-6168 (1984).

In addition, essentially any nucleic acid can be custom or standard ordered from any of a variety of commercial sources, such as The Midland Certified Reagent Company, The Great American Gene Company, ExpressGen Inc., Operon Technologies Inc. (Alameda, Calif.) and many others.

The present invention also relates to host cells and organisms for the in vivo incorporation of an unnatural amino acid via orthogonal tRNA/RS pairs. Host cells are genetically engineered (e.g., transformed, transduced or transfected) with the vectors of this invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., Proc. Natl. Acad. Sci. USA 82, 5824 (1985), infection by viral vectors, high velocity ballistic penetration by small particles with the nucleic acid either within the matrix of small beads or particles, or on the surface (Klein et al., Nature 327, 70-73 (1987)). Berger, Sambrook, and Ausubel provide a variety of appropriate transformation methods.

The engineered host cells can be cultured in conventional nutrient media modified as appropriate for such activities as, for example, screening steps, activating promoters or selecting transformants. These cells can optionally be cultured into transgenic organisms.

Other useful references, e.g. for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York) and Atlas and Parks (eds.) The Handbook of Microbiological Media (1993) CRC Press, Boca Raton, Fla.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, Gene 8:81 (1979); Roberts, et al., Nature, 328:731 (1987); Schneider, B., et al., Protein Expr. Purif. 6435:10 (1995); Ausubel, Sambrook, Berger (all supra). A catalogue of Bacteria and Bacteriophages useful for cloning is provided, e.g., by the ATCC, e.g., The ATCC Catalogue of Bacteria and Bacteriophage (1992) Gherna et al. (eds.) published by the ATCC. Additional basic procedures for sequencing, cloning and other aspects of molecular biology and underlying theoretical considerations are also found in Watson et al. (1992) Recombinant DNA Second Edition Scientific American Books, NY.

EXAMPLES

This invention is further illustrated by the following examples which should not be construed as limiting. The teachings of all references, patents and published patent applications cited throughout this application, as well as the Figures are hereby incorporated by reference.

Example I tRNA and Synthetase Construction

This example illustrates the incorporation of an amino acid analog in proteins at positions encoded by codons which normally encode phenylalanine (Phe). A schematic diagram is shown in FIG. 1. Similar approaches can be used for any other analogs.

Phe is encoded by two codons, UUC and UUU. Both codons are read by a single tRNA, which is equipped with the anticodon sequence GAA. The UUC codon is therefore recognized through standard Watson-Crick base-pairing between codon and anticodon; UUU is read through a G-U wobble base-pair at the first position of the anticodon (Crick, J. Mol. Biol. 19: 548, 1966; Soll and RajBhandary, J. Mol. Biol. 29: 113, 1967). Thermal denaturation of RNA duplexes has yielded estimates of the Gibbs free energies of melting of G-U, G-C, A-U, and A-C basepairs as 4.1, 6.5, 6.3, and 2.6 kcal/mol, respectively, at 37° C. Thus the wobble basepair, G-U, is less stable than the Watson-Crick basepair, A-U. A modified tRNA$^{Phe}$ outfitted with the AAA anticodon (tRNA$^{Phe}_{AAA}$) was engineered to read the UUU codon, and was predicted to read such codons faster than wild-type tRNA$^{Phe}_{GAA}$. See FIG. 1.

Although tRNAs bearing unmodified A in the first position of the anticodon are known to read codons ending with C or U (Inagaki et al., J. Mol. Biol. 251: 486, 1995; Chen et al., J. Mol. Biol. 317: 481, 2002; Boren et al., J. Mol. Biol. 230: 739, 1993), the binding of E. coli tRNA$^{Phe}_{GAA}$ at UUC should dominate that of tRNA$^{Phe}_{AAA}$, owing to differences in the stability of A-C and G-C base pairs (see above).

We prepared a modified yeast tRNA$^{Phe}$ (ytRNA$^{Phe}_{AAA}$) with an altered anticodon loop. The first base (G34) of the tRNA$^{Phe}_{GAA}$ was replaced with A to provide specific Watson-Crick base-pairing to the UUU codon. Furthermore, G37 in the extended anticodon site was replaced with A to increase translational efficiency (see Furter, Protein Sci. 7: 419, 1998). We believe that charging of ytRNA$^{Phe}_{AAA}$ by E. coli PheRS can be ignored, because the aminoacylation rate of ytRNA$^{Phe}_{AAA}$ by E. coli PheRS is known to be <0.1% of that of E. coli tRNA$^{Phe}_{GAA}$ (Peterson and Uhlenbeck, Biochemistry 31: 10380, 1992).

Since wild-type yeast PheRS does not activate amino acids significantly larger than phenylalanine, a modified form of the synthetase with relaxed substrate specificity was prepared to accommodate L-3-(2-naphthyl)alanine (Nal).

The modified yeast PheRS (mu-yPheRS) was prepared by introduction of a Thr415Gly mutation in the α-subunit of the synthetase (Datta et al., J. Am. Chem. Soc. 124: 5652, 2002). The kinetics of activation of Nal and Phe by mu-yPheRS were analyzed in vitro via the adenosine triphosphate-pyrophosphate exchange assay. The specificity constant ($k_{cat}/K_M$) for activation of Nal by mu-yPheRS was found to be $1.55 \times 10^{-3}$ ($s^{-1} M^{-1}$), 8-fold larger than that for Phe. Therefore, when the ratio of Nal to Phe in the culture medium is high, ytRNA$^{Phe}_{AAA}$ should be charged predominantly with Nal.

Example II

Generation of a Mutant Protein Containing Nal

Murine dihydrofolate reductase (mDHFR), which contains nine Phe residues, was chosen as the test protein. The expression plasmid pQE 16 encodes mDHFR under control of a bacteriophage T5 promoter; the protein is outfitted with a C-terminal hexahistidine ($HIS_6$) tag to facilitate purification via immobilized metal affinity chromatography.

In this construct, four of the Phe residues of mDHFR are encoded by UUC codons, five by UUU. A full-length copy of the mu-yPheRS gene, under control of a constitutive tac promoter, was inserted into pQE16. The gene encoding ytRNA$^{Phe}_{AAA}$ was inserted into the repressor plasmid pREP4 (Qiagen) under control of the constitutive promoter 1 pp. *E. coli* transformants harboring these two plasmids were incubated in Phe-depleted minimal medium supplemented with 3 mM Nal and were then treated with 1 mM IPTG to induce expression of mDHFR. Although the *E. coli* strain (K10-F6) used in this study is a Phe auxotroph, (see Further, supra) a detectable level of mDHFR was expressed even under conditions of nominal depletion of Phe, probably because of release of Phe through turnover of cellular proteins. In negative control experiments, mDHFR was expressed in the absence of either ytRNA$^{Phe}_{AAA}$ or mu-yPheRS. The molar mass of mDHFR prepared in the absence of Nal, ytRNA$^{Phe}_{AAA}$, or mu-yPheRS was 23,287 Da, precisely that calculated for HIS-tagged mDHFR. However, when ytRNA$^{Phe}_{AAA}$ and mu-yPheRS were introduced into the expression strain and Nal was added to the culture medium, the observed mass of mDHFR was 23,537 Da (yield 2.5 mg/L after Ni-affinity chromatography). Because each substitution of Nal for Phe leads to a mass increment of 50 Da, this result is consistent with replacement of five Phe residues by Nal. No detectable mass shift was found in the absence of either ytRNA$^{Phe}_{AAA}$ or mu-yPheRS, confirming that the intact heterologous pair is required for incorporation of Nal. For mDHFR isolated from the strain harboring the heterologous pair, amino acid analysis indicated replacement of 4.4 of the 9 Phe residues by Nal. Without ytRNA$^{Phe}_{AAA}$ or mu-yPheRS, no incorporation of Nal into mDHFR was detected by amino acid analysis.

Figure 2A:
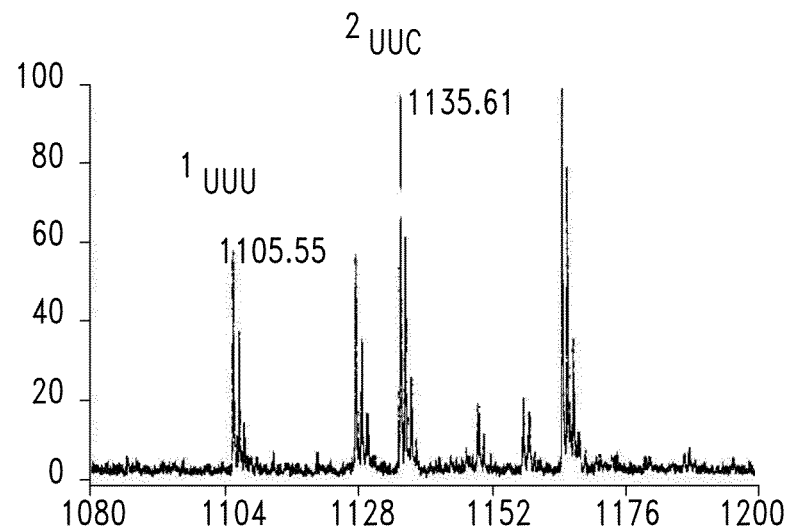
FIGS. 2A-F show the incorporation (or lack thereof) of Nal in place of Phe in several tryptic fragments of mDHFR, in response to the UUU codon. These data unambiguously establish that Nal incorporation is codon-biased to UUU.
Figure 2B:
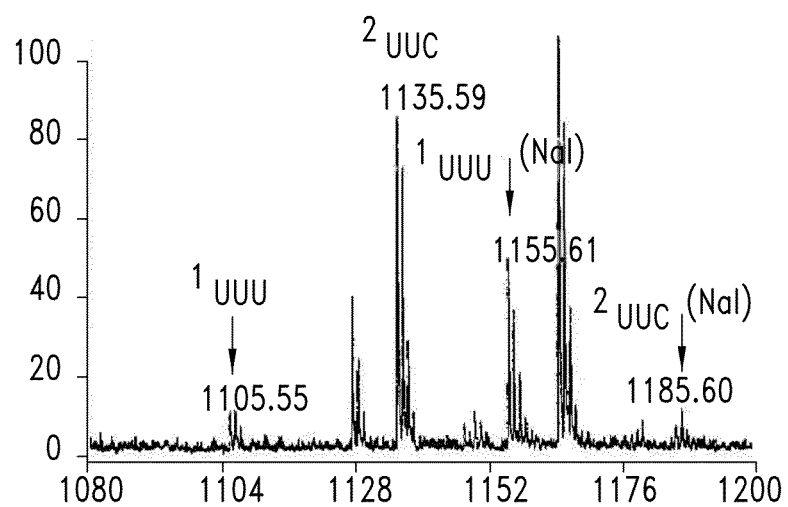
Figure 2C:
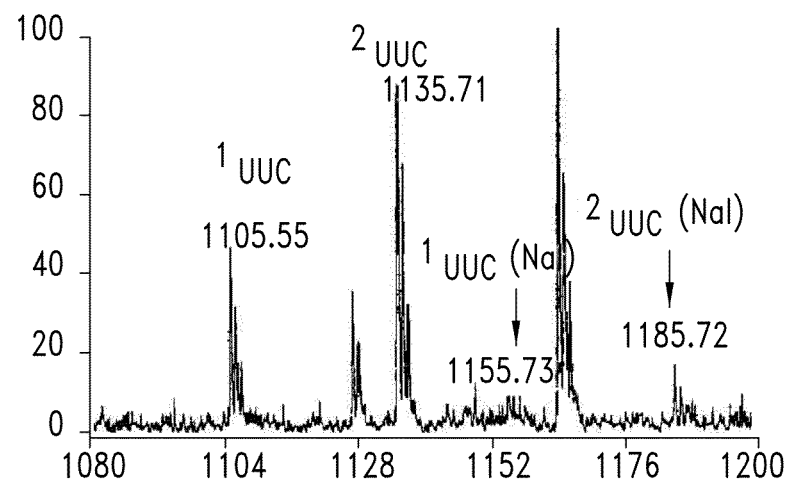
Figure 2D:
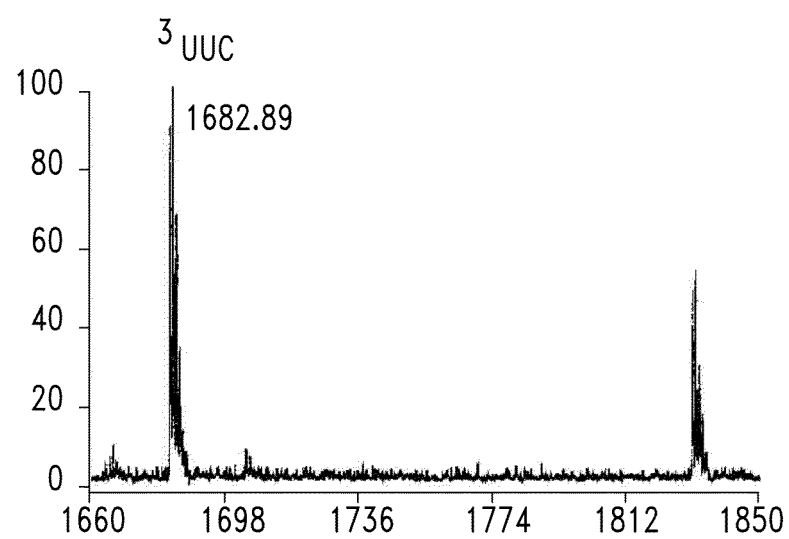
Figure 2E:
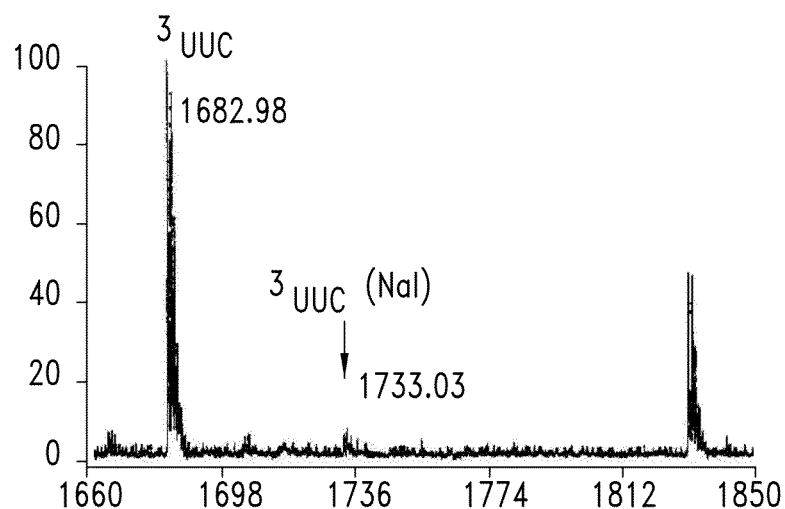

Tryptic digests of mDHFR were analyzed to determine the occupancy of individual Phe sites. Digestion of mDHFR yields peptide fragments that are readily analyzed by MALDI mass spectrometry as shown in FIG. 2. Peptide $1_{UUU}$ (residues 184-191, YKFEVYEK, SEQ ID NO: 1) contains a Phe residue encoded as UUU, whereas peptides $2_{UUC}$ (residues 62-70, KTWFSIPEK, SEQ ID NO: 2) and $3_{UUC}$ (residues 26-39, NGDLPWPPLRNEFK, SEQ ID NO: 3) each contain a Phe residue encoded as UUC. In the absence of Nal, peptide $1_{UUU}$ was detected with a monoisotopic mass of 1105.55 Da, in accord with its theoretical mass (FIG. 2A). However, when Nal was added, a strong signal at a mass of 1155.61 Da was detected, and the 1105.55 was greatly reduced in intensity (FIG. 2B). As described earlier, each substitution of Nal for Phe leads to a mass increase of 50.06 Da; the observed shift in mass is thus consistent with replacement of Phe by Nal in response to the UUU codon. Liquid chromatography—tandem mass spectrometry (LC/MS/MS) confirmed this assignment. The ratio of MALDI signal intensities, though not rigorously related to relative peptide concentrations, suggests that Nal incorporation is dominant at the UUU codon.

Similar analyses were conducted for peptides $2_{UUU}$ and $3_{UUC}$. In the absence of added Nal, the observed masses of peptides $2_{UUC}$ and $3_{UUC}$ are 1135.61 (FIG. 2A) and 1682.89 Da (FIG. 2D), respectively, as expected. Upon addition of Nal to the expression medium, the 1135.61 signal and 1682.89 signals were not substantially reduced, and only weak signals were observed at masses of 1185.60 and 1733.03 (FIGS. 2B and 2E), which would be expected for peptides $2_{UUC}$ and $3_{UUC}$ containing Nal. Nal incorporation thus appears to be rare at UUC codons under the conditions used here for protein expression.

Figure 2F:
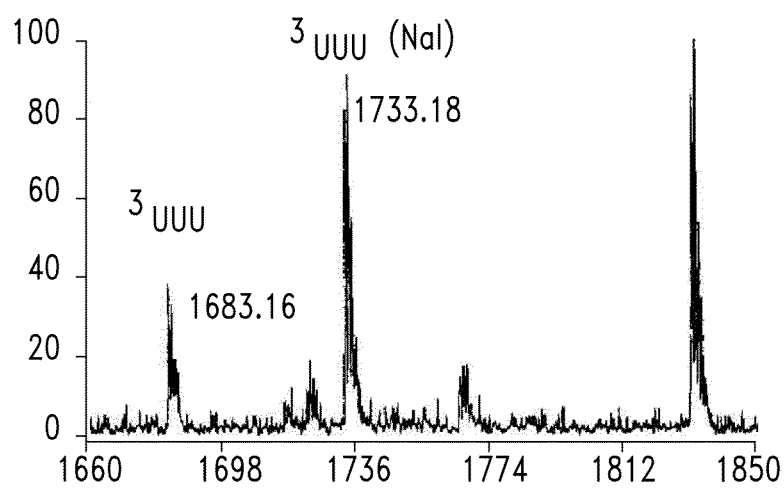

There is at least a formal possibility that the observed codon-biased incorporation of Nal might be dependent on codon context rather than, or in addition to, codon identity. MALDI sampling errors are also possible. To test these possibilities, a mutant mDHFR gene was prepared by mutating the UUU codon in peptide $1_{UUU}$ to UUC, and the UUC codon in peptide $3_{UUC}$ to UUU. In the resulting peptide $1_{UUC}$, the signal indicating incorporation of Nal was only slightly above background (FIG. 2C), whereas for peptide $3_{UUU}$, Nal is readily detected (FIG. 2F). Nal incorporation is unambiguously codon-biased to UUU.

The results described here show conclusively that a heterologous pair comprising a genetically engineered tRNA and cognate aminoacyl-tRNA synthetase can be used to break the degeneracy of the genetic code in *E. coli*.

Example III

Application to Degenerate Leucine-Encoding Codons

Figure 3:
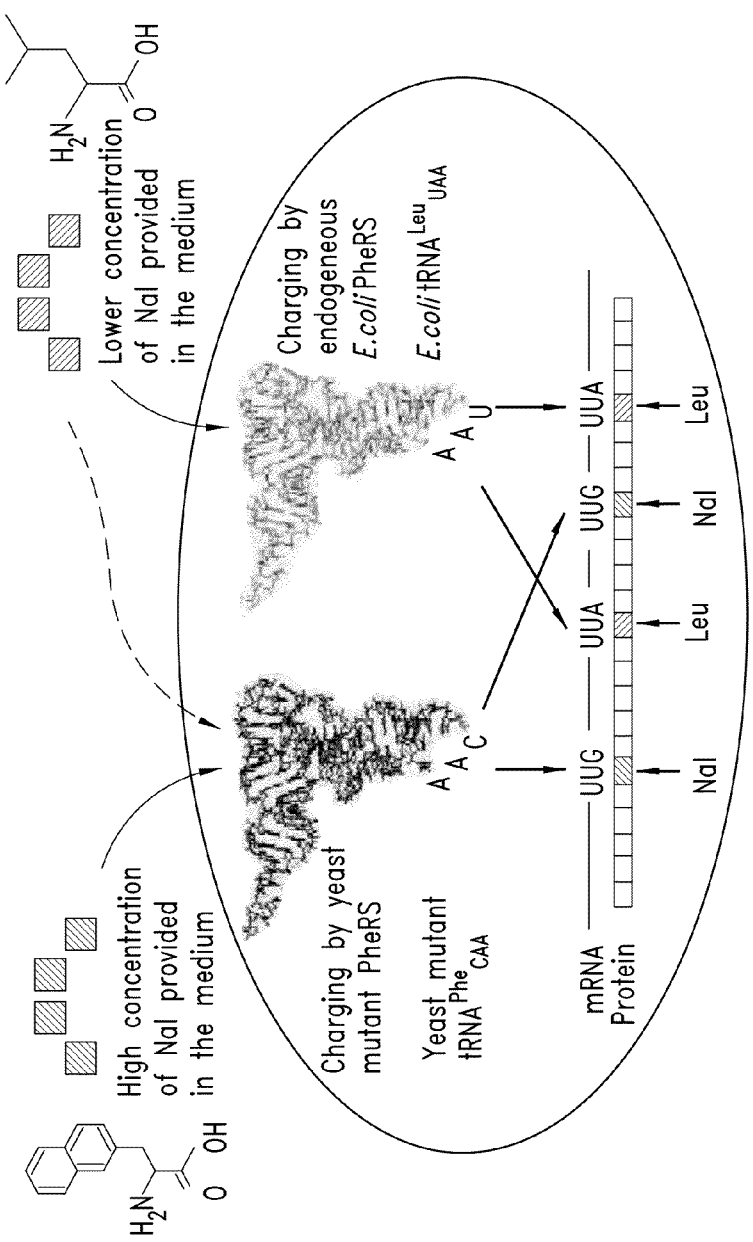
FIG. 3 shows a schematic diagram for multiple-site-specific incorporation of unnatural amino acid into the UUG codon.

In this example, multiple-site-specific incorporation of an unnatural amino acid into murine dihydrofolate reductase (mDHFR) in response to a sense codon was realized by use of an *E. coli* strain outfitted with a yeast transfer RNA (ytRNA$^{Phe}_{CAA}$) capable of Watson-Crick base-pairing with the leucine (Leu) codon UUG. ytRNA$^{Phe}_{CAA}$ was charged with L-3-(2-naphthyl)alanine (Nal) by a co-expressed modified yeast phenylalanine tRNA synthetase. See schematic diagram in FIG. 3. Mass spectrometric analysis of tryptic digests of mDHFR showed that the UUG codon was partially re-assigned to Nal, whereas the other five Leu codons remained assigned to Leu.

Incomplete occupancy of the UUG codon by Nal is due at least in part to competition with leucine-charged *E. coli* tRNA$^{Leu}$s. In an attempt to reduce competition by *E. coli* tRNA$^{Leu}$s, use of a mutant *E. coli* strain lacking tRNA$^{Leu}_{CAA}$ and addition of an *E. coli* leucyl-tRNA synthetase (LeuRS) inhibitor were tested. A Phe/Leu double auxotrophic strain derived from the tRNA$^{Leu}_{CAA}$-deficient strain XA106 (CGSC at Yale) was tested for incorporation of Nal at the UUG codon. Introduction of ytRNA$^{Phe}_{CAA}$ into a mutant host lacking tRNA$^{Leu}_{CAA}$ did not enhance the occupancy of the UUG sites by Nal, consistent with earlier proposals that *E. coli* tRNA$^{Leu}_{CAA}$ is rarely involved in protein translation (Holmes, W. M.; Goldman, E.; Miner, T. A.; Hatfield, G. W. *Proc. Natl. Acad. Sci. USA* 74: 1393-1397, 1977). 4-Aza-DL-leucine (AZL) is a competitive inhibitor of *E. coli* LeuRS, and does not progress to the azaleucyl-adenylate in vitro. It resulted in enhanced occupancy of the UUG codon by Nal. The results described here demonstrate conclusively that the concept of breaking the degeneracy of the genetic code is quite general.

Figure 4C:
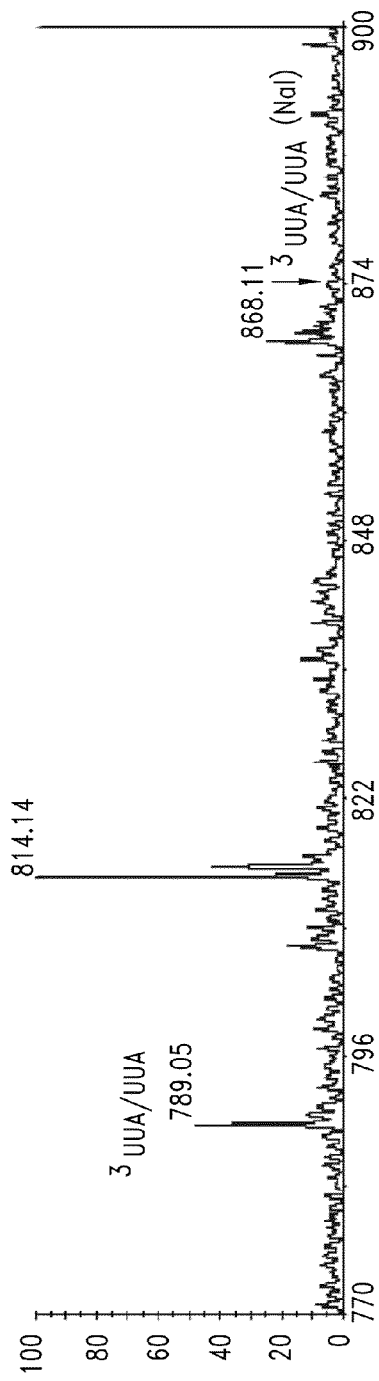
Figure 4D:
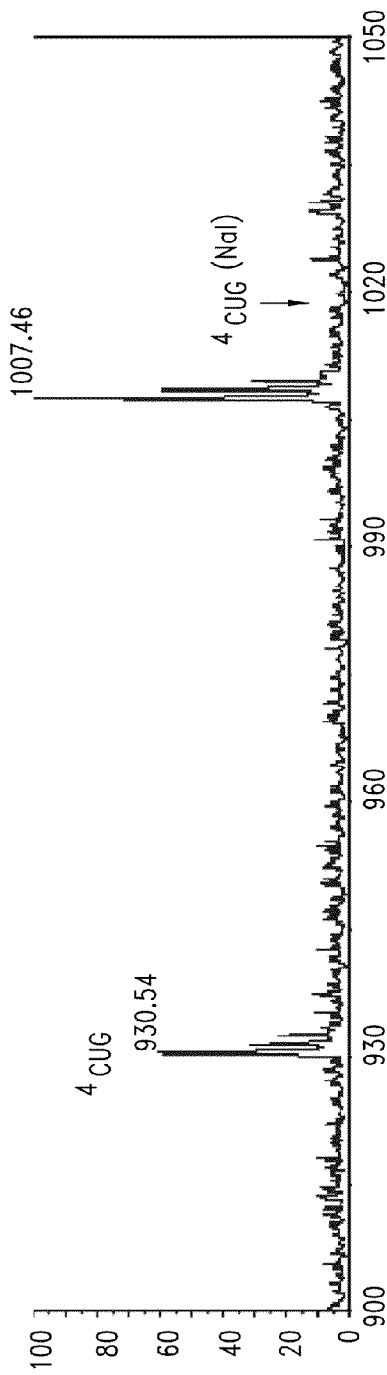

Replacement of Leu by Nal was detected in MALDI mass spectra of tryptic fragments of mDHFR (FIG. 4). Peptide $1_{UUG}$ (residues 145-162, IMQEFESDTFFPEIDL$_{UUG}$GK, SEQ ID NO: 4) contains a Leu residue encoded by UUG, whereas Peptide $1_{UUG}$ (Nal) refers to the form of the peptide containing Nal in place of Leu. Peptides $2_{UUG}$ (residues 3-25, GSGIMVRPL$_{UUG}$NSIVAVSQNMGIGK, SEQ ID NO: 5), and $4_{CUG}$ (residues 54-61, QNL$_{CUG}$VIMGR, SEQ ID NO: 6) were designated similarly. Peptide $3_{UUG/UUA}$ (residues 99-105, SL$_{UUG}$DDAL$_{UUA}$R, SEQ ID NO: 7) contains two Leu residues encoded as UUG and UUA, respectively, while Peptide $3_{UUA/UUA}$ contains two Leu residues encoded as only UUA. Upon addition of Nal, the masses of peptide fragments 1-3 shift by 84.06 ($1_{UUG}$), 83.89 ($2_{UUG}$), and 84.18 ($3_{UUG/UUA}$) mass units, respectively, as expected for replacement of Leu by the larger Phe analog (Nal). The tandem mass spectrum of Peptide $3_{UUG/UUA}$ (Nal) confirmed that only the Leu encoded by UUG was replaced by Nal. Furthermore, Nal incorporation was not detected when UUG was mutated to UUA in Peptide 3. No signal corresponding to Peptide $4_{CUG}$ (Nal) was detected, whereas that corresponding to Peptide $4_{CUG}$ was detected at 904.54 mass units. These data confirm that incorporation of Nal is strongly biased to UUG.

Replacement of Leu by Nal was detected in MALDI mass spectra of tryptic fragments of mDHFR expressed in $tRNA^{Leu}{}_{CAA}$-harboring E. coli (a) and $tRNA^{Leu}{}_{CAA}$-deficient E. coli (b). Peptide $3_{UUG/UUA}$ (residues 99-105, $SL_{UUG}DDAL_{UUA}R$, SEQ ID NO: 7) contains two Leu residues encoded as UUG and UUA, respectively. Upon addition of Nal, the masses of these fragments shift in accord with the mass difference between Nal and Leu, indicating that incorporation had occurred.

Figure 5A:
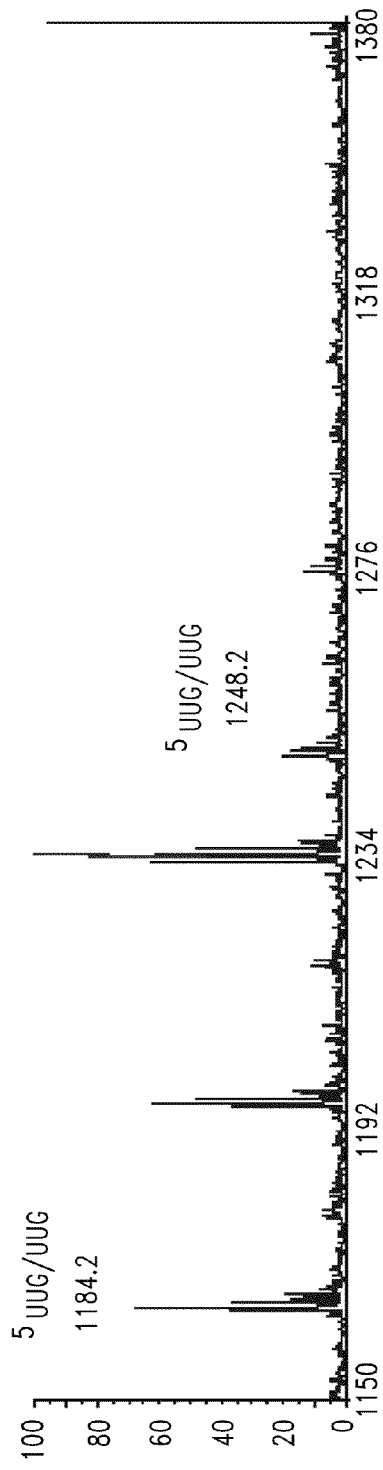
FIGS. 5A-B show the effect of AZL on replacement of Leu by Nal as evaluated by MALDI mass spectra of tryptic fragments of mDHFR.
Figure 5B:
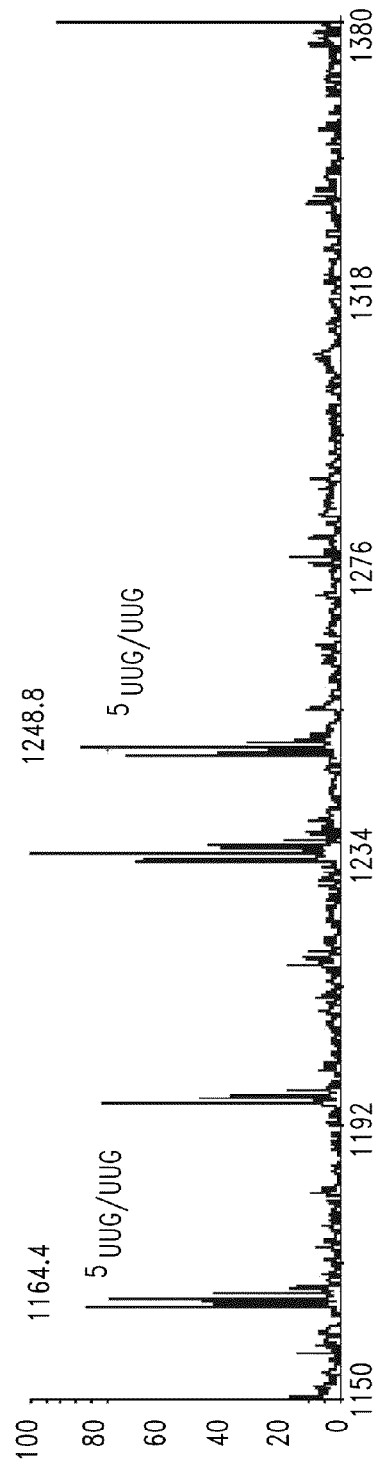

FIG. 5 shows the effect of AZL on replacement of Leu by Nal was evaluated by MALDI mass spectra of tryptic fragments of mDHFR. Peptide $5_{UUG/UUG}$ (residues 26-35, $NGDL_{UUG}PWPPL_{UUG}R$, SEQ ID NO: 8) contains two Leu residues encoded as UUG. Upon addition of Nal, the masses of these fragments shift in accord with the mass difference between Nal and Leu. Only Nal (a), Nal and 1 mM AZL (b) were supplemented into the media.

The practice of the present invention will employ, unless otherwise indicated, conventional techniques of molecular biology, cell biology, cell culture, microbiology and recombinant DNA, which are within the skill of the art. Such techniques are explained fully in the literature. See, for example, *Molecular Cloning: A Laboratory Manual*, $2^{nd}$ Ed., ed. By Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al.; U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987).

The contents of all cited references (including literature references, issued patents, published patent applications as cited throughout this application) are hereby expressly incorporated by reference.

Equivalents

Those skilled in the art will recognize, or be able to ascertain using no more than routine experimentation, numerous equivalents to the specific method and reagents described herein, including alternatives, variants, additions, deletions, modifications and substitutions. Such equivalents are considered to be within the scope of this invention and are covered by the following claims.

We claim:

1. A method for incorporating an unnatural amino acid into a target protein at one or more specified position(s), the method comprising:
   (1) providing to a translation system a first polynucleotide encoding a modified tRNA$^{Phe}$, wherein the modified tRNA comprises a modified anticodon sequence that forms Watson-Crick base-pairing with a wobble degenerate codon for a natural amino acid and wherein the modified tRNA$^{Phe}$ interacts with the wobble degenerate codon with an affinity of at least about 1.0 kcal/mole more favorably, at 37° C. than the interaction between unmodified tRNA$^{Phe}$ and the wobble degenerate codon, or the modified tRNA$^{Phe}$ encoded thereby;
   (2) providing to the translation system a second polynucleotide encoding a modified Aminoacyl tRNA Synthetase1 (AARS$^{Phe}$) with a relaxed substrate specificity where said modified AARS$^{Phe}$ is capable of charging the modified tRNA$^{Phe}$ with an unnatural amino acid in the absence of the natural amino acid or a modified AARS$^{Phe}$ that comprises a mutation at position 415 and is capable of charging the modified tRNA$^{Phe}$ with an unnatural amino acid more efficiently than a natural amino acid in the presence of both the natural and unnatural amino acid;
   (3) providing to the translation system the unnatural amino acid, wherein the unnatural amino acid is a phenylalanine analog selected from a meta-substituted phenylalanine, or para-substituted phenylalanine, wherein the substitution comprises an aldehyde group, alkenyl group, alkynl group, an azido group, a halogen group, a hydrazide group, a hydrazine group a hydroxyl group, a keto group, a methoxy group, or a methyl group;
   (4) providing to the translation system a template polynucleotide encoding the target protein, wherein the codon(s) on the template polynucleotide for the specified position(s) forms Watson-Crick base-pairing with the modified tRNA$^{Phe}$; and
   (5) allowing translation of the template polynucleotide, thereby incorporating the unnatural amino acid into the target protein at the specified position(s),
   wherein steps (1)-(4) are effectuated in any order.

2. The method of claim 1, wherein the translation system is a cell.

3. The method of claim 1, wherein the specificity constant ($k_{cat}/K_M$) for activation of the unnatural amino acid by the modified AARS$^{Phe}$ is at least 5-fold larger than that for the natural amino acid.

4. The method of claim 1, wherein the modified tRNA$^{Phe}$ is charged by an endogenous AARS$^{Phe}$ at a rate no more than 1% of that of its cognate tRNA$^{Phe}$.

5. The method of claim 1, wherein the first polynucleotide and/or the second polynucleotide further comprises either a constitutively active or an inducible promoter sequence that controls the expression of the modified tRNA$^{Phe}$ or AARS$^{Phe}$, respectively.

6. The method of claim 1, wherein the translation system is a cell, and the cell is auxotrophic for the natural amino acid encoded at the specified position.

7. The method of claim 1, wherein the translation system:
   (1) lacks endogenous tRNA that forms Watson-Crick base-pairing with the codon(s) at said specified position(s);
   (2) is a cell, and the method further comprises disabling one or more genes encoding any endogenous tRNA that forms Watson-Crick base-pairing with the codon(s) at said specified position(s); or
   (3) is a cell, and the method further comprises inhibiting one or more endogenous AARS that charges tRNAs that form Watson-Crick base-pairing with the codon(s) at said specified position(s).

8. The method of claim 1, wherein the cell is a bacterial cell, an *E. coli* cell, an insect cell, a mammalian cell, a fungal cell, or a yeast cell.

9. The method of claim 1, wherein the translation system is a cell, and the modified tRNA$^{Phe}$ and/or the modified AARS$^{Phe}$ are derived from an organism different from that of the cell.

10. The method of claim 1, wherein the phenylalanine analog is incorporated into the position at an efficiency of at least about 50%.

11. The method of claim 2, wherein the modified tRNA$^{Phe}$ is from an organism different from that of the cell.

12. The method of claim 11, wherein the modified tRNA$^{Phe}$ is from a yeast, and the cell is an *E. coli* bacterium.

13. The method of claim 1, wherein the translation system is a cell, the modified AARS$^{Phe}$ and the tRNA$^{Phe}$ are from the same organism, and the organism is different from the cell.

14. The method of claim 13, wherein the modified AARS$^{Phe}$ and the tRNA$^{Phe}$ are from a yeast, and the cell is an *E. coli* bacterium.

15. The method of claim 1, wherein the wobble degenerate codon is UUU or UUG.

* * * * *

UNITED STATES PATENT AND TRADEMARK OFFICE
CERTIFICATE OF CORRECTION

Page 1 of 1

PATENT NO.        : 8,835,162 B2
APPLICATION NO.   : 13/730116
DATED             : September 16, 2014
INVENTOR(S)       : Inchan Kwon et al.

It is certified that error appears in the above-identified patent and that said Letters Patent is hereby corrected as shown below:

On The Title Page,

Item (56), Other Publications:
"Peterson, "Determination of Recognition Nucleotides for *Escherichia coli* PhenylalanyltRNA Synthetase," *Biochemistry* 31(42): 10380-10389, Oct. 27, 1992." should read, -- Peterson, "Determination of Recognition Nucleotides for *Escherichia coli* Phenylalanyl-tRNA Synthetase," *Biochemistry* 31(42): 10380-10389, Oct. 27, 1992. --.

In The Claims,

Column 86, line 57:
"hydrazide group, a hydrazine group a hydroxyl group, a" should read, -- hydrazide group, a hydrazine group, a hydroxyl group, a --.

Signed and Sealed this
Twenty-third Day of February, 2016

Michelle K. Lee
*Director of the United States Patent and Trademark Office*

SEQUENCE LISTING

```
<160> NUMBER OF SEQ ID NOS: 8

<210> SEQ ID NO 1
<211> LENGTH: 8
<212> TYPE: PRT
<213> ORGANISM: Mus musculus

<400> SEQUENCE: 1

Tyr Lys Phe Glu Val Tyr Glu Lys
1               5

<210> SEQ ID NO 2
<211> LENGTH: 9
<212> TYPE: PRT
<213> ORGANISM: Mus musculus

<400> SEQUENCE: 2

Lys Thr Trp Phe Ser Ile Pro Glu Lys
1               5

<210> SEQ ID NO 3
<211> LENGTH: 14
<212> TYPE: PRT
<213> ORGANISM: Mus musculus

<400> SEQUENCE: 3

Asn Gly Asp Leu Pro Trp Pro Pro Leu Arg Asn Glu Phe Lys
1               5                   10

<210> SEQ ID NO 4
<211> LENGTH: 18
<212> TYPE: PRT
<213> ORGANISM: Mus musculus

<400> SEQUENCE: 4
```

```
Ile Met Gln Glu Phe Glu Ser Asp Thr Phe Phe Pro Glu Ile Asp Leu
1               5                   10                  15

Gly Lys

<210> SEQ ID NO 5
<211> LENGTH: 23
<212> TYPE: PRT
<213> ORGANISM: Mus musculus

<400> SEQUENCE: 5

Gly Ser Gly Ile Met Val Arg Pro Leu Asn Ser Ile Val Ala Val Ser
1               5                   10                  15

Gln Asn Met Gly Ile Gly Lys
            20

<210> SEQ ID NO 6
<211> LENGTH: 8
<212> TYPE: PRT
<213> ORGANISM: Mus musculus

<400> SEQUENCE: 6

Gln Asn Leu Val Ile Met Gly Arg
1               5

<210> SEQ ID NO 7
<211> LENGTH: 7
<212> TYPE: PRT
<213> ORGANISM: Mus musculus

<400> SEQUENCE: 7

Ser Leu Asp Asp Ala Leu Arg
1               5

<210> SEQ ID NO 8
<211> LENGTH: 10
<212> TYPE: PRT
<213> ORGANISM: Mus musculus

<400> SEQUENCE: 8

Asn Gly Asp Leu Pro Trp Pro Pro Leu Arg
1               5                   10
```